US012782358B2

(12) United States Patent
Mizumura et al.

(10) Patent No.: US 12,782,358 B2
(45) Date of Patent: Nov. 3, 2026

(54) REAGENT FOR MEASURING ß-GLUCAN, METHOD FOR PRODUCING SAME AND USE THEREOF

(71) Applicant: SEIKAGAKU CORPORATION, Tokyo (JP)

(72) Inventors: Hikaru Mizumura, Tokyo (JP); Yuki Kobayashi, Tokyo (JP); Naoki Takeshita, Tokyo (JP); Toshio Oda, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 356 days.

(21) Appl. No.: 18/294,301

(22) PCT Filed: Aug. 3, 2022

(86) PCT No.: PCT/JP2022/029728

§ 371 (c)(1),
(2) Date: Feb. 1, 2024

(87) PCT Pub. No.: WO2023/013661

PCT Pub. Date: Feb. 9, 2023

(65) Prior Publication Data

US 2025/0044296 A1 Feb. 6, 2025

(30) Foreign Application Priority Data

Aug. 4, 2021 (JP) ................................ 2021-128613
Oct. 27, 2021 (JP) ................................ 2021-175670
Jan. 27, 2022 (JP) ................................ 2022-010643

(51) Int. Cl.
*G01N 33/579* (2006.01)
*C07K 14/435* (2006.01)
*C12N 9/64* (2006.01)

(52) U.S. Cl.
CPC ..... *G01N 33/579* (2013.01); *C07K 14/43509* (2013.01); *C12N 9/6408* (2013.01); *C12Y 304/21086* (2013.01); *G01N 2333/43508* (2013.01); *G01N 2800/26* (2013.01)

(58) Field of Classification Search
CPC ............ G01N 2800/26; G01N 33/579; G01N 2333/43508; C07K 14/43509; C12N 9/6408; C12Y 304/21086
See application file for complete search history.

(56) References Cited

U.S. PATENT DOCUMENTS

| | | | | |
|---|---|---|---|---|
| 5,795,962 | A | 8/1998 | Iwanaga et al. | |
| 2006/0228779 | A1 | 10/2006 | Tamura | |
| 2007/0207209 | A1 | 9/2007 | Murphy et al. | |
| 2009/0208995 | A1 | 8/2009 | Tamura et al. | |
| 2021/0363564 | A1 * | 11/2021 | Kobayashi ........... | C12N 9/6408 |
| 2022/0306705 | A1 | 9/2022 | Yamamoto et al. | |

FOREIGN PATENT DOCUMENTS

| | | | |
|---|---|---|---|
| JP | 2006-271384 | A | 10/2006 |
| WO | 95/01432 | A1 | 1/1995 |
| WO | 2008/004674 | A1 | 1/2008 |
| WO | 2021/117841 | A1 | 6/2021 |

OTHER PUBLICATIONS

Kawabata, Shun-ichiro, et al. "Limulus factor D, a 43-kDa protein isolated from horseshoe crab hemocytes, is a serine protease homologue with antimicrobial activity." Febs Letters 398.2-3 (1996): 146-150. (Year: 1996).*
Extended European Search Report, dated Jul. 16, 2025. issued in European family member Application No. 22853080.4.
Iwanaga, "Biochemical principle of *Limulus* test for detecting bacterial endotoxins", Proceedings of the Japan Academy. Series B, Physical and Biological Sciences, vol. 83, No. 4, 2007, pp. 110-119.
Iwanaga, "The limulus clotting reaction", Current Opinion in Immunology, vol. 5, No. 1, 1993, pp. 74-82.
Iwanaga, Proceedings of the Japan Academy. Series B, Physical and Biological Sciences, vol. 83, No. 4, 2007, pp. 110-119.
Iwanaga, Current Opinion in Immunology, vol. 5, No. 1, 1993, pp. 74-82.
Kawabata et al., "Limulus factor D, a 43-kDa protein isolated from horseshoe crab hemocytes, is a serine protease homologue with antimicrobial activity ", FEBS Letters, vol. 398, 1996, pp. 146-150.
Seki et al., "Horseshoe Crab (1,3)-B-D-Glucan-sensitive Coagulation Factor G", The Journal of Biological Chemistry, vol. 269, No. 2, 1994, pp. 1370-1374.
International Search Report issued Oct. 25, 2022 in International Bureau of WIPO Patent Application No. PCT/JP2022/029728, with an English translation thereof.
Written Opinion issued Oct. 25, 2022 in International Bureau of WIPO Patent Application No. PCT/JP2022/029728, with an English translation thereof.

* cited by examiner

*Primary Examiner* — Robert J Yamasaki
*Assistant Examiner* — Trevor Kane
(74) *Attorney, Agent, or Firm* — Greenblum & Bernstein, P.L.C.

(57) ABSTRACT

A reagent for β-glucan measurement without requiring a horseshoe crab hemocyte extract by using horseshoe crab-derived factor D in the reagent for β-glucan measurement.

11 Claims, 4 Drawing Sheets

Specification includes a Sequence Listing.

SEQUENCE LISTING

```
Sequence total quantity: 72
SEQ ID NO: 1            moltype = AA  length = 394
FEATURE                 Location/Qualifiers
source                  1..394
                        mol_type = protein
                        organism = Tachypleus tridentatus
SEQUENCE: 1
MKVLLLVAFL LGTTLAYPQD DDGPVWGGSS NDNDDGGISS RVGNPQSGFG NCECVPYYLC  60
KDNNIIIDGS GLLDPRKKPV ASKEPKLSAR LGPEGPSGCG PFHVCCIAPE TSTVKPYTHQ  120
CGFRNVNGIN KRILSPNGKD LSEFGEWPWQ GAVLKVEGKV NIFQCGAVLI DSYHLLTVAH  180
CVYKFTLENA FPLKVRLGEW DTQNTNEFLK HEDYEVEKIY IHPKYDDERK NLWDDIAILK  240
LKAEVSFGPH IDTICLPNNQ EHFAGVQCVV TGWGKNAYKN GSYSNVLREV HVPVITNDRC  300
QELLRKTRLS EWYVLYENFI CAGGESNADS CKGDGGGPLT CWRKDGTYGL AGLVSWGINC  360
GSPNVPGVYV RVSNYLDWIT KITGRPISDY WPRS                            394

SEQ ID NO: 2            moltype = AA  length = 376
FEATURE                 Location/Qualifiers
source                  1..376
                        mol_type = protein
                        organism = Tachypleus tridentatus
SEQUENCE: 2
QDDDGPVWGG SSNDNDDGGI SSRVGNPQSG FGNCECVPYY LCKDNNIIID GSGLLDPRKK  60
PVASKEPKLS ARLGPEGPSG CGPFHVCCIA PETSTVKPYT HQCGFRNVNG INKRILSPNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVSNYLDW  360
ITKITGRPIS DYWPRS                                                376

SEQ ID NO: 3            moltype = AA  length = 394
FEATURE                 Location/Qualifiers
source                  1..394
                        mol_type = protein
                        organism = Tachypleus tridentatus
SEQUENCE: 3
MKVLLLVAFL LGTTLAYPQD DDGPVWGGSS NDNDDGGISS RVGNPQSGFG NCECVPYYLC  60
KDNNIIIDGS GLLDPRKKPV ASKEPKLSAR LGPEGPSGCG PFHVCCIAPE TSTVKPYTHQ  120
CGFRNVNGIN KRILSPNGKD LSEFGEWPWQ GAVLKVEGKV NIFQCGAVLI DSYHLLTVAH  180
CVYKFTLENA FPLKVRLGEW DTQNTNEFLK HEDYEVEKIY IHPKYDDERK NLWDDIAILK  240
LKAEVSFGPH IDTICLPNNQ EHFAGVQCVV TGWGKNAYKN GSYSNVLREV HVPVITNDRC  300
QELLRKTRLS EWYVLYENFI CAGGESNADS CKGDGGGPLT CWRKDGTYGL AGLVSWGINC  360
GSPNVPGVYV RVANYLDWIT KITGRPISDY WPRS                            394

SEQ ID NO: 4            moltype = AA  length = 376
FEATURE                 Location/Qualifiers
```

```
source                  1..376
                        mol_type = protein
                        organism = Tachypleus tridentatus
SEQUENCE: 4
QDDDGPVWGG SSNDNDDGGI SSRVGNPQSG FGNCECVPYY LCKDNNIIID GSGLLDPRKK  60
PVASKEPKLS ARLGPEGPSG CGPFHVCCIA PETSTVKPYT HQCGFRNVNG INKRILSPNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVANYLDW  360
ITKITGRPIS DYWPRS                                                 376

SEQ ID NO: 5            moltype = AA  length = 413
FEATURE                 Location/Qualifiers
source                  1..413
                        mol_type = protein
                        organism = Tachypleus tridentatus
SEQUENCE: 5
MGILPSPGMP ALLSLVSLLS VLLMGCVAET GQDDDGPVWG GSSNDNDDGG ISSRVGNPQS  60
GFGNCECVPY YLCKDNNIII DGSGLLDPRK KPVASKEPKL SARLGPEGPS GCGPFHVCCI  120
APETSTVKPY THQCGFRNVN GINKRILSPN GKDLSEFGEW PWQGAVLKVE GKVNIFQCGA  180
VLIDSYHLLT VAHCVYKFTL ENAFPLKVRL GEWDTQNTNE FLKHEDYEVE KIYIHPKYDD  240
ERKNLWDDIA ILKLKAEVSF GPHIDTICLP NNQEHFAGVQ CVVTGWGKNA YKNGSYSNVL  300
REVHVPVITN DRCQELLRKT RLSEWYVLYE NFICAGGESN ADSCKGDGGG PLTCWRKDGT  360
YGLAGLVSWG INCGSPNVPG VYVRVANYLD WITKITGRPI SDYWPRSHHH HHH        413

SEQ ID NO: 6            moltype = AA  length = 385
FEATURE                 Location/Qualifiers
source                  1..385
                        mol_type = protein
                        organism = Tachypleus tridentatus
SEQUENCE: 6
ETGQDDDGPV WGGSSNDNDD GGISSRVGNP QSGFGNCECV PYYLCKDNNI IIDGSGLLDP  60
RKKPVASKEP KLSARLGPEG PSGCGPFHVC CIAPETSTVK PYTHQCGFRN VNGINKRILS  120
PNGKDLSEFG EWPWQGAVLK VEGKVNIFQC GAVLIDSYHL LTVAHCVYKF TLENAFPLKV  180
RLGEWDTQNT NEFLKHEDYE VEKIYIHPKY DDERKNLWDD IAILKLKAEV SFGPHIDTIC  240
LPNNQEHFAG VQCVVTGWGK NAYKNGSYSN VLREVHVPVI TNDRCQELLR KTRLSEWYVL  300
YENFICAGGE SNADSCKGDG GGPLTCWRKD GTYGLAGLVS WGINCGSPNV PGVYVRVANY  360
LDWITKITGR PISDYWPRSH HHHHH                                       385

SEQ ID NO: 7            moltype = AA  length = 394
FEATURE                 Location/Qualifiers
source                  1..394
                        mol_type = protein
                        organism = Limulus polyphemus
SEQUENCE: 7
MKVLLLMTFL FETALAYPQD DDGPIWGGSN SDNDDGSINS RVDNPHSGFG NCECVPYYVC  60
KDDNIITDGS GVLDPRKKPV PSKEPDLFAH LSPEGRRGCG NFHVCCIAPT TSTVKPYTRQ  120
CGFRKVNGIN KRILSPNGKN LSEFGEWPWQ GAVLKVEGKV NIFQCGAVLI DSFHLLTVAH  180
CVYRFTLENA FPLKVRLGEW DTQNTNEFLK HEDYEVEKIS IHSKYNHERK NLWDDIAILK  240
LKVEVSFGPH IDTICLPKYQ EKFEGVQCVV TGWGKNAYKN GSYTNVLRKA HVPVISNDKC  300
QQLLRKTRLS KWFILYENFI CAGGESNADS CKGDGGGPLA CWRKDGTYGL AGLVSWGIGC  360
GSPNVPGVYV RVTNYLDWIT EVTGRPISEY WPRS                             394

SEQ ID NO: 8            moltype = AA  length = 376
FEATURE                 Location/Qualifiers
source                  1..376
                        mol_type = protein
                        organism = Limulus polyphemus
SEQUENCE: 8
QDDDGPIWGG SNSDNDDGSI NSRVDNPHSG FGNCECVPYY VCKDDNIITD GSGVLDPRKK  60
PVPSKEPDLF AHLSPEGRRG CGNFHVCCIA PTTSTVKPYT RQCGFRKVNG INKRILSPNG  120
KNLSEFGEWP WQGAVLKVEG KVNIFQCGAV LIDSFHLLTV AHCVYRFTLE NAFPLKVRLG  180
EWDTQNTNEF LKHEDYEVEK ISIHSKYNHE RKNLWDDIAI LKLKVEVSFG PHIDTICLPK  240
YQEKFEGVQC VVTGWGKNAY KNGSYTNVLR KAHVPVISND KCQQLLRKTR LSKWFILYEN  300
FICAGGESNA DSCKGDGGGP LACWRKDGTY GLAGLVSWGI GCGSPNVPGV YVRVTNYLDW  360
ITEVTGRPIS EYWPRS                                                 376

SEQ ID NO: 9            moltype = AA  length = 396
FEATURE                 Location/Qualifiers
source                  1..396
                        mol_type = protein
                        organism = Limulus polyphemus
SEQUENCE: 9
MKVLLLMTFL FGTALAYPQD DDGPVWGGSN NDDDDDDGGI SSRVGNPQSS FGNCECVPYY  60
LCKDNNIITD GSGVLDPRKK PVPSKEPGLS ARLGPEGPSG CGPFHVCCTA PTTSTVKPYT  120
HQCGFRNVNG INKRILSPNG KDLSEFGEWP WQGAVLKVEG KVNIFQCGAV LIDSFHLLTV  180
AHCVYRFTLA NAFPLKVRLG EWDTQNTDEF LKHEDYEVEK IYIHSKYNHE RKNLWDDIAI  240
LKLKVEVSFG PHIDTICLPN YQENFEGVQC VVTGWGKNAY KNGTYSNVLR EVHVPVISND  300
```

```
KCEQLLKETR LSKWFVLYEN FTCAGGESNA DSCKGDGGGP LACWRKDGTY ALAGLVSWGI  360
DCGSPNVPGV YVRVAKYLDW IAQITGRPVT DYWPRS                            396

SEQ ID NO: 10          moltype = AA  length = 378
FEATURE                Location/Qualifiers
source                 1..378
                       mol_type = protein
                       organism = Limulus polyphemus
SEQUENCE: 10
QDDDGPVWGG SNNDDDDDDG GISSRVGNPQ SSFGNCECVP YYLCKDNNII TDGSGVLDPR  60
KKPVPSKEPG LSARLGPEGP SGCGPFHVCC TAPTTSTVKP YTHQCGFRNV NGINKRILSP  120
NGKDLSEFGE WPWQGAVLKV EGKVNIFQCG AVLIDSFHLL TVAHCVYRFT LANAFPLKVR  180
LGEWDTQNTD EFLKHEDYEV EKIYIHSKYN HERKNLWDDI AILKLKVEVS FGPHIDTICL  240
PNYQENFEGV QCVVTGWGKN AYKNGTYSNV LREVHVPVIS NDKCEQLLKE TRLSKWFVLY  300
ENFTCAGGES NADSCKGDGG GPLACWRKDG TYALAGLVSW GIDCGSPNVP GVYVRVAKYL  360
DWIAQITGRP VTDYWPRS                                                378

SEQ ID NO: 11          moltype = AA  length = 415
FEATURE                Location/Qualifiers
source                 1..415
                       mol_type = protein
                       organism = Limulus polyphemus
SEQUENCE: 11
MGILPSPGMP ALLSLVSLLS VLLMGCVAET GQDDDGPVWG GSNNDDDDDD GGISSRVGNP  60
QSSFGNCECV PYYLCKDNNI ITDGSGVLDP RKKPVPSKEP GLSARLGPEG PSGCGPFHVC  120
CTAPTTSTVK PYTHQCGFRN VNGINKRILS PNGKDLSEFG EWPWQGAVLK VEGKVNIFQC  180
GAVLIDSFHL LTVAHCVYRF TLANAFPLKV RLGEWDTQNT DEFLKHEDYE VEKIYIHSKY  240
NHERKNLWDD IAILKLKVEV SFGPHIDTIC LPNYQENFEG VQCVVTGWGK NAYKNGTYSN  300
VLREVHVPVI SNDKCEQLLK ETRLSKWFVL YENFTCAGGE SNADSCKGDG GGPLACWRKD  360
GTYALAGLVS WGIDCGSPNV PGVYVRVAKY LDWIAQITGR PVTDYWPRSH HHHHH       415

SEQ ID NO: 12          moltype = AA  length = 387
FEATURE                Location/Qualifiers
source                 1..387
                       mol_type = protein
                       organism = Limulus polyphemus
SEQUENCE: 12
ETGQDDDGPV WGGSNNDDDD DDGGISSRVG NPQSSFGNCE CVPYYLCKDN NIITDGSGVL  60
DPRKKPVPSK EPGLSARLGP EGPSGCGPFH VCCTAPTTST VKPYTHQCGF RNVNGINKRI  120
LSPNGKDLSE FGEWPWQGAV LKVEGKVNIF QCGAVLIDSF HLLTVAHCVY RFTLANAFPL  180
KVRLGEWDTQ NTDEFLKHED YEVEKIYIHS KYNHERKNLW DDIAILKLKV EVSFGPHIDT  240
ICLPNYQENF EGVQCVVTGW GKNAYKNGTY SNVLREVHVP VISNDKCEQL LKETRLSKWF  300
VLYENFTCAG GESNADSCKG DGGGPLACWR KDGTYALAGL VSWGIDCGSP NVPGVYVRVA  360
KYLDWIAQIT GRPVTDYWPR SHHHHHH                                      387

SEQ ID NO: 13          moltype = AA  length = 673
FEATURE                Location/Qualifiers
source                 1..673
                       mol_type = protein
                       organism = Tachypleus tridentatus
SEQUENCE: 13
MLVLLCCVVL HVGVARICCS HEPKWQLVWS DEFTNGISSD WEFEMGNGLN GWGNNELQYY  60
RRENAQVEGG KLVITAKRED YDGFKYTSAR LKTQFDKSWK YGKIEAKMAI PSFRGVWVMF  120
WMSGDNTNYV RWPSSGEIDF IEHRNTNNEK VRGTIHWSTP DGAHAHHNRE SNTNGIDYHI  180
YSVEWNSSIV KWFVNGNQYF EVKIQGGVNG KSAFRNKVFV ILNMAIGGNW PGFDVADEAF  240
PAKMYIDYVR VYQDASTSSP VGDTSLDGYY FVQNRHSELY LDVTDASNED GAFLQQWSYS  300
GNENQQFDFE HLENNVYKIT NKKSGKSLDV YNFGTENGVR IQQWSYGGAR NQQFTVQSVG  360
DGYYKIIPRG SGKLVEVADF SKDAGGKIQQ WSDNNQLSGQ WKLIKSKSYS KLIQAESYFD  420
SSKVQLEDTS DVGGGKNVKC DNEGAWMAYK DIDFPSSGNY RIEYRVASER AGGKLSLDLN  480
AGSIVLGMLD VPSTGGWQKW TTISHTVNVD SGTYNLGIYV QRASWNINWI KITKIPEQSN  540
LNQGRRNSKL IQAESYFSYS EVQLEDTLDV GGGKNVKCDK EGAWMAYKDI DFPSSGSYRV  600
EYRVASERAG GKLSLDLNAG SIVLGMLDIP STGGLQKWTT ISHIVNVDLG TYNLGIYVQK  660
ASWNINWIRI TKV                                                     673

SEQ ID NO: 14          moltype = AA  length = 309
FEATURE                Location/Qualifiers
source                 1..309
                       mol_type = protein
                       organism = Tachypleus tridentatus
SEQUENCE: 14
MDISFLVFIT LSMALFSSNV TGTSVTSRVR RGINEKHCGF RPVITRIIGG GIATPHSWPW  60
MVGIFKVNPH RFLCGGSIIN KVSVVTAAHC LVTQFGNRQN YSIFVRVGAH DIDNSGTNYQ  120
VDKVIVHQGY KHHSHYYDIG LILLSKPVEY NDKIQPVCIP EFNKPHVNLN NIKVVITGWG  180
VTGKATEKRN VLRELELPVV TNEQCNKSYQ TLPFSKLNRG ITNDMICAGF PEGGKDACQG  240
DSGGPLMYQN PTTGRVKIVG VVSFGFECAR PNFPGVYTRL SSYVNWLQEI TFGQSLASLF  300
EVVPIFIPE                                                          309

SEQ ID NO: 15          moltype = AA  length = 668
FEATURE                Location/Qualifiers
```

```
source                  1..668
                        mol_type = protein
                        organism = Limulus polyphemus
SEQUENCE: 15
MLVLLCCVVL HVGVARICCS QEPKWKLVWS DEFTNGISSD WEFETGNGPN GWGNNELQYY  60
RRENTRVEGG KLIITAKEED YEGFRYTSAK LKTQFNKPWK DGKIEARMSI PSFRGVWVAF  120
WMLGDITDTD SWPSSGEIDF EEHINTNNEV RGTIHWSTSD DADTLHGRGT NTDYHIYSVE  180
WNSSVIRWFV DGNQYFDVNI QRGATGTNAF HNNVFVILNM AIGGNWPGFN VADEAFPANM  240
YVDYVRVYQD ANTPSPVDVT HLSGYYFLQN RHSELYLDVS GSSNEDGAFL QQWPYSGNAN  300
QQFDFVHLGN KVYKIINKNS GKSLDVYELG TDNGVRIQQW SYGGGYNQQF IVQDVGDGYY  360
KIFARSTGKL VEVADLNKDP GGKIQQWSDD GQLSGQWKLI RNKANSKLIQ AESYFASSKV  420
QLEDTSDVGG GKNVKCDNEG AWMAYKDINF PSSGTYQVEY RVASERAGGM LSLDLNAGSI  480
VLGMLNVPST GGLQKWTTIS HTVNVSSGTY NLGISVQRPG WNINWINITK VSSQLKSIPS  540
TNSRVIQAES YFDSSKVQLE DTSDVGGGKN VKCDTKGAWM AYKDINFPSS GSYQIEYRVA  600
SERAGGKLSL DLNAGSIVLG MLDVPSTGGW QKWTTISHTV KVDSGTYNLG IYVQQPGWNI  660
NWIKITKV                                                          668

SEQ ID NO: 16           moltype = AA  length = 666
FEATURE                 Location/Qualifiers
source                  1..666
                        mol_type = protein
                        organism = Limulus polyphemus
SEQUENCE: 16
MFLCYVVLYV GVAGIYCSQE PKWKLVWSDE FTNGISSDWE FETGNGPNGW GNNELQYYRR  60
ENTRVEGGKL IITAKEEDYE GFRYTSAKLK TQFNKPWKDG KIEARMSIPS FRGVWVAFWM  120
LGDITDTDSW PSSGEIDFEE HINTNNEVRG TIHWSTSDDA DTLHGRGTNT DYHIYSVEWN  180
SSVIRWFVDG NQYFEVNIQR GATGTNAFHN NVFVILNMAI GGNWPGFNVA DEAFPANMYV  240
DYVRVYQDAN TPSPVDVTHL SGYYFLQNRH SELYLDVSGS SNEDGAFLQQ WPYSGNANQQ  300
FDFVHLGNKV YKIINKNSGK SLDVYELGTD NGVRIQQWSY GGGYNQQFIV QDVGDGYYKI  360
FARSTGKLVE VADLNKDPGG KIQQWSDDGQ LSGQWKLIRN KANSKLIQAE SYFASSKVQL  420
EDTSDVGGGK NVKCDNEGAW MAYKDINFPS SGTYQVEYRV ASERAGGMLS LDLNAGSIVL  480
GMLNVPSTGG LQKWTTISHT VNVSSGTYNL GISVQRPGWN INWINITKVS SQLKSIPSTN  540
SRVIQAESYF DSSKVQLEDT SDVGGGKNVK CDTKGAWMAY KDINFPSSGS YQIEYRVASE  600
RAGGKLSLDL NAGSIVLGML DVPSTGGWQK WTTISHTVKV DSGTYNLGIY VQQPGWNINW  660
IKITKV                                                            666

SEQ ID NO: 17           moltype = AA  length = 670
FEATURE                 Location/Qualifiers
source                  1..670
                        mol_type = protein
                        organism = Limulus polyphemus
SEQUENCE: 17
MFLCYVVLVV GVTGICCSQE TNWKLVWSDE FTNGISSDWE FETGNGPNGW GNNELQYYRR  60
ENARVEGGKL IITAKKEDYE GFRYTSAKLK TQFNKPWKDG KIEARMSIPS FRGVWVAFWM  120
LGDITDTDSW PSSGEIDFKE HINTNNEVRG TIHWSTSDGA HTHHGRGTNT DYHIYSVEWN  180
SSVIRWFVDG NQYFEVNIQR GATGTNAFHN KVFVILNMAI GGNWPGFNVA DEAFPANMYV  240
DYVRVYQDAN TPSPVDVDVT DLSGYYFLQN RHSELYLDVS FSSNKDGAFL QQWPYNGNAN  300
QQFDFVHLGN NIYKITNKNS GKSLDVYNVG TENGVRIQQM PYRGSYNQQF IVQDVGDGYY  360
KIFARNSRKL VEVADFNKDP GGKIQQWSDD GQISGQWKLI RNKVNSKVIQ AESYFASLGV  420
QLEDTSDVGG GKNVKCDTEG AWMAYKDINF PSSGSYQVEY RVASERAGGK LSLDLNAGSI  480
VLGMLNVPST GGWQKWTTIS HTVKVDSGTY NLGIYVQRPR WNINWIKITE APGQSKPIQR  540
SDTDSKVIQA ESYFASSKVQ LEDTSDVGGG KNVKCDNEGA WMAYKDINFP SSGSYQIEYR  600
VASERAGGKL SLDLNAGSIV LGMLDVPSTG GWQKWTTISH TVNVSSGTYN LGIYVQRAAW  660
NINWIKITKV                                                        670

SEQ ID NO: 18           moltype = AA  length = 308
FEATURE                 Location/Qualifiers
source                  1..308
                        mol_type = protein
                        organism = Limulus polyphemus
SEQUENCE: 18
MKTTLWTFFA LAMALFSINV TASEMSVTSR VRREINEEHC GIRPTAPRII KGRISIPHSW  60
PWMVGIFQVD PLLFICGGTI INKVSVVTAA HCLVTQSGNR QNSSIVVRVG AHDIDNSGID  120
YHVDKIIVHQ DYKYRSQYYD IGLILLSKRI EYNYKVRPVC IPELNKLNVN LNNKEVVVIG  180
WGVTERGSEK HNVLRELELP VVTNELCNKS YQTISFSGLN RGITDDMICA GYQEGGRDSC  240
EGDSGGPLMY HDPTTGRVEL VGVVSFGFGC ARPNFPGVYT RLSSYGNWFQ KVTFGYLLAT  300
LFEVVPVF                                                          308

SEQ ID NO: 19           moltype = AA  length = 308
FEATURE                 Location/Qualifiers
source                  1..308
                        mol_type = protein
                        organism = Limulus polyphemus
SEQUENCE: 19
MKTTLWTFFA LAMALFSINV TASEMSVTSR VRREINEEHC GIRPTAPRII KGRISIPHSW  60
PWMVGIFQVD PLLFICGGTI INKVSVVTAA HCLVTQSGNR QNSSIVVRVG AHDIDNSGID  120
YHVDKIIVHQ DYKYRSQYYD IGLILLSKPI EYNYKVRPVC IPELNKLNVN LNNKEVVVIG  180
WGVTERGSEK YNVLRELELP VVTNELCNKS YQTISFSGLN RGITDDMICA GYQEGGRDSC  240
```

-continued

```
EGDSGGPLMY HDPTTGRVEL VGVVSFGFGC ARPNFPGVYT RLSSYGNWFQ KVTFGYLLAT  300
LFEVVPVF                                                          308

SEQ ID NO: 20          moltype = AA  length = 308
FEATURE                Location/Qualifiers
source                 1..308
                       mol_type = protein
                       organism = Limulus polyphemus
SEQUENCE: 20
MKTTLWTFFA LAMALFSINV TASEMSVTSR VRREINEEHC GIRPTAPRII KGRISIPHSW  60
PWMVGIFQVD PLLFICGGTI INKVSVVTAA HCLVTQSGNR QNYSIVVRVG AHDIDNSGID  120
YHVDKIIVHQ DYKYRSQYYD IGLILLSKPI EYNYKVRPVC IPELNKLNVN LNNKEVVVIG  180
WGVTERGSEK HNVLRELELP VVTNELCNKS YQTISFSGLN RGITDDMICA GYQEGGRDSC  240
EGDSGGPLMY HDPTTGGVEL VGVVSFGFGC ARPNFPGVYT RLSSYGNWFQ KVTFGYLLAT  300
LFEVVPVF                                                          308

SEQ ID NO: 21          moltype = AA  length = 308
FEATURE                Location/Qualifiers
source                 1..308
                       mol_type = protein
                       organism = Limulus polyphemus
SEQUENCE: 21
MKTTLWTFFA LAMALFSINV TASEMSVTSR VRREINEEHC GIRPTAPRII KGRISIPHSW  60
PWMVGIFQVD PLLFICGGTI INKVSVVTAA HCLVTQSGNR QNYSIVVRVG AHDIDNSGID  120
YHVDKIIVHQ DYKYRSQYYD IGLILLSKPI EYNYKVRPVC IPELNKLNVN LNNKEVVVIG  180
WGVTERGSEK YNVLRELELP VVTNELCNKS YQTISFSGLN RGITDDMICA GYQEGGRDSC  240
EGDSGGPLMY HDPTTGRVEL VGVVSFGFGC ARPNFPGVYT RLSSYGNWFQ KVTFGYLLAT  300
LFEVVPVF                                                          308

SEQ ID NO: 22          moltype = AA  length = 308
FEATURE                Location/Qualifiers
source                 1..308
                       mol_type = protein
                       organism = Limulus polyphemus
SEQUENCE: 22
MKTTLWTFFA LAMALFSINV TASEMSVTSR VRREINEEHC GIRPTAPRII KGRISIPHSW  60
PWMVGIFQVD PLLFICGGTI INKVSVVTAA HCLVTQSGNR QNSSIVVRVG AHDIDNSGID  120
YHVDKIIVHQ DYKYRSQYYD IGLILLSKRI EYNYKVRPVC IPELNKLNVN LNNKEVVVIG  180
WGVTERGSEK YNVLRELELP VVTNELCNKS YQTISFSGLN RGITDDMICA GYQEGGRDSC  240
EGDSGGPLMY HDPTTGRVEL VGVVSFGFGC ARPNFPGVYT RLSSYGNWFQ KVTFGYLLAT  300
LFEVVPVF                                                          308

SEQ ID NO: 23          moltype = AA  length = 308
FEATURE                Location/Qualifiers
source                 1..308
                       mol_type = protein
                       organism = Limulus polyphemus
SEQUENCE: 23
MKTTLWTFFA LAMALFSINV TASEMSVTSR VRREINEEHC GIRPTAPRII KGRISIPHSW  60
PWMVGIFQVD PLLFICGGTI INKVSVVTAA HCLVTQSGNR QNYSIVVRVG AHDIDNSGID  120
YHVDKIIVHQ DYKYRSQYYD IGLILLSKPI EYNYKVRPVC IPELNKLNVN LNNKEVVVIG  180
WGVTERGSEK HNVLRELELP VVTNELCNKS YQTISFSGLN RGITDDMICA GYQEGGRDSC  240
EGDSGGPLMY HDPTTGRVEL VGVVSFGFGC ARPNFPGVYT RLSSYGNWFQ KVTFGYLLAT  300
LFEVVPVF                                                          308

SEQ ID NO: 24          moltype = AA  length = 375
FEATURE                Location/Qualifiers
source                 1..375
                       mol_type = protein
                       organism = Tachypleus tridentatus
SEQUENCE: 24
MLVNNVFSLL CFPLLMSVVR CSTLSRQRRQ FVFPDEEELC SNRFTEEGTC KNVLDCRILL  60
QKNDYNLLKE SICGFEGITP KVCCPKSSHV ISSTQAPPET TTERPPKQI PPNLPEVCGI  120
HNTTTTRIIG GREAPIGAWP WMTAVYIKQG GIRSVQCGGA LVTNRHVITA SHCVVNSAGT  180
DVMPADVFSV RLGEHNLYST DDDSNPIDFA VTSVKHHEHF VLATYLNDIA ILTLNDTVTF  240
TDRIRPICLP YRKLRYDDLA MRKPFITGWG TTAFNGPSSA VLREVQLPIW EHEACRQAYE  300
KDLNITNVYM CAGFADGGKD ACQGDSGGPM MLPVKTGEFY LIGIVSFGKK CALPGFPGVY  360
TKVTEFLDWI AEHMV                                                  375

SEQ ID NO: 25          moltype = AA  length = 375
FEATURE                Location/Qualifiers
source                 1..375
                       mol_type = protein
                       organism = Limulus polyphemus
SEQUENCE: 25
MLVNNMFSLL CFPLLMSMFS CSSLGRQRRQ FVFPDDEESC SNRFTNDGIC KDVLNCRDLL  60
QKNDYNLLKE SICGFEGITP KVCCPKQSIV NPITEAPPKT TTERPPIRI PSNLPKQCGN  120
RNITTTRIIG GQEATPGAWP WMAAVYIKQG GIRSVQCGGA LVTNRHVITA SHCVVNSLGT  180
DVMRADVFSV RLGEHNLYST NDSSDPIDFA VTSVKHHENF VLATYLNDIA ILKLNDTVTF  240
```

-continued

```
THKIKPICLP YESLRYEDLA MRNPFVAGWG TTAFNGPSSA VLREVQLPIW GHEPCRQAYE  300
KDLNITNVYM CAGYADGGKD ACQGDSGGPM MLPDKSGNFY LVGIVSFGKK CALPGFPGVY  360
TKVTEFLDWI AVNMV                                                   375

SEQ ID NO: 26          moltype = DNA  length = 1185
FEATURE                Location/Qualifiers
source                 1..1185
                       mol_type = genomic DNA
                       organism = Tachypleus tridentatus
SEQUENCE: 26
atgaaagtgt tgttgttggt ggctttcctt ttgggaacga cgttggctta tccacaagac  60
gatgacgggc cagtctgggg tggttcaagc aacgataatg atgatggtgg tattagcagt  120
cgcgttggca acccccaatc tggttttggt aactgtgagt gtgtacctta ttacttgtgt  180
aaggataata atattatcat tgatggttct ggcttactcg accctagaaa aaaaccagta  240
gcctccaaag aacctaaatt gtctgcacgc ctaggtccag aaggtccaag tgggtgtggt  300
ccttttcacg tatgctgtat tgcaccagaa acatccacag taaaaccata tactcatcaa  360
tgtggcttca gaaacgtcaa tggaatcaac aagcgtattt tgagtcctaa tggtaaagat  420
ctatctgagt ttggagagtg gccttggcag ggagctgtat tgaaagtcga aggcaaagtt  480
aacatcttcc agtgtggtgc cgttcttata gacagttatc acttacttac tgtagcccat  540
tgcgtttaca agtttacgct tgaaaatgct tttcccttga aagtaagact gggagaatgg  600
gacacccaaa ataccaatga gttcttgaag catgaagatt atgaagtgga aaaaatttac  660
attcatccta aatatgatga tgaaaggaaa aacttgtggg acgacattgc tattttgaaa  720
ctgaaagctg aagtttcctt tggtcctcac attgacacta tctgcttacc aaataatcaa  780
gaacattttg caggtgttca gtgtgtggtt actggttggg gaaagaatgc ctacaaaaat  840
ggttcgtact ccaatgtatt aagggaagtc cacgtgcctg ttattactaa cgataggtgt  900
caggagcttc tgaggaaaac tagattaagt gaatggtacg tcttgtacga aaactttatc  960
tgtgctggtg gagaaagtaa cgccgactct tgcaagggag acggaggtgg tcctttaacg  1020
tgctggagga aagatggtac ttatggactg gcaggtctgg tatcatgggg aattaactgt  1080
ggtagtccta atgtgcctgg tgtttatgtc agagtctcaa attatcttga ctggattacc  1140
aagattaccg gtcgtccaat ttctgattac tggccacgtt cgtaa                  1185

SEQ ID NO: 27          moltype = DNA  length = 1185
FEATURE                Location/Qualifiers
source                 1..1185
                       mol_type = genomic DNA
                       organism = Tachypleus tridentatus
SEQUENCE: 27
atgaaagtgt tgttgttggt ggctttcctt ttgggaacga cgttggctta tccacaagac  60
gatgacgggc cagtctgggg tggttcaagc aacgataatg atgatggtgg tattagcagt  120
cgcgttggca acccccaatc tggttttggt aactgtgagt gtgtacctta ttacttgtgt  180
aaggataata atattatcat tgatggttct ggcttactcg accctagaaa aaaaccagta  240
gcctccaaag aacctaaatt gtctgcacgc ctaggtccag aaggtccaag tgggtgtggt  300
ccttttcacg tatgctgtat tgcaccagaa acatccacag taaaaccata tactcatcaa  360
tgtggcttca gaaacgtcaa tggaatcaac aagcgtattt tgagtcctaa tggtaaagat  420
ctatctgagt ttggagagtg gccttggcag ggagctgtat tgaaagtcga aggcaaagtt  480
aacatcttcc agtgtggtgc cgttcttata gacagttatc acttacttac tgtagcccat  540
tgcgtttaca agtttacgct tgaaaatgct tttcccttga aagtaagact gggagaatgg  600
gacacccaaa ataccaatga gttcttgaag catgaagatt atgaagtgga aaaaatttac  660
attcatccta aatatgatga tgaaaggaaa aacttgtggg acgacattgc tattttgaaa  720
ctgaaagctg aagtttcctt tggtcctcac attgacacta tctgcttacc aaataatcaa  780
gaacattttg caggtgttca gtgtgtggtt actggttggg gaaagaatgc ctacaaaaat  840
ggttcgtact ccaatgtatt aagggaagtc cacgtgcctg ttattactaa cgataggtgt  900
caggagcttc tcagaaaaac taggttaagt gaatggtacg tcttgtacga aaactttatc  960
tgtgctggtg gagaaagtaa cgctgactct tgcaagggag atggaggtgg tcctttaacg  1020
tgctggagga aagatggtac ttatggacta gcaggtctgg tatcatgggg aattaactgt  1080
ggtagtccta atgtgcctgg tgtttatgtc agagttgcaa attatcttga ctggattacc  1140
aagattaccg gtcgtccaat ttctgattac tggccacgtt cgtaa                  1185

SEQ ID NO: 28          moltype = DNA  length = 1242
FEATURE                Location/Qualifiers
source                 1..1242
                       mol_type = genomic DNA
                       organism = Tachypleus tridentatus
SEQUENCE: 28
atggggatcc ttcccagccc tgggatgcct gcgctgctct ccctcgtgag ccttctctcc  60
gtgctgctga tgggttgcgt agctgaaacc ggtcaagacg atgacgggcc agtctggggt  120
ggttcaagca acgataatga tgatggtggt attagcagtc gcgttggcaa cccccaatct  180
ggttttggta actgtgagtg tgtaccttat tacttgtgta aggataataa tattatcatt  240
gatggttctg gcttactcga ccctagaaaa aaaccagtag cctccaaaga acctaaattg  300
tctgcacgcc taggtccaga aggtccaagt gggtgtggtc cttttcacgt atgctgtatt  360
gcaccagaaa catccacagt aaaaccatat actcatcaat gtggcttcag aaacgtcaat  420
ggaatcaaca agcgtatttt gagtcctaat ggtaaagatc tatctgagtt tggagagtgg  480
ccttggcagg gagctgtatt gaaagtcgaa ggcaaagtta acatcttcca gtgtggtgcc  540
gttcttatag acagttatca cttacttact gtagcccatt gcgtttacaa gtttacgctt  600
gaaaatgctt ttcccttgaa agtaagactg ggagaatggg acacccaaaa taccaatgag  660
ttcttgaagc atgaagatta tgaagtggaa aaaatttaca ttcatcctaa atatgatgat  720
gaaaggaaaa acttgtggga cgacattgct attttgaaac tgaaagctga agtttccttt  780
ggtcctcaca ttgacactat ctgcttacca aataatcaag aacattttgc aggtgttcag  840
tgtgtggtta ctggttgggg aaagaatgcc tacaaaaatg gttcgtactc caatgtatta  900
```

```
agggaagtcc acgtgcctgt tattactaac gataggtgtc aggagcttct cagaaaaact  960
aggttaagtg aatggtacgt cttgtacgaa aactttatct gtgctggtgg agaaagtaac  1020
gctgactctt gcaagggaga tggaggtggt cctttaacgt gctggaggaa agatggtact  1080
tatggactag caggtctggt atcatgggga attaactgtg gtagtcctaa tgtgcctggt  1140
gtttatgtca gagttgcaaa ttatcttgac tggattacca agattaccgg tcgtccaatt  1200
tctgattact ggccacgttc gcaccaccat caccatcact aa                     1242

SEQ ID NO: 29          moltype = DNA  length = 1185
FEATURE                Location/Qualifiers
source                 1..1185
                       mol_type = genomic DNA
                       organism = Limulus polyphemus
SEQUENCE: 29
atgaaagtgt tgttgctgat gactttcctt tttgaaacgg cgttggctta tccacaagac  60
gatgacggac caatctgggg tggttcaaac agcgataacg atgacgggag tattaatagt  120
cgagttgaca accccccactc cggttttggt aattgcgagt gtgtacctta ttacgtgtgt  180
aaggacgaca atatcatcac tgatggttct ggcgtactcg accctaggaa aaaaccagta  240
ccctccaaag aacccgattt gtttgcccac ctgagtccag aaggccgaag agggtgtggt  300
aactttcatg tatgttgtat tgcaccaaca acatccaccg taaaaccata tactcgtcaa  360
tgtggcttca ggaaagtcaa tggcatcaac aagcgtattt tgagtcctaa tggtaaaaat  420
ctgtccgagt ttggagagtg gccttggcag ggagctgtcc taaaagtcga aggcaaagtt  480
aacatcttcc agtgtggtgc cgttcttata gacagtttc acttgcttac tgtagcccat  540
tgcgtttaca gatttacgct tgaaaatgct tttcctttga aagtgcgact gggagaatgg  600
gatacccaaa atactaatga gttcttgaag catgaagatt atgaagtgga aaaaatttcc  660
atccactcta aatataatca tgaaaggaaa aacttgtggg acgacatcgc tattttgaaa  720
ctgaaagtgg aagtttcctt tggtcctcat attgacacca tctgtttacc aaaatatcaa  780
gaaaagtttg aaggtgttca gtgtgtggtt actggttggg gaaagaatgc ctacaaaaat  840
ggttcgtaca ccaatgtctt aagaaaagcc catgttcctg ttattagtaa cgataaatgt  900
cagcagcttc tgagaaaaac taggttaagt aagtggttca tcttgtatga aaactttatc  960
tgtgctggtg gagaaagtaa cgccgattct tgcaaggggg atggaggtgg ccccttagcc  1020
tgctggagaa aagacggtac ctatggattg gcaggcctgg tatcgtgggg aattggctgc  1080
ggtagtccta atgtccctgg tgtttatgtc agagttacaa attatcttga ctggattaca  1140
gaagttactg gtcgaccgat ctcggagtac tggccacgtt cttaa                  1185

SEQ ID NO: 30          moltype = DNA  length = 1191
FEATURE                Location/Qualifiers
source                 1..1191
                       mol_type = genomic DNA
                       organism = Limulus polyphemus
SEQUENCE: 30
atgaaagtgt tgttgttgat gactttcctt tttggaacgg cgttggctta tccacaagac  60
gatgacggac cagtctgggg tggttcaaac aacgatgacg atgacgatga cgggggtatt  120
agtagtcgag ttggcaaccc acaatctagt tttggtaact gcgagtgtgt accttattac  180
ttgtgtaagg acaataatat tatcactgat ggttctggcg tactcgaccc taggaaaaaa  240
ccagtaccct ccaaagaacc cggtttgtct gcccgccttg gtccagaagg tccaagtggg  300
tgtggtccgt ttcacgtatg ttgcactgcg ccaacaacat caacagtaaa accatatact  360
catcaatgtg gcttcaggaa cgtcaatggg atcaacaagc gtattttgag tcctaatggt  420
aaagatctat ctgagtttgg agagtggcct tggcagggtg ctgtcctaaa agtcgaaggc  480
aaagttaaca tcttccagtg tggtgccgtt cttatagaca gttttcactt gcttactgta  540
gcccactgcg tttacagatt tacgcttgca aatgcttttc ctttgaaagt gcgactggga  600
gaatgggata cccagaatac tgatgagttc ttgaagcatg aagattatga agtggaaaaa  660
atttacatcc actctaaata taatcatgaa aggaaaaact tgtgggacga catcgctatt  720
ttgaaactga aagtggaagt ttcctttggt cctcatattg acaccatctg tttaccaaat  780
taccaagaaa attttgaagg tgttcagtgt gtggttactg gttggggaaa gaatgcctac  840
aaaaatggta cgtactccaa tgtcttaaga gaagtccatg tgcctgttat tagtaacgat  900
aaatgtgagc agcttctgaa agaaactagg ctaagtaagt ggttcgtctt gtatgaaaac  960
tttacctgtg ctggtggaga aagtaacgcc gattcttgca agggagatgg aggtggcccc  1020
ttagcctgct ggagaaaaga tggtacttat gcattggcag gcctggtatc gtggggaatt  1080
gactgcggta gtcctaatgt gcctggtgtt tatgtcagag ttgcaaaata tcttgattgg  1140
attgcccaaa ttactggtcg tccggtcacg gattactggc cacggtctta a          1191

SEQ ID NO: 31          moltype = DNA  length = 1248
FEATURE                Location/Qualifiers
source                 1..1248
                       mol_type = genomic DNA
                       organism = Limulus polyphemus
SEQUENCE: 31
atggggatcc ttcccagccc tgggatgcct gcgctgctct ccctcgtgag ccttctctcc  60
gtgctgctga tgggttgcgt agctgaaacc ggtcaagacg atgacggacc agtctggggt  120
ggttcaaaca acgatgacga tgacgatgac gggggtatta gtagtcgagt tggcaaccca  180
caatctagtt ttggtaactg cgagtgtgta ccttattact tgtgtaagga caataatatt  240
atcactgatg gttctggcgt actcgaccct aggaaaaaac cagtaccctc caaagaaccc  300
ggtttgtctg cccgccttgg tccagaaggt ccaagtgggt gtggtccgtt tcacgtatgt  360
tgcactgcgc caacaacatc aacagtaaaa ccatatactc atcaatgtgg cttcaggaac  420
gtcaatggga tcaacaagcg tattttgagt cctaatggta aagatctatc tgagtttgga  480
gagtggcctt ggcagggtgc tgtcctaaaa gtcgaaggca aagttaacat cttccagtgt  540
ggtgccgttc ttatagacag ttttcacttg cttactgtag cccactgcgt ttacagattt  600
acgcttgcaa atgcttttcc tttgaaagtg cgactgggag aatgggatac ccagaatact  660
gatgagttct tgaagcatga agattatgaa gtggaaaaaa tttacatcca ctctaaatat  720
```

-continued

```
aatcatgaaa ggaaaaactt gtgggacgac atcgctattt tgaaactgaa agtggaagtt  780
tcctttggtc ctcatattga caccatctgt ttaccaaatt accaagaaaa ttttgaaggt  840
gttcagtgtg tggttactgg ttggggaaag aatgcctaca aaaatggtac gtactccaat  900
gtcttaagag aagtccatgt gcctgttatt agtaacgata aatgtgagca gcttctgaaa  960
gaaactaggc taagtaagtg gttcgtcttg tatgaaaact ttacctgtgc tggtggagaa  1020
agtaacgccg attcttgcaa gggagatgga ggtggcccct tagcctgctg gagaaaagat  1080
ggtacttatg cattggcagg cctggtatcg tggggaattg actgcggtag tcctaatgtg  1140
cctggtgttt atgtcagagt tgcaaaatat cttgattgga ttgcccaaat tactggtcgt  1200
ccggtcacgg attactggcc acggtctcac caccatcacc atcactaa              1248
```

```
SEQ ID NO: 32          moltype = AA  length = 409
FEATURE                Location/Qualifiers
source                 1..409
                       mol_type = protein
                       organism = Limulus polyphemus
SEQUENCE: 32
MGILPSPGMP ALLSLVSLLS VLLMGCVAET GQDDDGPVWG GSNNDDDDDD GGISSRVGNP  60
QSSFGNCECV PYYLCKDNNI ITDGSGVLDP RKKPVPSKEP GLSARLGPEG PSGCGPFHVC  120
CTAPTTSTVK PYTHQCGFRN VNGINKRILS PNGKDLSEFG EWPWQGAVLK VEGKVNIFQC  180
GAVLIDSFHL LTVAHCVYRF TLANAFPLKV RLGEWDTQNT DEFLKHEDYE VEKIYIHSKY  240
NHERKNLWDD IAILKLKVEV SFGPHIDTIC LPNYQENFEG VQCVVTGWGK NAYKNGTYSN  300
VLREVHVPVI SNDKCEQLLK ETRLSKWFVL YENFTCAGGE SNADSCKGDG GGPLACWRKD  360
GTYALAGLVS WGIDCGSPNV PGVYVRVAKY LDWIAQITGR PVTDYWPRS              409
```

```
SEQ ID NO: 33          moltype = AA  length = 381
FEATURE                Location/Qualifiers
source                 1..381
                       mol_type = protein
                       organism = Limulus polyphemus
SEQUENCE: 33
ETGQDDDGPV WGGSNNDDDD DDGGISSRVG NPQSSFGNCE CVPYYLCKDN NIITDGSGVL  60
DPRKKPVPSK EPGLSARLGP EGPSGCGPFH VCCTAPTTST VKPYTHQCGF RNVNGINKRI  120
LSPNGKDLSE FGEWPWQGAV LKVEGKVNIF QCGAVLIDSF HLLTVAHCVY RFTLANAFPL  180
KVRLGEWDTQ NTDEFLKHED YEVEKIYIHS KYNHERKNLW DDIAILKLKV EVSFGPHIDT  240
ICLPNYQENF EGVQCVVTGW GKNAYKNGTY SNVLREVHVP VISNDKCEQL LKETRLSKWF  300
VLYENFTCAG GESNADSCKG DGGGPLACWR KDGTYALAGL VSWGIDCGSP NVPGVYVRVA  360
KYLDWIAQIT GRPVTDYWPR S                                            381
```

```
SEQ ID NO: 34          moltype = DNA  length = 1230
FEATURE                Location/Qualifiers
source                 1..1230
                       mol_type = genomic DNA
                       organism = Limulus polyphemus
SEQUENCE: 34
atgggcatcc tgccatcccc tggcatgcca gccctgctga gcctggtgtc tctgctgtcc  60
gtgctgctga tgggatgcgt ggctgagacc ggccaggacg atgacggccc cgtgtggggc  120
ggcagcaaca atgatgacga tgacgatgac ggaggaatct ccagcagggt gggaaaccct  180
cagtcttcct ttggcaattg cgagtgcgtg ccatactatc tgtgcaagga taacaatatc  240
atcaccgacg gcagcggcgt gctggatcca agaaagaagc cagtgccctc caaggagcct  300
ggcctgagcg cccgcctggg ccctgagggc ccatctggct gtggcccctt ccacgtgtgc  360
tgtacagctc ctaccacatc caccgtgaag ccatacacac atcagtgcgg ctttaggaac  420
gtgaatggca tcaacaagcg gatcctgtct cccaatggca aggacctgtc cgagttcgga  480
gagtggcctt ggcagggagc cgtgctgaag gtggagggca aggtgaacat cttccagtgt  540
ggcgccgtgc tgatcgattc ttttcacctg ctgaccgtgg ctcattgcgt gtacaggttc  600
acactggcca acgcttttcc tctgaaggtg cggctgggcg agtgggatac ccagaataca  660
gacgagttcc tgaagcacga ggactatgag gtggagaaaa tctacatcca cagcaagtat  720
aaccatgagc ggaagaatct gtgggatgac atcgccatcc tgaagctgaa ggtggaggtg  780
tctttcggcc cccatatcga taccatctgt ctgcctaact accaggagaa ttttgaggga  840
gtgcagtgcg tggtgaccgg ctggggcaag aacgcttaca agaatggcac atattccaac  900
gtgctgaggg aggtgcatgt gcctgtgatc agcaatgaca agtgtgagca gctgctgaag  960
gagacccggc tgtctaagtg gttcgtgctg tacgagaact ttacatgcgc cggcggcgag  1020
agcaatgctg attcttgtaa gggcgacgga ggaggaccac tggcttgctg gagaaaggac  1080
ggcacatatg ccctggctgg actggtgagc tggggaatcg attgcggctc tcccaacgtg  1140
cctggcgtgt acgtgcgcgt ggccaagtat ctggactgga tcgctcagat caccggcaga  1200
ccagtgacag attattggcc ccgctcctga                                  1230
```

```
SEQ ID NO: 35          moltype = AA  length = 376
FEATURE                Location/Qualifiers
source                 1..376
                       mol_type = protein
                       organism = Tachypleus tridentatus
SEQUENCE: 35
QDDDGPVWGG SSNDNDDGGI SSRVGNPQSG FGNCECVPYY LCKDNNIIID GSGLLDPRKK  60
PVASKEPKLS AALGPEGPSG CGPFHVCCIA PETSTVKPYT HQCGFRNVNG INKRILSPNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVSNYLDW  360
ITKITGRPIS DYWPRS                                                  376
```

```
SEQ ID NO: 36          moltype = AA  length = 376
FEATURE                Location/Qualifiers
source                 1..376
                       mol_type = protein
                       organism = Tachypleus tridentatus
SEQUENCE: 36
QDDDGPVWGG SSNDNDDGGI SSRVGNPQSG FGNCECVPYY LCKDNNIIID GSGLLDPRKK  60
PVASKEPKLS AELGPEGPSG CGPFHVCCIA PETSTVKPYT HQCGFRNVNG INKRILSPNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVSNYLDW  360
ITKITGRPIS DYWPRS                                                  376

SEQ ID NO: 37          moltype = AA  length = 376
FEATURE                Location/Qualifiers
source                 1..376
                       mol_type = protein
                       organism = Tachypleus tridentatus
SEQUENCE: 37
QDDDGPVWGG SSNDNDDGGI SSRVGNPQSG FGNCECVPYY LCKDNNIIID GSGLLDPRKK  60
PVASKEPKLS APLGPEGPSG CGPFHVCCIA PETSTVKPYT HQCGFRNVNG INKRILSPNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVSNYLDW  360
ITKITGRPIS DYWPRS                                                  376

SEQ ID NO: 38          moltype = AA  length = 376
FEATURE                Location/Qualifiers
source                 1..376
                       mol_type = protein
                       organism = Tachypleus tridentatus
SEQUENCE: 38
QDDDGPVWGG SSNDNDDGGI SSRVGNPQSG FGNCECVPYY LCKDNNIIID GSGLLDPRKK  60
PVASKEPKLS ARAGPEGPSG CGPFHVCCIA PETSTVKPYT HQCGFRNVNG INKRILSPNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVSNYLDW  360
ITKITGRPIS DYWPRS                                                  376

SEQ ID NO: 39          moltype = AA  length = 376
FEATURE                Location/Qualifiers
source                 1..376
                       mol_type = protein
                       organism = Tachypleus tridentatus
SEQUENCE: 39
QDDDGPVWGG SSNDNDDGGI SSRVGNPQSG FGNCECVPYY LCKDNNIIID GSGLLDPRKK  60
PVASKEPPLS ARLGPEGPSG CGPFHVCCIA PETSTVKPYT HQCGFRNVNG INKRILSPNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVSNYLDW  360
ITKITGRPIS DYWPRS                                                  376

SEQ ID NO: 40          moltype = AA  length = 376
FEATURE                Location/Qualifiers
source                 1..376
                       mol_type = protein
                       organism = Tachypleus tridentatus
SEQUENCE: 40
QDDDGPVWGG SSNDNDDGGI SSRVGNPQSG FGNCECVPYY LCKDNNIIID GSGLLDPRKK  60
PVASKEPKLS ARLGPEGPSG CGPFHVCCIA PETSTVKPYT HQCGFRNVNG INKRILSANG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVSNYLDW  360
ITKITGRPIS DYWPRS                                                  376

SEQ ID NO: 41          moltype = AA  length = 376
FEATURE                Location/Qualifiers
source                 1..376
                       mol_type = protein
                       organism = Tachypleus tridentatus
SEQUENCE: 41
QDDDGPVWGG SSNDNDDGGI SSRVGNPQSG FGNCECVPYY LCKDNNIIID GSGLLDPRKK  60
PVASKEPKLS ARLGPEGPSG CGPFHVCCIA PETSTVKPYT HQCGFRNVNG INKRILSVNG  120
```

-continued

```
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVSNYLDW  360
ITKITGRPIS DYWPRS                                                 376

SEQ ID NO: 42          moltype = AA  length = 376
FEATURE                Location/Qualifiers
source                 1..376
                       mol_type = protein
                       organism = Tachypleus tridentatus
SEQUENCE: 42
QDDDGPVWGG SSNDNDDGGI SSRVGNPQSG FGNCECVPYY LCKDNNIIID GSGLLDPRKK  60
PVASKEPKLS ARLGPEGPSG CGPFHVCCIA PETSTVKPYT HQCGFRNVNG INKRILSGNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVSNYLDW  360
ITKITGRPIS DYWPRS                                                 376

SEQ ID NO: 43          moltype = AA  length = 376
FEATURE                Location/Qualifiers
source                 1..376
                       mol_type = protein
                       organism = Tachypleus tridentatus
SEQUENCE: 43
QDDDGPVWGG SSNDNDDGGI SSRVGNPQSG FGNCECVPYY LCKDNNIIID GSGLLDPRKK  60
PVASKEPKLS AALGPEGPSG CGPFHVCCIA PETSTVKPYT HQCGFRNVNG INKRILSPNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVANYLDW  360
ITKITGRPIS DYWPRS                                                 376

SEQ ID NO: 44          moltype = AA  length = 376
FEATURE                Location/Qualifiers
source                 1..376
                       mol_type = protein
                       organism = Tachypleus tridentatus
SEQUENCE: 44
QDDDGPVWGG SSNDNDDGGI SSRVGNPQSG FGNCECVPYY LCKDNNIIID GSGLLDPRKK  60
PVASKEPKLS AELGPEGPSG CGPFHVCCIA PETSTVKPYT HQCGFRNVNG INKRILSPNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVANYLDW  360
ITKITGRPIS DYWPRS                                                 376

SEQ ID NO: 45          moltype = AA  length = 376
FEATURE                Location/Qualifiers
source                 1..376
                       mol_type = protein
                       organism = Tachypleus tridentatus
SEQUENCE: 45
QDDDGPVWGG SSNDNDDGGI SSRVGNPQSG FGNCECVPYY LCKDNNIIID GSGLLDPRKK  60
PVASKEPKLS APLGPEGPSG CGPFHVCCIA PETSTVKPYT HQCGFRNVNG INKRILSPNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVANYLDW  360
ITKITGRPIS DYWPRS                                                 376

SEQ ID NO: 46          moltype = AA  length = 376
FEATURE                Location/Qualifiers
source                 1..376
                       mol_type = protein
                       organism = Tachypleus tridentatus
SEQUENCE: 46
QDDDGPVWGG SSNDNDDGGI SSRVGNPQSG FGNCECVPYY LCKDNNIIID GSGLLDPRKK  60
PVASKEPKLS ARAGPEGPSG CGPFHVCCIA PETSTVKPYT HQCGFRNVNG INKRILSPNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVANYLDW  360
ITKITGRPIS DYWPRS                                                 376

SEQ ID NO: 47          moltype = AA  length = 376
FEATURE                Location/Qualifiers
```

```
source                 1..376
                       mol_type = protein
                       organism = Tachypleus tridentatus
SEQUENCE: 47
QDDDGPVWGG SSNDNDDGGI SSRVGNPQSG FGNCECVPYY LCKDNNIIID GSGLLDPRKK  60
PVASKEPPLS ARLGPEGPSG CGPFHVCCIA PETSTVKPYT HQCGFRNVNG INKRILSPNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVANYLDW  360
ITKITGRPIS DYWPRS                                                 376

SEQ ID NO: 48          moltype = AA  length = 376
FEATURE                Location/Qualifiers
source                 1..376
                       mol_type = protein
                       organism = Tachypleus tridentatus
SEQUENCE: 48
QDDDGPVWGG SSNDNDDGGI SSRVGNPQSG FGNCECVPYY LCKDNNIIID GSGLLDPRKK  60
PVASKEPKLS ARLGPEGPSG CGPFHVCCIA PETSTVKPYT HQCGFRNVNG INKRILSANG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVANYLDW  360
ITKITGRPIS DYWPRS                                                 376

SEQ ID NO: 49          moltype = AA  length = 376
FEATURE                Location/Qualifiers
source                 1..376
                       mol_type = protein
                       organism = Tachypleus tridentatus
SEQUENCE: 49
QDDDGPVWGG SSNDNDDGGI SSRVGNPQSG FGNCECVPYY LCKDNNIIID GSGLLDPRKK  60
PVASKEPKLS ARLGPEGPSG CGPFHVCCIA PETSTVKPYT HQCGFRNVNG INKRILSVNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVANYLDW  360
ITKITGRPIS DYWPRS                                                 376

SEQ ID NO: 50          moltype = AA  length = 376
FEATURE                Location/Qualifiers
source                 1..376
                       mol_type = protein
                       organism = Tachypleus tridentatus
SEQUENCE: 50
QDDDGPVWGG SSNDNDDGGI SSRVGNPQSG FGNCECVPYY LCKDNNIIID GSGLLDPRKK  60
PVASKEPKLS ARLGPEGPSG CGPFHVCCIA PETSTVKPYT HQCGFRNVNG INKRILSGNG  120
KDLSEFGEWP WQGAVLKVEG KVNIFQCGAV LIDSYHLLTV AHCVYKFTLE NAFPLKVRLG  180
EWDTQNTNEF LKHEDYEVEK IYIHPKYDDE RKNLWDDIAI LKLKAEVSFG PHIDTICLPN  240
NQEHFAGVQC VVTGWGKNAY KNGSYSNVLR EVHVPVITND RCQELLRKTR LSEWYVLYEN  300
FICAGGESNA DSCKGDGGGP LTCWRKDGTY GLAGLVSWGI NCGSPNVPGV YVRVANYLDW  360
ITKITGRPIS DYWPRS                                                 376

SEQ ID NO: 51          moltype = AA  length = 376
FEATURE                Location/Qualifiers
source                 1..376
                       mol_type = protein
                       organism = Limulus polyphemus
SEQUENCE: 51
QDDDGPIWGG SNSDNDDGSI NSRVDNPHSG FGNCECVPYY VCKDDNIITD GSGVLDPRKK  60
PVPSKEPDLF AALSPEGRRG CGNFHVCCIA PTTSTVKPYT RQCGFRKVNG INKRILSPNG  120
KNLSEFGEWP WQGAVLKVEG KVNIFQCGAV LIDSFHLLTV AHCVYRFTLE NAFPLKVRLG  180
EWDTQNTNEF LKHEDYEVEK ISIHSKYNHE RKNLWDDIAI LKLKVEVSFG PHIDTICLPK  240
YQEKFEGVQC VVTGWGKNAY KNGSYTNVLR KAHVPVISND KCQQLLRKTR LSKWFILYEN  300
FICAGGESNA DSCKGDGGGP LACWRKDGTY GLAGLVSWGI GCGSPNVPGV YVRVTNYLDW  360
ITEVTGRPIS EYWPRS                                                 376

SEQ ID NO: 52          moltype = AA  length = 376
FEATURE                Location/Qualifiers
source                 1..376
                       mol_type = protein
                       organism = Limulus polyphemus
SEQUENCE: 52
QDDDGPIWGG SNSDNDDGSI NSRVDNPHSG FGNCECVPYY VCKDDNIITD GSGVLDPRKK  60
PVPSKEPDLF AELSPEGRRG CGNFHVCCIA PTTSTVKPYT RQCGFRKVNG INKRILSPNG  120
KNLSEFGEWP WQGAVLKVEG KVNIFQCGAV LIDSFHLLTV AHCVYRFTLE NAFPLKVRLG  180
EWDTQNTNEF LKHEDYEVEK ISIHSKYNHE RKNLWDDIAI LKLKVEVSFG PHIDTICLPK  240
YQEKFEGVQC VVTGWGKNAY KNGSYTNVLR KAHVPVISND KCQQLLRKTR LSKWFILYEN  300
```

```
FICAGGESNA DSCKGDGGGP LACWRKDGTY GLAGLVSWGI GCGSPNVPGV YVRVTNYLDW  360
ITEVTGRPIS EYWPRS                                                  376

SEQ ID NO: 53          moltype = AA  length = 376
FEATURE                Location/Qualifiers
source                 1..376
                       mol_type = protein
                       organism = Limulus polyphemus
SEQUENCE: 53
QDDDGPIWGG SNSDNDDGSI NSRVDNPHSG FGNCECVPYY VCKDDNIITD GSGVLDPRKK  60
PVPSKEPDLF APLSPEGRRG CGNFHVCCIA PTTSTVKPYT RQCGFRKVNG INKRILSPNG  120
KNLSEFGEWP WQGAVLKVEG KVNIFQCGAV LIDSFHLLTV AHCVYRFTLE NAFPLKVRLG  180
EWDTQNTNEF LKHEDYEVEK ISIHSKYNHE RKNLWDDIAI LKLKVEVSFG PHIDTICLPK  240
YQEKFEGVQC VVTGWGKNAY KNGSYTNVLR KAHVPVISND KCQQLLRKTR LSKWFILYEN  300
FICAGGESNA DSCKGDGGGP LACWRKDGTY GLAGLVSWGI GCGSPNVPGV YVRVTNYLDW  360
ITEVTGRPIS EYWPRS                                                  376

SEQ ID NO: 54          moltype = AA  length = 376
FEATURE                Location/Qualifiers
source                 1..376
                       mol_type = protein
                       organism = Limulus polyphemus
SEQUENCE: 54
QDDDGPIWGG SNSDNDDGSI NSRVDNPHSG FGNCECVPYY VCKDDNIITD GSGVLDPRKK  60
PVPSKEPDLF AHASPEGRRG CGNFHVCCIA PTTSTVKPYT RQCGFRKVNG INKRILSPNG  120
KNLSEFGEWP WQGAVLKVEG KVNIFQCGAV LIDSFHLLTV AHCVYRFTLE NAFPLKVRLG  180
EWDTQNTNEF LKHEDYEVEK ISIHSKYNHE RKNLWDDIAI LKLKVEVSFG PHIDTICLPK  240
YQEKFEGVQC VVTGWGKNAY KNGSYTNVLR KAHVPVISND KCQQLLRKTR LSKWFILYEN  300
FICAGGESNA DSCKGDGGGP LACWRKDGTY GLAGLVSWGI GCGSPNVPGV YVRVTNYLDW  360
ITEVTGRPIS EYWPRS                                                  376

SEQ ID NO: 55          moltype = AA  length = 376
FEATURE                Location/Qualifiers
source                 1..376
                       mol_type = protein
                       organism = Limulus polyphemus
SEQUENCE: 55
QDDDGPIWGG SNSDNDDGSI NSRVDNPHSG FGNCECVPYY VCKDDNIITD GSGVLDPRKK  60
PVPSKEPPLF AHLSPEGRRG CGNFHVCCIA PTTSTVKPYT RQCGFRKVNG INKRILSPNG  120
KNLSEFGEWP WQGAVLKVEG KVNIFQCGAV LIDSFHLLTV AHCVYRFTLE NAFPLKVRLG  180
EWDTQNTNEF LKHEDYEVEK ISIHSKYNHE RKNLWDDIAI LKLKVEVSFG PHIDTICLPK  240
YQEKFEGVQC VVTGWGKNAY KNGSYTNVLR KAHVPVISND KCQQLLRKTR LSKWFILYEN  300
FICAGGESNA DSCKGDGGGP LACWRKDGTY GLAGLVSWGI GCGSPNVPGV YVRVTNYLDW  360
ITEVTGRPIS EYWPRS                                                  376

SEQ ID NO: 56          moltype = AA  length = 376
FEATURE                Location/Qualifiers
source                 1..376
                       mol_type = protein
                       organism = Limulus polyphemus
SEQUENCE: 56
QDDDGPIWGG SNSDNDDGSI NSRVDNPHSG FGNCECVPYY VCKDDNIITD GSGVLDPRKK  60
PVPSKEPDLF AHLSPEGRRG CGNFHVCCIA PTTSTVKPYT RQCGFRKVNG INKRILSANG  120
KNLSEFGEWP WQGAVLKVEG KVNIFQCGAV LIDSFHLLTV AHCVYRFTLE NAFPLKVRLG  180
EWDTQNTNEF LKHEDYEVEK ISIHSKYNHE RKNLWDDIAI LKLKVEVSFG PHIDTICLPK  240
YQEKFEGVQC VVTGWGKNAY KNGSYTNVLR KAHVPVISND KCQQLLRKTR LSKWFILYEN  300
FICAGGESNA DSCKGDGGGP LACWRKDGTY GLAGLVSWGI GCGSPNVPGV YVRVTNYLDW  360
ITEVTGRPIS EYWPRS                                                  376

SEQ ID NO: 57          moltype = AA  length = 376
FEATURE                Location/Qualifiers
source                 1..376
                       mol_type = protein
                       organism = Limulus polyphemus
SEQUENCE: 57
QDDDGPIWGG SNSDNDDGSI NSRVDNPHSG FGNCECVPYY VCKDDNIITD GSGVLDPRKK  60
PVPSKEPDLF AHLSPEGRRG CGNFHVCCIA PTTSTVKPYT RQCGFRKVNG INKRILSVNG  120
KNLSEFGEWP WQGAVLKVEG KVNIFQCGAV LIDSFHLLTV AHCVYRFTLE NAFPLKVRLG  180
EWDTQNTNEF LKHEDYEVEK ISIHSKYNHE RKNLWDDIAI LKLKVEVSFG PHIDTICLPK  240
YQEKFEGVQC VVTGWGKNAY KNGSYTNVLR KAHVPVISND KCQQLLRKTR LSKWFILYEN  300
FICAGGESNA DSCKGDGGGP LACWRKDGTY GLAGLVSWGI GCGSPNVPGV YVRVTNYLDW  360
ITEVTGRPIS EYWPRS                                                  376

SEQ ID NO: 58          moltype = AA  length = 376
FEATURE                Location/Qualifiers
source                 1..376
                       mol_type = protein
                       organism = Limulus polyphemus
```

```
SEQUENCE: 58
QDDDGPIWGG SNSDNDDGSI NSRVDNPHSG FGNCECVPYY VCKDDNIITD GSGVLDPRKK  60
PVPSKEPDLF AHLSPEGRRG CGNFHVCCIA PTTSTVKPYT RQCGFRKVNG INKRILSGNG  120
KNLSEFGEWP WQGAVLKVEG KVNIFQCGAV LIDSFHLLTV AHCVYRFTLE NAFPLKVRLG  180
EWDTQNTNEF LKHEDYEVEK ISIHSKYNHE RKNLWDDIAI LKLKVEVSFG PHIDTICLPK  240
YQEKFEGVQC VVTGWGKNAY KNGSYTNVLR KAHVPVISND KCQQLLRKTR LSKWFILYEN  300
FICAGGESNA DSCKGDGGGP LACWRKDGTY GLAGLVSWGI GCGSPNVPGV YVRVTNYLDW  360
ITEVTGRPIS EYWPRS                                                376

SEQ ID NO: 59          moltype = AA  length = 378
FEATURE                Location/Qualifiers
source                 1..378
                       mol_type = protein
                       organism = Limulus polyphemus
SEQUENCE: 59
QDDDGPVWGG SNNDDDDDDG GISSRVGNPQ SSFGNCECVP YYLCKDNNII TDGSGVLDPR  60
KKPVPSKEPG LSAALGPEGP SGCGPFHVCC TAPTTSTVKP YTHQCGFRNV NGINKRILSP  120
NGKDLSEFGE WPWQGAVLKV EGKVNIFQCG AVLIDSFHLL TVAHCVYRFT LANAFPLKVR  180
LGEWDTQNTD EFLKHEDYEV EKIYIHSKYN HERKNLWDDI AILKLKVEVS FGPHIDTICL  240
PNYQENFEGV QCVVTGWGKN AYKNGTYSNV LREVHVPVIS NDKCEQLLKE TRLSKWFVLY  300
ENFTCAGGES NADSCKGDGG GPLACWRKDG TYALAGLVSW GIDCGSPNVP GVYVRVAKYL  360
DWIAQITGRP VTDYWPRS                                              378

SEQ ID NO: 60          moltype = AA  length = 378
FEATURE                Location/Qualifiers
source                 1..378
                       mol_type = protein
                       organism = Limulus polyphemus
SEQUENCE: 60
QDDDGPVWGG SNNDDDDDDG GISSRVGNPQ SSFGNCECVP YYLCKDNNII TDGSGVLDPR  60
KKPVPSKEPG LSAELGPEGP SGCGPFHVCC TAPTTSTVKP YTHQCGFRNV NGINKRILSP  120
NGKDLSEFGE WPWQGAVLKV EGKVNIFQCG AVLIDSFHLL TVAHCVYRFT LANAFPLKVR  180
LGEWDTQNTD EFLKHEDYEV EKIYIHSKYN HERKNLWDDI AILKLKVEVS FGPHIDTICL  240
PNYQENFEGV QCVVTGWGKN AYKNGTYSNV LREVHVPVIS NDKCEQLLKE TRLSKWFVLY  300
ENFTCAGGES NADSCKGDGG GPLACWRKDG TYALAGLVSW GIDCGSPNVP GVYVRVAKYL  360
DWIAQITGRP VTDYWPRS                                              378

SEQ ID NO: 61          moltype = AA  length = 378
FEATURE                Location/Qualifiers
source                 1..378
                       mol_type = protein
                       organism = Limulus polyphemus
SEQUENCE: 61
QDDDGPVWGG SNNDDDDDDG GISSRVGNPQ SSFGNCECVP YYLCKDNNII TDGSGVLDPR  60
KKPVPSKEPG LSAPLGPEGP SGCGPFHVCC TAPTTSTVKP YTHQCGFRNV NGINKRILSP  120
NGKDLSEFGE WPWQGAVLKV EGKVNIFQCG AVLIDSFHLL TVAHCVYRFT LANAFPLKVR  180
LGEWDTQNTD EFLKHEDYEV EKIYIHSKYN HERKNLWDDI AILKLKVEVS FGPHIDTICL  240
PNYQENFEGV QCVVTGWGKN AYKNGTYSNV LREVHVPVIS NDKCEQLLKE TRLSKWFVLY  300
ENFTCAGGES NADSCKGDGG GPLACWRKDG TYALAGLVSW GIDCGSPNVP GVYVRVAKYL  360
DWIAQITGRP VTDYWPRS                                              378

SEQ ID NO: 62          moltype = AA  length = 378
FEATURE                Location/Qualifiers
source                 1..378
                       mol_type = protein
                       organism = Limulus polyphemus
SEQUENCE: 62
QDDDGPVWGG SNNDDDDDDG GISSRVGNPQ SSFGNCECVP YYLCKDNNII TDGSGVLDPR  60
KKPVPSKEPG LSARAGPEGP SGCGPFHVCC TAPTTSTVKP YTHQCGFRNV NGINKRILSP  120
NGKDLSEFGE WPWQGAVLKV EGKVNIFQCG AVLIDSFHLL TVAHCVYRFT LANAFPLKVR  180
LGEWDTQNTD EFLKHEDYEV EKIYIHSKYN HERKNLWDDI AILKLKVEVS FGPHIDTICL  240
PNYQENFEGV QCVVTGWGKN AYKNGTYSNV LREVHVPVIS NDKCEQLLKE TRLSKWFVLY  300
ENFTCAGGES NADSCKGDGG GPLACWRKDG TYALAGLVSW GIDCGSPNVP GVYVRVAKYL  360
DWIAQITGRP VTDYWPRS                                              378

SEQ ID NO: 63          moltype = AA  length = 378
FEATURE                Location/Qualifiers
source                 1..378
                       mol_type = protein
                       organism = Limulus polyphemus
SEQUENCE: 63
QDDDGPVWGG SNNDDDDDDG GISSRVGNPQ SSFGNCECVP YYLCKDNNII TDGSGVLDPR  60
KKPVPSKEPP LSARLGPEGP SGCGPFHVCC TAPTTSTVKP YTHQCGFRNV NGINKRILSP  120
NGKDLSEFGE WPWQGAVLKV EGKVNIFQCG AVLIDSFHLL TVAHCVYRFT LANAFPLKVR  180
LGEWDTQNTD EFLKHEDYEV EKIYIHSKYN HERKNLWDDI AILKLKVEVS FGPHIDTICL  240
PNYQENFEGV QCVVTGWGKN AYKNGTYSNV LREVHVPVIS NDKCEQLLKE TRLSKWFVLY  300
ENFTCAGGES NADSCKGDGG GPLACWRKDG TYALAGLVSW GIDCGSPNVP GVYVRVAKYL  360
DWIAQITGRP VTDYWPRS                                              378
```

```
SEQ ID NO: 64          moltype = AA  length = 378
FEATURE                Location/Qualifiers
source                 1..378
                       mol_type = protein
                       organism = Limulus polyphemus
SEQUENCE: 64
QDDDGPVWGG SNNDDDDDDG GISSRVGNPQ SSFGNCECVP YYLCKDNNII TDGSGVLDPR  60
KKPVPSKEPG LSARLGPEGP SGCGPFHVCC TAPTTSTVKP YTHQCGFRNV NGINKRILSA  120
NGKDLSEFGE WPWQGAVLKV EGKVNIFQCG AVLIDSFHLL TVAHCVYRFT LANAFPLKVR  180
LGEWDTQNTD EFLKHEDYEV EKIYIHSKYN HERKNLWDDI AILKLKVEVS FGPHIDTICL  240
PNYQENFEGV QCVVTGWGKN AYKNGTYSNV LREVHVPVIS NDKCEQLLKE TRLSKWFVLY  300
ENFTCAGGES NADSCKGDGG GPLACWRKDG TYALAGLVSW GIDCGSPNVP GVYVRVAKYL  360
DWIAQITGRP VTDYWPRS                                                378

SEQ ID NO: 65          moltype = AA  length = 378
FEATURE                Location/Qualifiers
source                 1..378
                       mol_type = protein
                       organism = Limulus polyphemus
SEQUENCE: 65
QDDDGPVWGG SNNDDDDDDG GISSRVGNPQ SSFGNCECVP YYLCKDNNII TDGSGVLDPR  60
KKPVPSKEPG LSARLGPEGP SGCGPFHVCC TAPTTSTVKP YTHQCGFRNV NGINKRILSV  120
NGKDLSEFGE WPWQGAVLKV EGKVNIFQCG AVLIDSFHLL TVAHCVYRFT LANAFPLKVR  180
LGEWDTQNTD EFLKHEDYEV EKIYIHSKYN HERKNLWDDI AILKLKVEVS FGPHIDTICL  240
PNYQENFEGV QCVVTGWGKN AYKNGTYSNV LREVHVPVIS NDKCEQLLKE TRLSKWFVLY  300
ENFTCAGGES NADSCKGDGG GPLACWRKDG TYALAGLVSW GIDCGSPNVP GVYVRVAKYL  360
DWIAQITGRP VTDYWPRS                                                378

SEQ ID NO: 66          moltype = AA  length = 378
FEATURE                Location/Qualifiers
source                 1..378
                       mol_type = protein
                       organism = Limulus polyphemus
SEQUENCE: 66
QDDDGPVWGG SNNDDDDDDG GISSRVGNPQ SSFGNCECVP YYLCKDNNII TDGSGVLDPR  60
KKPVPSKEPG LSARLGPEGP SGCGPFHVCC TAPTTSTVKP YTHQCGFRNV NGINKRILSG  120
NGKDLSEFGE WPWQGAVLKV EGKVNIFQCG AVLIDSFHLL TVAHCVYRFT LANAFPLKVR  180
LGEWDTQNTD EFLKHEDYEV EKIYIHSKYN HERKNLWDDI AILKLKVEVS FGPHIDTICL  240
PNYQENFEGV QCVVTGWGKN AYKNGTYSNV LREVHVPVIS NDKCEQLLKE TRLSKWFVLY  300
ENFTCAGGES NADSCKGDGG GPLACWRKDG TYALAGLVSW GIDCGSPNVP GVYVRVAKYL  360
DWIAQITGRP VTDYWPRS                                                378

SEQ ID NO: 67          moltype = AA  length = 394
FEATURE                Location/Qualifiers
source                 1..394
                       mol_type = protein
                       organism = Carcinoscorpius rotundicauda
SEQUENCE: 67
MKVLLVAFLL GTTLAYPQDD DGPVWGGSSN DDDDDGGISS RIGNPQSGFG NCECVPYYLC  60
KDNNIIIDGS GLLDPRKKPV ASKEPELSAR LGPEGPSGCG PFHVCCIAPE TSTVKPYTHQ  120
CGFRNVNGIN KRILSPNGKD LSEFGEWPWQ GAVLKIEGKV NIFQCGAVLI DSYHLLTVAH  180
CVYKFTLENA FPLKVRLGEW DTQNTNEFLK HEDYEVEKIY IHDKYDHERK NLWDDIAILK  240
LKTEVSFGPH IDTICLPNNE EHFAGVQCVV TGWGKNAYKN GSYSNVLREV HMPVITNDRC  300
QELLRETRLS KWFVLYKNFV CAGGESNTDS CKGDGGGPLA CWRKDGTYGL AGLVSWGIDC  360
GSPNVPGVYV RVANYLDWIT KITGRPISDY WPRS                              394

SEQ ID NO: 68          moltype = AA  length = 377
FEATURE                Location/Qualifiers
source                 1..377
                       mol_type = protein
                       organism = Carcinoscorpius rotundicauda
SEQUENCE: 68
QDDDGPVWGG SSNDDDDDGG ISSRIGNPQS GFGNCECVPY YLCKDNNIII DGSGLLDPRK  60
KPVASKEPEL SARLGPEGPS GCGPFHVCCI APETSTVKPY THQCGFRNVN GINKRILSPN  120
GKDLSEFGEW PWQGAVLKIE GKVNIFQCGA VLIDSYHLLT VAHCVYKFTL ENAFPLKVRL  180
GEWDTQNTNE FLKHEDYEVE KIYIHDKYDH ERKNLWDDIA ILKLKTEVSF GPHIDTICLP  240
NNEEHFAGVQ CVVTGWGKNA YKNGSYSNVL REVHMPVITN DRCQELLRET RLSKWFVLYK  300
NFVCAGGESN TDSCKGDGGG PLACWRKDGT YGLAGLVSWG IDCGSPNVPG VYVRVANYLD  360
WITKITGRPI SDYWPRS                                                 377

SEQ ID NO: 69          moltype = AA  length = 393
FEATURE                Location/Qualifiers
source                 1..393
                       mol_type = protein
                       organism = Tachypleus gigas
SEQUENCE: 69
MKVLLLVAFL LGTTLAYPQD DDGPVWGSND NDDDGGISSR VGNPQSGFGN CVCVPYYLCK  60
DNNIIIDGSG LLDPRKKPIA TKEPELSARL GPEGPSGCGP FHVCCIAPET STVKPYTHQC  120
GFRNVNGINK RILSPNGKDL SEFGEWPWQG AVLKVEGKVN IFQCGAVLID SYHLLTVAHC  180
```

-continued

```
VYKFTLENAF PLKVRLGEWD TQNTNEFLKH EDYEVEKIYV HPKYDHERKN LWDDIAVLKL  240
KAEVSFGPHI DTICLPNNQE HFAGVQCVVT GWGKNAYKNG SYSNVLREVH MPVITNERCQ  300
ELLKKTRLSE WFVLYENFIC AGGESNTDSC KGDGGGPLAC WRKDGTYGLA GLVSWGIDCG  360
SPNVPGVYVR VSNYLDWITK VTGRPISDYW PRS                              393

SEQ ID NO: 70          moltype = AA  length = 375
FEATURE                Location/Qualifiers
source                 1..375
                       mol_type = protein
                       organism = Tachypleus gigas
SEQUENCE: 70
QDDDGPVWGS NDNDDDGGIS SRVGNPQSGF GNCVCVPYYL CKDNNIIIDG SGLLDPRKKP  60
IATKEPELSA RLGPEGPSGC GPFHVCCIAP ETSTVKPYTH QCGFRNVNGI NKRILSPNGK  120
DLSEFGEWPW QGAVLKVEGK VNIFQCGAVL IDSYHLLTVA HCVYKFTLEN AFPLKVRLGE  180
WDTQNTNEFL KHEDYEVEKI YVHPKYDHER KNLWDDIAVL KLKAEVSFGP HIDTICLPNN  240
QEHFAGVQCV VTGWGKNAYK NGSYSNVLRE VHMPVITNER CQELLKKTRL SEWFVLYENF  300
ICAGGESNTD SCKGDGGGPL ACWRKDGTYG LAGLVSWGID CGSPNVPGVY VRVSNYLDWI  360
TKVTGRPISD YWPRS                                                  375

SEQ ID NO: 71          moltype = DNA  length = 1185
FEATURE                Location/Qualifiers
source                 1..1185
                       mol_type = genomic DNA
                       organism = Carcinoscorpius rotundicauda
SEQUENCE: 71
atgaaagtgt tgttggtggc tttccttttg ggaacgacgt tggcttatcc acaagacgat  60
gacgggccag tctggggtgg ttcaagcaac gatgatgatg atgatggtgg tattagcagt  120
cgaattggca acccccaatc tggttttggt aactgcgagt gtgtacctta ttacttgtgt  180
aaggataaca atattatcat tgatggttct ggcttactcg acccaagaaa aaaaccagtt  240
gcctccaaag aacctgaatt gtctgcacgc ctaggtccag aaggtccaag tgggtgtggt  300
ccttttcacg tatgctgtat tgcaccagaa acgtccacgg taaaaccata tactcatcaa  360
tgtggcttca gaaacgtcaa tggaatcaac aagcgtattt tgagtcctaa tggtaaagat  420
ctatctgagt ttggagagtg gccttggcag ggagctgtat tgaaaatcga aggcaaagtt  480
aacatcttcc agtgtggtgc cgttctcata gacagttatc acttacttac tgtagcccat  540
tgcgtttaca agtttacgct tgaaaatgct ttcccttga aagtaagact gggagaatgg  600
gatacccaaa ataccaatga gttcttgaag catgaagatt atgaagtgga aaaaatttac  660
attcatgata aatatgatca tgaaaggaaa aacttgtggg acgacattgc tatttgaaa  720
ctgaaaactg aagtgtcctt tggtcctcac attgacacta tctgcttacc aaataatgaa  780
gaacattttg cgggtgttca gtgtgtggtt actggttggg gaaagaatgc ctacaaaaat  840
ggttcgtact ccaatgtatt aagggaagtc cacatgcctg ttattactaa cgataggtgt  900
caggagcttc tcagagaaac tagattaagt aaatggttcg tcttgtacaa aaactttgtc  960
tgtgctggtg gagaaagtaa caccgattct tgcaagggag atggaggtgg tcctttagcc  1020
tgctggagga aagatggtac ttatggacta gcaggtctgg tatcgtgggg aattgactgt  1080
ggtagtccta atgtgcctgg tgtttatgtc agagttgcaa attatcttga ctggattacc  1140
aagattaccg gtcgtccaat ttctgattac tggccacgtt cgtaa                 1185

SEQ ID NO: 72          moltype = DNA  length = 1182
FEATURE                Location/Qualifiers
source                 1..1182
                       mol_type = genomic DNA
                       organism = Tachypleus gigas
SEQUENCE: 72
atgaaagtgt tgttgttggt ggctttcctt ttgggaacga cgttggctta tccacaagac  60
gacgacgggc cagtctgggg tagcaacgat aatgatgatg atggtggtat tagcagtcgc  120
gttggcaacc cccaatctgg ttttggtaac tgcgtgtgtg taccttatta cttgtgtaag  180
gataataata taatcattga tggttctggc ttactcgacc ctagaaaaaa accaatagcc  240
accaaagaac ctgaattgtc tgcacgccta ggtccagaag gtccaagtgg gtgtggtcct  300
tttcacgtat gctgtattgc accagaaaca tccacagtga aaccatatac tcatcaatgt  360
ggcttcagaa acgtcaatgg aatcaacaag cgtattttga gtcctaatgg taaagatcta  420
tctgagtttg gagagtggcc ttggcaggga gctgtattga aagtcgaagg caaagttaac  480
atcttccagt gtggtgccgt tcttatagac agttatcact tacttactgt agcccattgc  540
gtttataagt ttacgcttga aaatgctttt cccttgaaag taagactggg agaatgggat  600
acccaaaata ccaacgagtt cttgaagcat gaagattatg aagtggaaaa aatttacgtt  660
catcctaaat atgatcatga aaggaaaaac ttgtgggacg acattgctgt tttgaaactg  720
aaagctgaag tttcctttgg tcctcacatt gacaccatct gcttaccaaa taatcaagaa  780
cattttgcag gtgttcagtg tgtggttact ggttggggaa agaatgccta caaaaatggt  840
tcgtactcca atgtattacg ggaagtccac atgcctgtta ttaccaacga aaggtgtcag  900
gagcttctga aaaaaactag attaagtgaa tggttcgtct tgtacgaaaa ctttatctgt  960
gctggtggag aaagtaacac cgattcttgc aagggagatg gaggtggtcc tttagcctgc  1020
tggaggaaag atggtactta tggactggca ggtctggtat cgtgggggat tgactgtggt  1080
agtcctaatg tacctggtgt ttatgtcaga gtttcaaatt atcttgattg gattaccaag  1140
gttactggtc gtccaatttc tgattactgg ccacgttcgt aa                    1182
```

REAGENT FOR MEASURING ß-GLUCAN, METHOD FOR PRODUCING SAME AND USE THEREOF

TECHNICAL FIELD

The present invention relates to the provision and use of a novel reagent for β-glucan measurement.

BACKGROUND ART

Mycosis is a disease caused by infection with a fungus, and superficial mycosis in which a fungus causes infection on a surface of the body such as the skin or a mucous membrane, and deep mycosis in which a fungus causes infection in a deep part of the body such as a lung or blood are known. A polysaccharide that makes up a fungal cell wall is characteristic in that it contains a β-glucan. For this reason, detection of a β-glucan is used as a test/diagnostic method for mycosis (especially deep mycosis).

A horseshoe crab hemocyte extract (amebocyte lysate) is known to coagulate on reacting with a β-glucan, and is used as a reagent for β-glucan measurement. When a β-glucan comes into contact with the hemocyte extract, a factor G present in the hemocyte extract is activated to generate an active factor G having serine protease activity. This active factor G cleaves a proclotting enzyme present in the hemocyte extract to generate an active proclotting enzyme (that is, a clotting enzyme) having serine protease activity. This active proclotting enzyme cleaves a coagulogen present in the hemocyte extract, and the hemocyte extract is coagulated due to the action of coagulin generated thereby (FIG. 1). By using this series of cascade reactions, a reagent for β-glucan measurement containing a substrate for measurement including a sequence cleaved by an active proclotting enzyme has been invented.

Attempts have been made to artificially produce the above-mentioned factor G or proclotting enzyme using a recombinant technique or the like and to create a reagent for β-glucan measurement without depending on a horseshoe crab hemocyte extract. For example, WO95/001432 (PATENT LITERATURE 1) describes an invention relating to a polypeptide containing a (1→3)-β-D-glucan binding site of factor G and a cDNA encoding the polypeptide. WO2008/004674 (PATENT LITERATURE 2) describes an invention relating to a nucleic acid encoding a horseshoe crab-derived proclotting enzyme, and the like. JP2006-271384A (PATENT LITERATURE 3) describes an invention relating to a virus containing a DNA encoding an α-subunit of the horseshoe crab-derived factor G. WO2021/117841 (PATENT LITERATURE 4) describes an invention relating to a heterodimer of a combination of a factor G α-subunit having a specific amino acid sequence and a factor G β-subunit having a specific amino acid sequence. WO2021/117841 (PATENT LITERATURE 4) also describes an invention relating to a recombinant factor G derived from *Limulus polyphemus* expressed using an insect cell as a host.

CITATION LIST

Patent Literature

Patent Literature 1: WO95/001432
PATENT LITERATURE 2: WO2008/004674
PATENT LITERATURE 3: JP2006-271384A
PATENT LITERATURE 4: WO2021/117841

SUMMARY OF INVENTION

The conventional reagents for β-glucan measurement using artificially produced factor G or proclotting enzyme did not have sufficient performance.

For example, Example 3 in PATENT LITERATURE 2 discloses the result of confirming the expression of the activity by a β-glucan using a recombinant factor G and a recombinant proclotting enzyme. However, in the invention described in PATENT LITERATURE 2, a β-glucan at a high concentration of at least 1 ng/mL is required for the expression of the activity.

In PATENT LITERATURE 3, even when 0.25 ng of a β-glucan with respect to the total volume of 125.1 μl (that is, 2 ng/mL of a β-glucan) was used, the reaction took as long as 24 hours, which was not satisfactory in diagnosis of mycosis.

Further, Example 3 in PATENT LITERATURE 4 describes that it was possible to confirm that by using a supernatant containing a coexpression product of the specific factor G α-subunit and β-subunit, lentinan (a type of β-glucan) can be significantly detected at the lower limit down to 0.35 pg/mL. However, the invention described in PATENT LITERATURE 4 also requires a long reaction time of 200 minutes after mixing the reagent and a sample.

An object of the invention is, without requiring a horseshoe crab hemocyte extract, to provide a high-performance reagent for β-glucan measurement, and a material useful for producing the reagent.

Solution to Problem

According to one aspect of the invention, a high-performance reagent for β-glucan measurement can be provided without requiring a horseshoe crab hemocyte extract by coexisting a specific component during the reaction between a β-glucan and the reagent.

According to another aspect of the invention, an efficient method for producing a recombinant factor G using a mammalian cell is provided.

That is, the invention includes the following aspects.

[1-1]A reagent for β-glucan measurement, containing a horseshoe crab-derived factor D, a horseshoe crab-derived factor G, a horseshoe crab-derived proclotting enzyme, and a substrate for measurement, wherein the reagent does not contain a horseshoe crab hemocyte extract.

[1-2] The reagent for β-glucan measurement according to [1-1], wherein the horseshoe crab-derived factor D, the horseshoe crab-derived factor G, and the horseshoe crab-derived proclotting enzyme are recombinant proteins.

[1-3] The reagent for β-glucan measurement according to [1-1] or [1-2], wherein a detection limit for pachyman is 20 pg/mL or less within a reaction time of 60 minutes.

[1-4] The reagent for β-glucan measurement according to any one of [1-1] to [1-3], wherein the detection limit for pachyman is 16 pg/mL or less within a reaction time of 40 minutes.

[1-5] The reagent for β-glucan measurement according to any one of [1-1] to [1-4], wherein the horseshoe crab-derived factor D is the following protein (1) or (2):

(1) a protein that contains an amino acid sequence of any one of SEQ ID NOS: 1 to 12, 32, 33, and 67 to 70; or (2) a protein that contains an amino acid sequence having about 85% or more identity to at least one amino acid sequence of SEQ ID NOS: 1 to 12, 32, 33, and 67 to 70, and has the function of the factor D.

[1-6] The reagent for β-glucan measurement according to any one of [1-1] to [1-4], wherein the horseshoe crab-derived factor D is the following protein (1) or (2):

(1) a protein that contains an amino acid sequence of any one of SEQ ID NOS: 1 to 12, 32, and 33; or (2) a protein that contains an amino acid sequence having about 85% or more identity to at least one amino acid sequence of SEQ ID NOS: 1 to 12, 32, and 33, and has the function of the factor D.

[1-7] The reagent for β-glucan measurement according to any one of [1-1] to [1-6], wherein the horseshoe crab-derived factor D is the following protein (1) or (2):

(1) a protein that contains an amino acid sequence of any one of SEQ ID NOS: 1 to 12, 32, 33, and 67 to 70; or (2) a protein that contains an amino acid sequence having about 90% or more identity to at least one amino acid sequence of SEQ ID NOS: 1 to 12, 32, 33, and 67 to 70, and has the function of the factor D.

[1-8] The reagent for β-glucan measurement according to any one of [1-1] to [1-6], wherein the horseshoe crab-derived factor D is the following protein (1) or (2):

(1) a protein that contains an amino acid sequence of any one of SEQ ID NOS: 1 to 12, 32, and 33; or (2) a protein that contains an amino acid sequence having about 90% or more identity to at least one amino acid sequence of SEQ ID NOS: 1 to 12, 32, and 33, and has the function of the factor D.

[1-9] The reagent for β-glucan measurement according to any one of [1-1] to [1-8], wherein the horseshoe crab-derived factor D is the following protein (1') or (2'):

(1') a protein that contains an amino acid sequence of any one of SEQ ID NOS: 2, 4, 6, 8, 10, 12, 33, 68, and 70; or (2') a protein that contains an amino acid sequence having about 85% or more identity to at least one amino acid sequence of SEQ ID NOS: 2, 4, 6, 8, 10, 12, 33, 68, and 70, and has the function of the factor D.

[1-10] The reagent for β-glucan measurement according to any one of [1-1] to [1-8], wherein the horseshoe crab-derived factor D is the following protein (1') or (2'):

(1') a protein that contains an amino acid sequence of any one of SEQ ID NOS: 2, 4, 6, 8, 10, 12, and 33; or (2') a protein that contains an amino acid sequence having about 85% or more identity to at least one amino acid sequence of SEQ ID NOS: 2, 4, 6, 8, 10, 12, and 33, and has the function of the factor D.

[1-11] The reagent for β-glucan measurement according to any one of [1-1] to [1-10], wherein the horseshoe crab-derived factor D is the following protein (1') or (2'):

(1') a protein that contains an amino acid sequence of any one of SEQ ID NOS: 2, 4, 6, 8, 10, 12, 33, 68, and 70; or (2') a protein that contains an amino acid sequence having about 90% or more identity to at least one amino acid sequence of SEQ ID NOS: 2, 4, 6, 8, 10, 12, 33, 68, and 70, and has the function of the factor D.

[1-12] The reagent for β-glucan measurement according to any one of [1-1] to [1-10], wherein the horseshoe crab-derived factor D is the following protein (1') or (2'):

(1') a protein that contains an amino acid sequence of any one of SEQ ID NOS: 2, 4, 6, 8, 10, 12, and 33; or (2') a protein that contains an amino acid sequence having about 90% or more identity to at least one amino acid sequence of SEQ ID NOS: 2, 4, 6, 8, 10, 12, and 33, and has the function of the factor D.

[1-13] The reagent for β-glucan measurement according to any one of [1-1] to [1-12], wherein the horseshoe crab-derived factor D is derived from *Tachypleus tridentatus, Limulus polyphemus, Carcinoscorpius rotundicauda*, or *Tachypleus gigas.*

[1-14] The reagent for β-glucan measurement according to any one of [1-1] to [1-12], wherein the horseshoe crab-derived factor D is derived from *Tachypleus tridentatus* or *Limulus polyphemus.*

[1-15] The reagent for β-glucan measurement according to any one of [1-1] to [1-14], wherein the substrate for measurement is represented by the general formula Y—X—Z:

provided that in the general formula, Y is a hydrogen atom or a protecting group, X is a peptide containing the sequence of the substrate for the horseshoe crab-derived proclotting enzyme, and Z is a labeling substance.

[1-16] The reagent for β-glucan measurement according to [1-15], wherein the labeling substance is an optical labeling substance.

[1-17] The reagent for β-glucan measurement according to any one of [1-1] to [1-16], wherein the horseshoe crab-derived factor G is derived from *Tachypleus tridentatus* or *Limulus polyphemus.*

[1-18] The reagent for β-glucan measurement according to any one of [1-1] to [1-17], wherein the horseshoe crab-derived proclotting enzyme is derived from *Tachypleus tridentatus* or *Limulus polyphemus.*

[2-1]A method for producing a reagent for β-glucan measurement, including:

artificially producing a horseshoe crab-derived factor D; and kitting the artificially produced horseshoe crab-derived factor D into a kit together with at least a horseshoe crab-derived factor G, a horseshoe crab-derived proclotting enzyme, and a substrate for measurement.

[2-2] The production method according to [2-1], wherein the artificial production of the horseshoe crab-derived factor D is recombinant production using a host cell.

[2-3] The production method according to [2-1] or [2-2], wherein a detection limit for pachyman of the reagent for β-glucan measurement is 20 pg/mL or less within a reaction time of 60 minutes.

[2-4] The production method according to any one of [2-1] to [2-3], wherein the detection limit for pachyman of the reagent for β-glucan measurement is 16 pg/mL or less within a reaction time of 40 minutes.

[2-5] The production method according to any one of [2-1] to [2-4], wherein the horseshoe crab-derived factor D is the following protein (1) or (2):

(1) a protein that contains an amino acid sequence of any one of SEQ ID NOS: 1 to 12, 32, 33, and 67 to 70; or (2) a protein that contains an amino acid sequence having about 85% or more identity to at least one amino acid sequence of SEQ ID NOS: 1 to 12, 32, 33, and 67 to 70, and has the function of the factor D.

[2-6] The production method according to any one of [2-1] to [2-4], wherein the horseshoe crab-derived factor D is the following protein (1) or (2):

(1) a protein that contains an amino acid sequence of any one of SEQ ID NOS: 1 to 12, 32, and 33; or (2) a protein that contains an amino acid sequence having about 85% or more identity to at least one amino acid sequence of SEQ ID NOS: 1 to 12, 32, and 33, and has the function of the factor D.

[2-7] The production method according to any one of [2-1] to [2-6], wherein the horseshoe crab-derived factor D is the following protein (1) or (2):

(1) a protein that contains an amino acid sequence of any one of SEQ ID NOS: 1 to 12, 32, 33, and 67 to 70; or (2) a protein that contains an amino acid sequence having about 90% or more identity to at least one amino acid sequence of SEQ ID NOS: 1 to 12, 32, 33, and 67 to 70, and has the function of the factor D.

[2-8] The production method according to any one of [2-1] to [2-6], wherein the horseshoe crab-derived factor D is the following protein (1) or (2):

(1) a protein that contains an amino acid sequence of any one of SEQ ID NOS: 1 to 12, 32, and 33; or (2) a protein that contains an amino acid sequence having about 90% or more identity to at least one amino acid sequence of SEQ ID NOS: 1 to 12, 32, and 33, and has the function of the factor D.

[2-9] The production method according to any one of [2-1] to [2-8], wherein the horseshoe crab-derived factor D is the following protein (1') or (2'):

(1') a protein that contains an amino acid sequence of any one of SEQ ID NOS: 2, 4, 6, 8, 10, 12, 33, 68, and 70; or (2') a protein that contains an amino acid sequence having about 85% or more identity to at least one amino acid sequence of SEQ ID NOS: 2, 4, 6, 8, 10, 12, 33, 68, and 70, and has the function of the factor D.

[2-10] The production method according to any one of [2-1] to [2-8], wherein the horseshoe crab-derived factor D is the following protein (1') or (2'):

(1') a protein that contains an amino acid sequence of any one of SEQ ID NOS: 2, 4, 6, 8, 10, 12, and 33; or (2') a protein that contains an amino acid sequence having about 85% or more identity to at least one amino acid sequence of SEQ ID NOS: 2, 4, 6, 8, 10, 12, and 33, and has the function of the factor D.

[2-11] The production method according to any one of [2-1] to [2-10], wherein the horseshoe crab-derived factor D is the following protein (1') or (2'):

(1') a protein that contains an amino acid sequence of any one of SEQ ID NOS: 2, 4, 6, 8, 10, 12, 33, 68, and 70; or (2') a protein that contains an amino acid sequence having about 90% or more identity to at least one amino acid sequence of SEQ ID NOS: 2, 4, 6, 8, 10, 12, 33, 68, and 70, and has the function of the factor D.

[2-12] The production method according to any one of [2-1] to [2-10], wherein the horseshoe crab-derived factor D is the following protein (1') or (2'):

(1') a protein that contains an amino acid sequence of any one of SEQ ID NOS: 2, 4, 6, 8, 10, 12, and 33; or (2') a protein that contains an amino acid sequence having about 90% or more identity to at least one amino acid sequence of SEQ ID NOS: 2, 4, 6, 8, 10, 12, and 33, and has the function of the factor D.

[2-13] The production method according to any one of [2-1] to [2-12], wherein the horseshoe crab-derived factor D is derived from *Tachypleus tridentatus, Limulus polyphemus, Carcinoscorpius rotundicauda*, or *Tachypleus gigas*.

[2-14] The production method according to any one of [2-1] to [2-12], wherein the horseshoe crab-derived factor D is derived from *Tachypleus tridentatus* or *Limulus polyphemus*.

[2-15] The production method according to any one of [2-1] to [2-14], wherein the substrate for measurement is represented by the general formula Y—X—Z:

provided that in the general formula, Y is a hydrogen atom or a protecting group, X is a peptide containing the sequence of the substrate for the horseshoe crab-derived proclotting enzyme, and Z is a labeling substance.

[2-16] The production method according to [2-15], wherein the labeling substance is an optical labeling substance.

[2-17] The production method according to any one of [2-1] to [2-16], wherein the horseshoe crab-derived factor G is derived from *Tachypleus tridentatus* or *Limulus polyphemus*.

[2-18] The production method according to any one of [2-1] to [2-17], wherein the horseshoe crab-derived proclotting enzyme is derived from *Tachypleus tridentatus* or *Limulus polyphemus*.

[3-1]A β-glucan assay method, including measuring a β-glucan in a sample using the reagent for β-glucan measurement according to any one of [1-1] to [1-18] or a reagent for β-glucan measurement produced by the production method according to any one of [2-1] to [2-18].

[3-2]A β-glucan assay method, including measuring a β-glucan in a sample using the reagent for β-glucan measurement according to any one of [1-1] to [1-13] or a reagent for β-glucan measurement produced by the production method according to any one of [2-1] to [2-13].

[3-3]A test method for mycosis, including:

performing the β-glucan assay method according to [3-1], wherein the sample is a biological sample derived from a test subject suspected of having mycosis.

[3-4]A test method for mycosis, including:

performing the β-glucan assay method according to [3-2], wherein the sample is a biological sample derived from a test subject suspected of having mycosis.

[3-5]A data acquisition method for diagnosing mycosis, including:

acquiring data for diagnosing whether a test subject has mycosis by performing the β-glucan assay method according to [3-1], wherein the sample is a biological sample derived from the test subject.

[3-6]A data acquisition method for diagnosing mycosis, including:

acquiring data for diagnosing whether a test subject has mycosis by performing the β-glucan assay method according to [3-2], wherein the sample is a biological sample derived from the test subject.

[4-1]A method for enhancing the activity of a reagent for β-glucan measurement containing a horseshoe crab-derived factor G, a horseshoe crab-derived proclotting enzyme, and a substrate for measurement, including coexisting a horseshoe crab-derived factor D to coexist with the reagent for β-glucan measurement.

[4-2] The method according to [4-1], wherein the horseshoe crab-derived factor D is a recombinant protein.

[4-3] The method according to [4-1] or [4-2], wherein a detection limit for pachyman of the reagent for β-glucan measurement with enhanced activity is 20 pg/mL or less within a reaction time of 60 minutes.

[4-4] The method according to any one of [4-1] to [4-3], wherein the detection limit for pachyman of the reagent for β-glucan measurement with enhanced activity is 16 pg/mL or less within a reaction time of 40 minutes.

[4-5] The method according to any one of [4-1] to [4-4], wherein the horseshoe crab-derived factor D is the following protein (1) or (2):

(1) a protein that contains an amino acid sequence of any one of SEQ ID NOS: 1 to 12, 32, 33, and 67 to 70; or (2) a protein that contains an amino acid sequence having about 85% or more identity to at least one amino acid sequence of SEQ ID NOS: 1 to 12, 32, 33, and 67 to 70, and has the function of the factor D.

[4-6] The method according to any one of [4-1] to [4-4], wherein the horseshoe crab-derived factor D is the following protein (1) or (2):

(1) a protein that contains an amino acid sequence of any one of SEQ ID NOS: 1 to 12, 32, and 33; or (2) a protein that contains an amino acid sequence having about 85% or more identity to at least one amino acid sequence of SEQ ID NOS: 1 to 12, 32, and 33, and has the function of the factor D.

[4-7] The method according to any one of [4-1] to [4-6], wherein the horseshoe crab-derived factor D is the following protein (1) or (2):

(1) a protein that contains an amino acid sequence of any one of SEQ ID NOS: 1 to 12, 32, 33, and 67 to 70; or (2) a protein that contains an amino acid sequence having about 90% or more identity to at least one amino acid sequence of SEQ ID NOS: 1 to 12, 32, 33, and 67 to 70, and has the function of the factor D.

[4-8] The method according to any one of [4-1] to [4-6], wherein the horseshoe crab-derived factor D is the following protein (1) or (2):

(1) a protein that contains an amino acid sequence of any one of SEQ ID NOS: 1 to 12, 32, and 33; or (2) a protein that contains an amino acid sequence having about 90% or more identity to at least one amino acid sequence of SEQ ID NOS: 1 to 12, 32, and 33, and has the function of the factor D.

[4-9] The method according to any one of [4-1] to [4-8], wherein the horseshoe crab-derived factor D is the following protein (1') or (2'):

(1') a protein that contains an amino acid sequence of any one of SEQ ID NOS: 2, 4, 6, 8, 10, 12, 33, 68, and 70; or (2') a protein that contains an amino acid sequence having about 85% or more identity to at least one amino acid sequence of SEQ ID NOS: 2, 4, 6, 8, 10, 12, 33, 68, and 70, and has the function of the factor D.

[4-10] The method according to any one of [4-1] to [4-8], wherein the horseshoe crab-derived factor D is the following protein (1') or (2'):

(1') a protein that contains an amino acid sequence of any one of SEQ ID NOS: 2, 4, 6, 8, 10, 12, and 33; or (2') a protein that contains an amino acid sequence having about 85% or more identity to at least one amino acid sequence of SEQ ID NOS: 2, 4, 6, 8, 10, 12, and 33, and has the function of the factor D.

[4-11] The method according to any one of [4-1] to [4-10], wherein the horseshoe crab-derived factor D is the following protein (1') or (2'):

(1') a protein that contains an amino acid sequence of any one of SEQ ID NOS: 2, 4, 6, 8, 10, 12, 33, 68, and 70; or (2') a protein that contains an amino acid sequence having about 90% or more identity to at least one amino acid sequence of SEQ ID NOS: 2, 4, 6, 8, 10, 12, 33, 68, and 70, and has the function of the factor D.

[4-12] The method according to any one of [4-1] to [4-10], wherein the horseshoe crab-derived factor D is the following protein (1') or (2'):

(1') a protein that contains an amino acid sequence of any one of SEQ ID NOS: 2, 4, 6, 8, 10, 12, and 33; or (2') a protein that contains an amino acid sequence having about 90% or more identity to at least one amino acid sequence of SEQ ID NOS: 2, 4, 6, 8, 10, 12, and 33, and has the function of the factor D.

[4-13] The method according to any one of [4-1] to [4-12], wherein the horseshoe crab-derived factor D is derived from *Tachypleus tridentatus, Limulus polyphemus, Carcinoscorpius rotundicauda*, or *Tachypleus gigas.*

[4-14] The method according to any one of [4-1] to [4-12], wherein the horseshoe crab-derived factor D is derived from *Tachypleus tridentatus* or *Limulus polyphemus.*

[4-15] The method according to any one of [4-1] to [4-14], wherein the substrate for measurement is represented by the general formula Y—X—Z:

provided that in the general formula, Y is a hydrogen atom or a protecting group, X is a peptide containing the sequence of the substrate for the horseshoe crab-derived proclotting enzyme, and Z is a labeling substance.

[4-16] The method according to [4-15], wherein the labeling substance is an optical labeling substance.

[4-17] The method according to any one of [4-1] to [4-16], wherein the horseshoe crab-derived factor G is derived from *Tachypleus tridentatus* or *Limulus polyphemus.*

[4-18] The method according to any one of [4-1] to [4-17], wherein the horseshoe crab-derived proclotting enzyme is derived from *Tachypleus tridentatus* or *Limulus polyphemus.*

[5-1]A method for producing a material of a reagent for β-glucan measurement, including culturing a mammalian cell transformed with both of DNAs individually encoding *Tachypleus tridentatus*-derived factor G α-subunit and β-subunit, and collecting a culture supernatant after culturing.

[5-2] The production method according to [5-1], further including coexisting a *Limulus polyphemus*-derived proclotting enzyme in the culture supernatant.

[5-3] The production method according to [5-1] or [5-2], wherein the mammalian cell is a CHO cell, preferably a CHO DG44 cell.

[6-1]A culture supernatant of a mammalian cell transformed with both DNAs individually encoding *Tachypleus tridentatus*-derived factor G α-subunit and β-subunit.

[6-2] The culture supernatant according to [6-1], further containing a *Limulus polyphemus*-derived proclotting enzyme.

[6-3] The culture supernatant according to [6-1] or [6-2], wherein the mammalian cell is a CHO cell, preferably a CHO DG44 cell.

[6-4]A material of a reagent for β-glucan measurement, containing the culture supernatant according to any one of [6-1] to [6-3].

DESCRIPTION OF EMBODIMENTS

Figure 1:
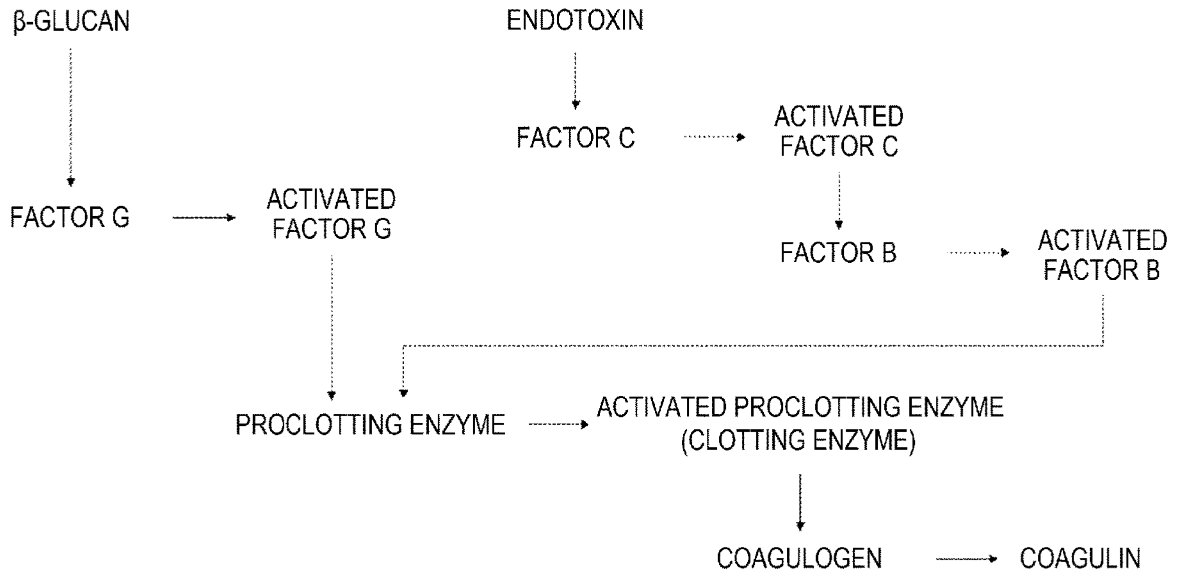
FIG. 1 shows a cascade reaction of a horseshoe crab hemocyte extract that is triggered by a β-glucan and an endotoxin, and proceeds.

According to the invention, a high-performance reagent for β-glucan measurement and a material useful for producing the reagent can be provided without requiring a horseshoe crab hemocyte extract.

The present inventors found a specific component that can improve the performance of a reagent for β-glucan measurement by coexisting the component during the reaction between a β-glucan and the reagent. More specifically, they found that when a reagent for β-glucan measurement containing horseshoe crab-derived factor G, a horseshoe crab-derived proclotting enzyme, and a substrate for measurement is allowed to react with a β-glucan, by coexisting further horseshoe crab-derived factor D to coexist, the responsiveness of the reagent to the β-glucan is improved. The horseshoe crab-derived factor D is a protein first discovered by Kawabata et al. (FEBS Letters 398 (1996) 146-150), and is known to have a function of suppressing the growth of Gram-negative bacteria. However, the relationship between the horseshoe crab-derived factor D and fungi or a β-glucan is unknown.

In this description, the three proteins: the horseshoe crab-derived factor D, the horseshoe crab-derived factor G, and the horseshoe crab-derived proclotting enzyme are sometimes referred to individually or collectively as "glucan-related factor".

Further, in this description, the horseshoe crab-derived factor D, the horseshoe crab-derived factor G, the horseshoe crab-derived proclotting enzyme, the horseshoe crab-derived factor C, and the horseshoe crab-derived factor B are sometimes simply referred to as "factor D", "factor G", "proclotting enzyme", "factor C", and "factor B", respectively. Note that in this description, it is clear from the idea of the invention and the entire description herein that the meaning of the term "horseshoe crab-derived" or "derived from a horseshoe crab" used for proteins is not intended to limit the material from which the protein is collected to a horseshoe crab.

Further, in this description, the reference to "one embodiment" or "an embodiment" means that a particular feature, structure, or characteristic described in connection with the embodiment is included in at least one embodiment of the invention, and indicates that every embodiment does not necessarily include the particular feature, structure, or characteristic. Moreover, particular features, structures, or characteristics may be combined in any suitable manner in one or more embodiments.

Hereinafter, embodiments of the invention will be described, but the invention is not limited only to the following embodiments.

<Reagent for β-Glucan Measurement>

One aspect of the invention relates to a reagent for β-glucan measurement containing horseshoe crab-derived factor D. The reagent for β-glucan measurement is preferably a recombinant reagent containing a horseshoe crab-derived factor D (that is, the factor G and the proclotting enzyme contained in the reagent for β-glucan measurement are both recombinant proteins).

In an embodiment, a reagent for β-glucan measurement that contains a horseshoe crab-derived factor D, a horseshoe crab-derived factor G, a horseshoe crab-derived proclotting enzyme, and a substrate for measurement, and does not contain a horseshoe crab hemocyte extract is provided.

In an embodiment, a reagent for β-glucan measurement that contains a horseshoe crab-derived factor D recombinant protein, a horseshoe crab-derived factor G recombinant protein, a horseshoe crab-derived proclotting enzyme recombinant protein, and a substrate for measurement is provided. In an embodiment, a reagent for β-glucan measurement that contains a substrate for measurement, and contains, as the glucan-related factors, only a horseshoe crab-derived factor D recombinant protein, a horseshoe crab-derived factor G recombinant protein, and a horseshoe crab-derived proclotting enzyme recombinant protein is provided.

In this description, the species of the horseshoe crab from which the glucan-related factors are derived is not particularly limited. As the species of the horseshoe crab, 4 species: *Tachypleus tridentatus, Limulus polyphemus, Carcinoscorpius rotundicauda*, and *Tachypleus gigas* are known. Among these horseshoe crabs, each glucan-related factor is preferably selected independently from the group consisting of *Tachypleus tridentatus, Carcinoscorpius rotundicauda*, and *Limulus polyphemus*, and is more preferably selected independently from the group consisting of *Tachypleus tridentatus* and *Limulus polyphemus.*

In this description, the "factor D" is not limited as long as it is a polypeptide having the function of the factor D, and also includes a variant of the factor D possessed by a natural horseshoe crab. The "function of the factor D" is a function of improving the responsiveness of the reagent to a β-glucan, as compared to a case where the polypeptide is not allowed to coexist, by coexisting the polypeptide when the reagent for β-glucan measurement containing the factor G, the proclotting enzyme, and the substrate for measurement is allowed to react with a β-glucan. In a case where a given polypeptide is allowed to coexist with the reagent for β-glucan measurement, if the responsiveness of the reagent to a β-glucan is improved as compared with a case where it is not allowed to coexist, it can be deemed that the polypeptide has the "function of the factor D". The method for confirming the improvement of the responsiveness is appropriately selected by those skilled in the art based on the assay method to be adopted. Specifically, the fact that the responsiveness is improved can be confirmed, for example, by an increase in the amount of a free labeling substance when using an endpoint method, or by an increase in the release rate of a labeling substance when using a kinetic method. More specifically, the improvement of the responsiveness can be confirmed by a method described in Examples.

In an embodiment, the factor D is derived from *Tachypleus tridentatus*. In an embodiment, the amino acid sequence of the factor D derived from *Tachypleus tridentatus* is a sequence represented by SEQ ID NO: 1 (GenBank: BAA13312.1) in the sequence listing.

In an embodiment, the amino acid sequence of the factor D is a sequence represented by SEQ ID NO: 2 in the sequence listing, which is obtained by cleaving the signal sequence from SEQ ID NO: 1.

In an embodiment, the amino acid sequence of the factor D derived from *Tachypleus tridentatus* is a sequence represented by SEQ ID NO: 3 in the sequence listing.

In an embodiment, the amino acid sequence of the factor D is a sequence represented by SEQ ID NO: 4 in the sequence listing, which is obtained by cleaving the signal sequence from SEQ ID NO: 3.

In an embodiment, the amino acid sequence of the factor D derived from *Tachypleus tridentatus* is a sequence represented by SEQ ID NO: 5 in the sequence listing (a sequence, which is obtained by changing the N-terminal secretory signal and adding a His tag to the C-terminus in SEQ ID NO: 3).

In an embodiment, the amino acid sequence of the factor D is a sequence represented by SEQ ID NO: 6 in the sequence listing, which is obtained by cleaving the signal sequence from SEQ ID NO: 5.

In an embodiment, the factor D is derived from *Limulus polyphemus*. In an embodiment, the amino acid sequence of the factor D derived from *Limulus polyphemus* is a sequence represented by SEQ ID NO: 7 in the sequence listing.

In an embodiment, the amino acid sequence of the factor D is a sequence represented by SEQ ID NO: 8 in the sequence listing, which is obtained by cleaving the signal sequence from SEQ ID NO: 7.

In an embodiment, the amino acid sequence of the factor D derived from *Limulus polyphemus* is a sequence represented by SEQ ID NO: 9 in the sequence listing.

In an embodiment, the amino acid sequence of the factor D is a sequence represented by SEQ ID NO: 10 in the sequence listing, which is obtained by cleaving the signal sequence from SEQ ID NO: 9.

In an embodiment, the amino acid sequence of the factor D derived from *Limulus polyphemus* is a sequence represented by SEQ ID NO: 11 in the sequence listing (a sequence, which is obtained by changing the N-terminal secretory signal and adding a His tag to the C-terminus in SEQ ID NO: 9).

In an embodiment, the amino acid sequence of the factor D is a sequence represented by SEQ ID NO: 12 in the sequence listing, which is obtained by cleaving the signal sequence from SEQ ID NO: 11.

In an embodiment, the amino acid sequence of the factor D derived from *Limulus polyphemus* is a sequence represented by SEQ ID NO: 32 in the sequence listing (a sequence, which is obtained by changing the N-terminal secretory signal in SEQ ID NO: 9).

In an embodiment, the amino acid sequence of the factor D is a sequence represented by SEQ ID NO: 33 in the sequence listing, which is obtained by cleaving the signal sequence from SEQ ID NO: 32.

In an embodiment, the factor D is derived from *Carcinoscorpius rotundicauda*. In an embodiment, the amino acid sequence of the factor D derived from *Carcinoscorpius rotundicauda* is a sequence represented by SEQ ID NO: 67 in the sequence listing (corresponding to the coding region of GenBank: GILQ01008045.1; SEQ ID NO: 71).

In an embodiment, the amino acid sequence of the factor D is a sequence represented by SEQ ID NO: 68 in the sequence listing, which is obtained by cleaving the signal sequence from SEQ ID NO: 67.

In an embodiment, the factor D is derived from *Tachypleus gigas*. In an embodiment, the amino acid sequence of the factor D derived from *Tachypleus gigas* is a sequence represented by SEQ ID NO: 69 in the sequence listing (corresponding to the coding region of GenBank: GILM01006809.1; SEQ ID NO: 72).

In an embodiment, the amino acid sequence of the factor D is a sequence represented by SEQ ID NO: 70 in the sequence listing, which is obtained by cleaving the signal sequence from SEQ ID NO: 69.

The factor D in this description also includes a protein in which one or multiple amino acid residues have been replaced, deleted, inserted, and/or added in the amino acid sequence of any of SEQ ID NOS: 1 to 12, 32, 33, and 67 to 70. In an embodiment, the factor D is a protein in which one or multiple amino acid residues have been replaced, deleted, inserted, and/or added in the amino acid sequence of SEQ ID NO: 2, 4, 6, 8, 10, 12, 33, 68, or 70. In this description, the "multiple" means the number (total number) of amino acid residues to such an extent that the protein does not lose the function of the factor D even if the amino acid residues are replaced, deleted, inserted, and/or added. The "multiple" may be, for example, a number of preferably about 15% or less, more preferably about 10% or less, even more preferably about 5% or less, and particularly preferably about 1% or less with respect to the total number of amino acid residues that make up the protein. In the case of the amino acid sequence of the protein represented by any of the above SEQ ID NOS: 1 to 12 described above, the "multiple" can be preferably 2 to 55, more preferably 2 to 35, even more preferably 2 to 15, and particularly preferably 2 to 3.

In this description, the "about" indicates within the range of ±5% of the value following the "about". For example, the notation "about 10%" in this description is interpreted as "9.5% or more and 10.5% or less".

In this description, the "substitution, deletion, insertion, and/or addition" is, for example, a conservative mutation. A representative conservative mutation is a conservative substitution. The conservative substitution is a mutation in which, for example, in a case where the substitution site is an aromatic amino acid residue, substitution occurs between Phe, Trp, and Tyr, in a case where the substitution site is a hydrophobic amino acid residue, substitution occurs between Leu, Ile, and Val, in a case where the substitution site is a polar amino acid, substitution occurs between Gln and Asn, in a case where the substitution site is a basic amino acid residue, substitution occurs between Lys, Arg, and His, in a case where the substitution site is an acidic amino acid residue, substitution occurs between Asp and Glu, and in a case where the substitution site is an amino acid residue having a hydroxyl group, substitution occurs between Ser and Thr. Specific examples of the substitution regarded as the conservative substitution include substitution of Ala with Ser or Thr, substitution of Arg with Gln, His, or Lys, substitution of Asn with Glu, Gln, Lys, His, or Asp, substitution of Asp with Asn, Glu, or Gln, substitution of Cys with Ser or Ala, substitution of Gln with Asn, Glu, Lys, His, Asp, or Arg, substitution of Glu with Gly, Asn, Gln, Lys, or Asp, substitution of Gly with Pro, substitution of His with Asn, Lys, Gln, Arg, or Tyr, substitution of Ile with Leu, Met, Val, or Phe, substitution of Leu with Ile, Met, Val, or Phe, substitution of Lys with Asn, Glu, Gln, His, or Arg, substitution of Met with Ile, Leu, Val, or Phe, substitution of Phe with Trp, Tyr, Met, Ile, or Leu, substitution of Ser with Thr or Ala, substitution of Thr with Ser or Ala, substitution of Trp with Phe or Tyr, substitution of Tyr with His, Phe, or Trp, and substitution of Val with Met, Ile, or Leu.

The results of evaluating the sequence identity between the respective amino acid sequences of the factor D represented by SEQ ID NOS: 2, 4, 6, 8, 10, 12, 33, 68, and 70 described above are shown in the following Table 1.

TABLE 1

| | SEQ ID NO: 2 | SEQ ID NO: 4 | SEQ ID NO: 6 | SEQ ID NO: 8 | SEQ ID NO: 10 | SEQ ID NO: 12 | SEQ ID NO: 33 | SEQ ID NO: 68 | (%) SEQ ID NO: 70 |
|---|---|---|---|---|---|---|---|---|---|
| SEQ ID NO: 2 | — | — | — | — | — | — | — | — | — |
| SEQ ID NO: 4 | 99 | — | — | — | — | — | — | — | — |
| SEQ ID NO: 6 | 97 | 97 | — | — | — | — | — | — | — |
| SEQ ID NO: 8 | 86 | 86 | 84 | — | — | — | — | — | — |
| SEQ ID NO: 10 | 89 | 89 | 87 | 87 | — | — | — | — | — |
| SEQ ID NO: 12 | 87 | 87 | 89 | 85 | 97 | — | — | — | — |
| SEQ ID NO: 33 | 88 | 88 | 88 | 86 | 99 | 98 | — | — | — |
| SEQ ID NO: 68 | 94 | 94 | 92 | 84 | 87 | 85 | 86 | — | — |
| SEQ ID NO: 70 | 94 | 95 | 93 | 85 | 89 | 87 | 89 | 94 | — |

(Decimals are rounded down.)

The amino acid sequences represented by SEQ ID NOS: 2, 4, 6, 8, 10, 12, and 33 all have about 85% or more (for example, 84% or more) identity to each other. Further, proteins having these amino acid sequences all have the function of the factor D. Those skilled in the art can understand that a protein having an amino acid sequence with about 85% or more identity to the amino acid sequence of at least one of SEQ ID NOS: 2, 4, 6, 8, 10, 12, 33, 68, and 70, and SEQ ID NOS: 1, 3, 5, 7, 9, 11, 32, 67, and 69 in which a signal sequence has been added thereto (that is, at least one of SEQ ID NOS: 1 to 12, 32, 33, and 67 to 70) functions as the factor D.

In an embodiment, the factor D is the following protein (1) or (2):

(1) a protein that contains an amino acid sequence of any one of SEQ ID NOS: 1 to 12, 32, 33, and 67 to 70; or (2) a protein that contains an amino acid sequence having preferably about 85% or more, more preferably about 90% or more, even more preferably about 95% or more, still even more preferably about 98% or more, and particularly preferably about 99% or more identity to at least one amino acid sequence of SEQ ID NOS: 1 to 12, 32, 33, and 67 to 70, and has the function of the factor D.

In an embodiment, the factor D is the following protein (1) or (2):

(1) a protein that contains an amino acid sequence of any one of SEQ ID NOS: 1 to 12, 32, and 33; or (2) a protein that contains an amino acid sequence having preferably about 85% or more, more preferably about 90% or more, even more preferably about 95% or more, still even more preferably about 98% or more, and particularly preferably about 99% or more identity to at least one amino acid sequence of SEQ ID NOS: 1 to 12, 32, and 33, and has the function of the factor D.

In an embodiment, the factor D is the following protein (1') or (2'):

(1') a protein that contains an amino acid sequence of any one of SEQ ID NOS: 2, 4, 6, 8, 10, 12, 33, 68, and 70; or (2') a protein that contains an amino acid sequence having preferably about 85% or more, more preferably about 90% or more, even more preferably about 95% or more, still even more preferably about 98% or more, and particularly preferably about 99% or more identity to at least one amino acid sequence of SEQ ID NOS: 2, 4, 6, 8, 10, 12, 33, 68, and 70, and has the function of the factor D.

In an embodiment, the factor D is the following protein (1') or (2'):

(1') a protein that contains an amino acid sequence of any one of SEQ ID NOS: 2, 4, 6, 8, 10, 12, and 33; or (2') a protein that contains an amino acid sequence having preferably about 85% or more, more preferably about 90% or more, even more preferably about 95% or more, still even more preferably about 98% or more, and particularly preferably about 99% or more identity to at least one amino acid sequence of SEQ ID NOS: 2, 4, 6, 8, 10, 12, and 33, and has the function of the factor D.

In a preferred embodiment, the factor D is a protein selected from the group consisting of the following (1") to (10"):

(1") a protein that contains an amino acid sequence of any one of SEQ ID NOS: 2, 4, 6, 8, 10, 12, 33, 68, and 70;

(2") a protein that contains an amino acid sequence having about 86% or more identity to the amino acid sequence represented by SEQ ID NO: 2, and has the function of the factor D;

(3") a protein that contains an amino acid sequence having about 86% or more identity to the amino acid sequence represented by SEQ ID NO: 4, and has the function of the factor D;

(4") a protein that contains an amino acid sequence having about 84% or more identity to the amino acid sequence represented by SEQ ID NO: 6, and has the function of the factor D;

(5") a protein that contains an amino acid sequence having about 84% or more identity to the amino acid sequence represented by SEQ ID NO: 8, and has the function of the factor D;

(6") a protein that contains an amino acid sequence having about 87% or more identity to the amino acid sequence represented by SEQ ID NO: 10, and has the function of the factor D;

(7") a protein that contains an amino acid sequence having about 85% or more identity to the amino acid sequence represented by SEQ ID NO: 12, and has the function of the factor D;

(8") a protein that contains an amino acid sequence having about 86% or more identity to the amino acid sequence represented by SEQ ID NO: 33, and has the function of the factor D;

(9") a protein that contains an amino acid sequence having about 84% or more identity to the amino acid sequence represented by SEQ ID NO: 68, and has the function of the factor D; and (10") a protein that contains an amino acid sequence having about 85% or more identity to the amino acid sequence represented by SEQ ID NO: 70, and has the function of the factor D.

In a more preferred embodiment, the factor D is a protein selected from the group consisting of the following (1") to (8"):

(1") a protein that contains an amino acid sequence of any one of SEQ ID NOS: 2, 4, 6, 8, 10, 12, and 33;

(2") a protein that contains an amino acid sequence having about 86% or more identity to the amino acid sequence represented by SEQ ID NO: 2, and has the function of the factor D;

(3") a protein that contains an amino acid sequence having about 86% or more identity to the amino acid sequence represented by SEQ ID NO: 4, and has the function of the factor D;

(4") a protein that contains an amino acid sequence having about 84% or more identity to the amino acid sequence represented by SEQ ID NO: 6, and has the function of the factor D;

(5") a protein that contains an amino acid sequence having about 84% or more identity to the amino acid sequence represented by SEQ ID NO: 8, and has the function of the factor D;

(6") a protein that contains an amino acid sequence having about 87% or more identity to the amino acid sequence represented by SEQ ID NO: 10, and has the function of the factor D;

(7") a protein that contains an amino acid sequence having about 85% or more identity to the amino acid sequence represented by SEQ ID NO: 12, and has the function of the factor D; and (8") a protein that contains an amino acid sequence having about 86% or more identity to the amino acid sequence represented by SEQ ID NO: 33, and has the function of the factor D.

As a specific example in which one amino acid residue has been replaced in the amino acid sequence of SEQ ID NO: 2, a sequence represented by SEQ ID NO: 35, 36, 37, 38, 39, 40, 41, or 42 in the sequence listing is exemplified. In one embodiment, the amino acid sequence of the factor D is a sequence represented by SEQ ID NO: 39, 40, 41, or 42 in the sequence listing.

As a specific example in which one amino acid residue has been replaced in the amino acid sequence of SEQ ID NO: 4, a sequence represented by SEQ ID NO: 43, 44, 45, 46, 47, 48, 49, or 50 in the sequence listing is exemplified. In one embodiment, the amino acid sequence of the factor D is a sequence represented by SEQ ID NO: 47, 48, 49, or 50 in the sequence listing.

As a specific example in which one amino acid residue has been replaced in the amino acid sequence of SEQ ID NO: 8, a sequence represented by SEQ ID NO: 51, 52, 53, 54, 55, 56, 57, or 58 in the sequence listing is exemplified. In one embodiment, the amino acid sequence of the factor D is a sequence represented by SEQ ID NO: 55, 56, 57, or 58 in the sequence listing.

As a specific example in which one amino acid residue has been replaced in the amino acid sequence of SEQ ID NO: 10, a sequence represented by SEQ ID NO: 59, 60, 61, 62, 63, 64, 65, or 66 in the sequence listing is exemplified. In one embodiment, the amino acid sequence of the factor D is a sequence represented by SEQ ID NO: 63, 64, 65, or 66 in the sequence listing.

In an embodiment, the factor D is a protein composed of an amino acid sequence of any one of SEQ ID NOS: 2, 4, 6, 8, 10, 12, 33, and 35 to 66.

In an embodiment, the factor D is a protein composed of an amino acid sequence of any one of SEQ ID NOS: 2, 4, 6, 8, 10, 12, 33, 39 to 42, 47 to 50, 55 to 58, and 63 to 66.

In an embodiment, the factor D is a protein composed of an amino acid sequence of any one of SEQ ID NOS: 2, 4, 6, 8, 10, 12, 33, and 47 to 50.

In an embodiment, the factor D is a protein composed of an amino acid sequence of any one of SEQ ID NOS: 2, 4, 6, 8, 10, 12, and 33.

The identity of amino acid sequences can be calculated using a well-known computer software, and for example, the identity can be calculated by sequence alignment processing using the algorithm BLAST (Karlin, S., Altschul, SF. (1993) Proc. Natl. Acad. Sci. U.S.A., 90, 5873-7). The identity of amino acid sequences can be specifically calculated using, for example, GENETYX (GENETYX CORPORATION).

In an embodiment, the reagent for β-glucan measurement in which the factor D is derived from *Tachypleus tridentatus, Limulus polyphemus, Carcinoscorpius rotundicauda*, or *Tachypleus gigas* is provided.

In a preferred embodiment, the reagent for β-glucan measurement in which the factor D is derived from *Tachypleus tridentatus* or *Limulus polyphemus* is provided.

Natural factor D does not have an essential serine residue at the active center for a serine protease, and therefore does not have serine protease activity like the factor G or the proclotting enzyme. Although not intended to limit the technical scope of the invention, when the factor D acquires serine protease activity through the introduction of a mutation of a serine residue or the like, decrease in the molecular weight of the protein may proceed due to autolysis or degradation of other contaminant proteins during the purification process or the like. Although the relationship between the responsiveness of the reagent to a β-glucan and the presence or absence of the serine protease activity of the factor D is unknown, in the invention, it is preferred to use the factor D which does not have serine protease activity from the viewpoint of preventing the decrease in the molecular weight of the material used in the reagent for β-glucan measurement. The fact that the factor D does not have serine protease activity can be confirmed by developing the factor D by electrophoresis under reducing conditions and under non-reducing conditions, and confirming that the molecular weight of the factor D detected under the reducing conditions is not reduced as compared to the molecular weight of the factor D detected under the non-reducing conditions.

The position of the serine residue serving as the active center as a serine protease is position 335 in the amino acid sequence of SEQ ID NO: 1, position 317 in the amino acid sequence of SEQ ID NO: 2, position 335 in the amino acid sequence of SEQ ID NO: 3, position 317 in the amino acid sequence of SEQ ID NO: 4, position 348 in the amino acid sequence of SEQ ID NO: 5, position 320 in the amino acid sequence of SEQ ID NO: 6, position 335 in the amino acid sequence of SEQ ID NO: 7, position 317 in the amino acid sequence of SEQ ID NO: 8, position 337 in the amino acid sequence of SEQ ID NO: 9, position 319 in the amino acid sequence of SEQ ID NO: 10, position 350 in the amino acid sequence of SEQ ID NO: 11, position 322 in the amino acid sequence of SEQ ID NO: 12, position 350 in the amino acid sequence of SEQ ID NO: 32, position 322 in the amino acid sequence of SEQ ID NO: 33, position 335 in the amino acid sequence of SEQ ID NO: 67, position 318 in the amino acid sequence of SEQ ID NO: 68, position 334 in the amino acid sequence of SEQ ID NO: 69, and position 316 in the amino acid sequence of SEQ ID NO: 70. A protein in which one or multiple amino acid residues have been replaced, deleted, inserted, and/or added in the amino acid sequence of SEQ ID NO: 1 is preferably such that the amino acid residue at position 335 in the amino acid sequence of SEQ ID NO: 1 is an amino acid residue other than a serine residue. A protein in which one or multiple amino acid residues have been replaced, deleted, inserted, and/or added in the amino acid sequence of SEQ ID NO: 2 is preferably such that the amino acid residue at position 317 in the amino acid sequence of SEQ ID NO: 2 is an amino acid residue other than a serine residue. A protein in which one or multiple amino acid residues have been replaced, deleted, inserted, and/or added in the amino acid sequence of SEQ ID NO: 3 is preferably such that the amino acid residue at position 335 in the amino acid sequence of SEQ ID NO: 3 is an amino acid residue other than a serine residue. A protein in which one or multiple amino acid residues have been replaced, deleted, inserted, and/or added in the amino acid sequence of SEQ ID NO: 4 is preferably such that the amino acid residue at position 317 in the amino acid sequence of SEQ ID NO: 4 is an amino acid residue other than a serine residue. A protein in which one or multiple amino acid residues have been replaced, deleted, inserted, and/or added in the amino acid sequence of SEQ ID NO: 5 is preferably such that the amino acid residue at position 348 in the amino acid sequence of SEQ ID NO: 5 is an amino acid residue other than a serine residue. A protein in which one or multiple amino acid residues have been replaced, deleted, inserted, and/or added in the amino acid sequence of SEQ ID NO: 6 is preferably such that the amino acid residue at position 320 in the amino acid sequence of SEQ ID NO: 6 is an amino acid residue other than a serine residue. A protein in which one or multiple amino acid residues have been replaced, deleted, inserted, and/or added in the amino acid sequence of SEQ ID NO: 7 is preferably such that the amino acid residue at position 335 in the amino acid sequence of SEQ ID NO: 7 is an amino acid residue other than a serine residue. A protein in which one or multiple amino acid residues have been replaced, deleted, inserted, and/or added in the amino acid sequence of SEQ ID NO: 8 is preferably such that the amino acid residue at position 317 in the amino acid sequence of SEQ ID NO: 8 is an amino acid residue other than a serine residue. A protein in which one or multiple amino acid residues have been replaced, deleted, inserted, and/or added in the amino acid sequence of SEQ ID NO: 9 is preferably such that the amino acid residue at position 337 in the amino acid sequence of SEQ ID NO: 9 is an amino acid residue other than a serine residue. A protein in which one or multiple amino acid residues have been replaced, deleted, inserted, and/or added in the amino acid sequence of SEQ ID NO: 10 is preferably such that the amino acid residue at position 319 in the amino acid sequence of SEQ ID NO: 10 is an amino acid residue other than a serine residue. A protein in which one or multiple amino acid residues have been replaced, deleted, inserted, and/or added in the amino acid sequence of SEQ ID NO: 11 is preferably such that the amino acid residue at position 350 in the amino acid sequence of SEQ ID NO: 11 is an amino acid residue other than a serine residue. A protein in which one or multiple amino acid residues have been replaced, deleted, inserted, and/or added in the amino acid sequence of SEQ ID NO: 12 is preferably such that the amino acid residue at position 322 in the amino acid sequence of SEQ ID NO: 12 is an amino acid residue other than a serine residue. A protein in which one or multiple amino acid residues have been replaced, deleted, inserted, and/or added in the amino acid sequence of SEQ ID NO: 32 is preferably such that the amino acid residue at position 350 in the amino acid sequence of SEQ ID NO: 32 is an amino acid residue other than a serine residue. A protein in which one or multiple amino acid residues have been replaced, deleted, inserted, and/or added in the amino acid sequence of SEQ ID NO: 33 is preferably such that the amino acid residue at position 322 in the amino acid sequence of SEQ ID NO: 33 is an amino acid residue other than a serine residue. A protein in which one or multiple amino acid residues have been replaced, deleted, inserted, and/or added in the amino acid sequence of SEQ ID NO: 67 is preferably such that the amino acid residue at position 335 in the amino acid sequence of SEQ ID NO: 67 is an amino acid residue other than a serine residue. A protein in which one or multiple amino acid residues have been replaced, deleted, inserted, and/or added in the amino acid sequence of SEQ ID NO: 68 is preferably such that the amino acid residue at position 318 in the amino acid sequence of SEQ ID NO: 68 is an amino acid residue other than a serine residue. A protein in which one or multiple amino acid residues have been replaced, deleted, inserted, and/or added in the amino acid sequence of SEQ ID NO: 69 is preferably such that the amino acid residue at position 334 in the amino acid sequence of SEQ ID NO: 69 is an amino acid residue other than a serine residue. A protein in which one or multiple amino acid residues have been replaced, deleted, inserted, and/or added in the amino acid sequence of SEQ ID NO: 70 is preferably such that the amino acid residue at position 316 in the amino acid sequence of SEQ ID NO: 70 is an amino acid residue other than a serine residue.

A protein in which one or multiple amino acid residues have been replaced, deleted, inserted, and/or added in the amino acid sequence of SEQ ID NO: 1 is more preferably such that the amino acid residue at position 335 in the amino acid sequence of SEQ ID NO: 1 is a glycine residue. A protein in which one or multiple amino acid residues have been replaced, deleted, inserted, and/or added in the amino acid sequence of SEQ ID NO: 2 is more preferably such that the amino acid residue at position 317 in the amino acid sequence of SEQ ID NO: 2 is a glycine residue. A protein in which one or multiple amino acid residues have been replaced, deleted, inserted, and/or added in the amino acid sequence of SEQ ID NO: 3 is more preferably such that the amino acid residue at position 335 in the amino acid sequence of SEQ ID NO: 3 is a glycine residue. A protein in which one or multiple amino acid residues have been replaced, deleted, inserted, and/or added in the amino acid sequence of SEQ ID NO: 4 is more preferably such that the amino acid residue at position 317 in the amino acid sequence of SEQ ID NO: 4 is a glycine residue. A protein in which one or multiple amino acid residues have been replaced, deleted, inserted, and/or added in the amino acid sequence of SEQ ID NO: 5 is more preferably such that the amino acid residue at position 348 in the amino acid sequence of SEQ ID NO: 5 is a glycine residue. A protein in which one or multiple amino acid residues have been replaced, deleted, inserted, and/or added in the amino acid sequence of SEQ ID NO: 6 is more preferably such that the amino acid residue at position 320 in the amino acid sequence of SEQ ID NO: 6 is a glycine residue. A protein in which one or multiple amino acid residues have been replaced, deleted, inserted, and/or added in the amino acid sequence of SEQ ID NO: 7 is more preferably such that the amino acid residue at position 335 in the amino acid sequence of SEQ ID NO: 7 is a glycine residue. A protein in which one or multiple amino acid residues have been replaced, deleted, inserted, and/or added in the amino acid sequence of SEQ ID NO: 8 is more preferably such that the amino acid residue at position 317 in the amino acid sequence of SEQ ID NO: 8 is a glycine residue. A protein in which one or multiple amino acid residues have been replaced, deleted, inserted, and/or added in the amino acid sequence of SEQ ID NO: 9 is more preferably such that the amino acid residue at position 337 in the amino acid sequence of SEQ ID NO: 9 is a glycine residue. A protein in which one or multiple amino acid residues have been replaced, deleted, inserted, and/or added in the amino acid sequence of SEQ ID NO: 10 is more preferably such that the amino acid residue at position 319 in the amino acid sequence of SEQ ID NO: 10 is a glycine residue. A protein in which one or multiple amino acid residues have been replaced, deleted, inserted, and/or added in the amino acid sequence of SEQ ID NO: 11 is more preferably such that the amino acid residue at position 350 in the amino acid sequence of SEQ ID NO: 11 is a glycine residue. A protein in which one or multiple amino acid residues have been replaced, deleted, inserted, and/or added in the amino acid sequence of SEQ ID NO: 12 is more preferably such that the amino acid residue at position 322 in the amino acid sequence of SEQ ID NO: 12 is a glycine residue. A protein in which one or multiple amino acid residues have been replaced, deleted, inserted, and/or added in the amino acid sequence of SEQ ID NO: 32 is more preferably such that the amino acid residue at position 350 in the amino acid sequence of SEQ ID NO: 32 is a glycine residue. A protein in which one or multiple amino acid residues have been replaced, deleted, inserted, and/or added in the amino acid sequence of SEQ ID NO: 33 is more preferably such that the amino acid residue at position 322 in the amino acid sequence of SEQ ID NO: 33 is a glycine residue. A protein in which one or multiple amino acid residues have been replaced, deleted, inserted, and/or added in the amino acid sequence of SEQ ID NO: 67 is more preferably such that the amino acid residue at position 335 in the amino acid sequence of SEQ ID NO: 67 is a glycine residue. A protein in which one or multiple amino acid residues have been replaced, deleted, inserted, and/or added in the amino acid sequence of SEQ ID NO: 68 is more preferably such that the amino acid residue at position 318 in the amino acid sequence of SEQ ID NO: 68 is a glycine residue. A protein in which one or multiple amino acid residues have been replaced, deleted, inserted, and/or added in the amino acid sequence of SEQ ID NO: 69 is more preferably such that the amino acid residue at position 334 in the amino acid sequence of SEQ ID NO: 69 is a glycine residue. A protein in which one or multiple amino acid residues have been replaced, deleted, inserted, and/or added in the amino acid sequence of SEQ ID NO: 70 is more preferably such that the amino acid residue at position 316 in the amino acid sequence of SEQ ID NO: 70 is a glycine residue.

In the reagent for β-glucan measurement, the factor G is activated in the presence of a β-glucan to activate the proclotting enzyme. The factor G is not limited as long as it has the function of the factor G. Typically, the factor G is a heterodimer of an α-subunit having a binding ability to a β-glucan and a β-subunit having serine protease activity. The function of the factor G is a function of cleaving the proclotting enzyme in the presence of a β-glucan. The function of the factor G for a given protein can be confirmed by combining the protein with a functional factor D, the proclotting enzyme, and the substrate for measurement, and detecting the progress of the cascade reaction in the presence of a β-glucan.

The amino acid sequences of the α-subunit (SEQ ID NO: 13, GenBank: BAA04044.1) and the β-subunit (SEQ ID NO: 14, GenBank: BAA04045.1) of the factor G derived from *Tachypleus tridentatus*, and the α-subunit (SEQ ID NOS: 15 to 17) and the β-subunit (SEQ ID NOS: 18 to 23) of the factor G derived from *Limulus polyphemus* are shown in the sequence listing.

Preferably, the factor G is a protein selected from the group consisting of the following (3) to (5):

(3) a protein composed of an α-subunit containing the amino acid sequence of SEQ ID NO: 13 or an amino acid sequence obtained by cleaving the signal sequence from the amino acid sequence of SEQ ID NO: 13 and a β-subunit containing the amino acid sequence of SEQ ID NO: 14 or an amino acid sequence obtained by cleaving the signal sequence from the amino acid sequence of SEQ ID NO: 14;

(4) a protein composed of an α-subunit containing any one amino acid sequence selected from the group consisting of SEQ ID NOS: 15 to 17 or any one amino acid sequence among the amino acid sequences obtained by cleaving the signal sequence from the amino acid sequences of SEQ ID NOS: 15 to 17, and a β-subunit containing any one amino acid sequence selected from the group consisting of SEQ ID NOS: 18 to 23 or any one amino acid sequence among the amino acid sequences obtained by cleaving the signal sequence from the amino acid sequences of SEQ ID NOS: 18 to 23; and (5) a protein that contains an amino acid sequence in which one or multiple amino acid residues have been replaced, deleted, inserted, and/or added in the amino acid sequence of at least one of the α-subunit and the β-subunit in (3) or (4), and has the function of the factor G.

In the case of the amino acid sequence represented by SEQ ID NO: 13 or any of SEQ ID NOS: 15 to 17 described above, the "multiple" can be preferably 2 to 95, more preferably 2 to 60, even more preferably 2 to 30, and particularly preferably 2 to 5. Further, in the case of the amino acid sequence represented by SEQ ID NO: 14 or any of SEQ ID NOS: 18 to 23 described above, the "multiple" can be preferably 2 to 40, more preferably 2 to 25, even more preferably 2 to 12, and particularly preferably 2.

In the reagent for β-glucan measurement, the proclotting enzyme is activated by the active factor G to cleave the substrate for measurement. The proclotting enzyme is not limited as long as it has the function of the proclotting enzyme. The function of the proclotting enzyme is a function of cleaving the substrate for measurement in the presence of the active factor G. The function of the proclotting enzyme for a given protein can be confirmed by combining the protein with a functional factor D, the factor G, and the substrate for measurement, and detecting the progress of the cascade reaction in the presence of a β-glucan.

The amino acid sequences of the proclotting enzyme derived from *Tachypleus tridentatus* (SEQ ID NO: 24, GenBank: AAA30094.1), and the proclotting enzyme derived from *Limulus polyphemus* (SEQ ID NO: 25, NCBI Reference Sequence: XP_013783518.1) are shown in the sequence listing.

Preferably, the proclotting enzyme is a protein selected from the group consisting of the following (6) to (8):

(6) a protein that contains the amino acid sequence of SEQ ID NO: 24 or an amino acid sequence obtained by cleaving the signal sequence from the amino acid sequence of SEQ ID NO: 24;

(7) a protein that contains the amino acid sequence of SEQ ID NO: 25 or an amino acid sequence obtained by cleaving the signal sequence from the amino acid sequence of SEQ ID NO: 25; and (8) a protein, in which one or multiple amino acid residues have been replaced, deleted, inserted, and/or added in the amino acid sequence in (6) or (7), and which has the function of the proclotting enzyme.

In the case of the amino acid sequence represented by SEQ ID NO: 24 or 25 described above, the "multiple" can be preferably 2 to 50, more preferably 2 to 30, even more preferably 2 to 15, and particularly preferably 2 to 3.

The reagent for β-glucan measurement can contain an artificially produced glucan-related factor. A method for artificially producing a glucan-related factor is not particularly limited, and in addition to recombinant production, production by a peptide synthesizer, a production method by isolation from a horseshoe crab hemocyte extract, and the like can be exemplified. In one preferred embodiment, each glucan-related factor is a recombinant protein. In the reagent for β-glucan measurement, when an artificially produced glucan-related factor is used, the amount thereof used in the measurement system may be set, for example, with reference to a known reagent for β-glucan measurement using a horseshoe crab hemocyte extract.

The glucan-related factor may have an additional amino acid sequence such as a signal sequence or a tag at a terminal portion of the polypeptide by a conventional method. The signal sequence can be appropriately selected according to the type of a host cell used for recombinant production. Examples of the tag include a His tag, a FLAG tag, a c-myc tag, a protein A tag, an MBP tag, a GST tag, a V5 tag, a SUMO tag, a PA tag, and the like.

As a cascade that the proclotting enzyme is activated in a hemocyte extract, not only a pathway triggered by a β-glucan involving the factor G, but also a pathway triggered by an endotoxin involving the factor C and the factor B exists (FIG. 1). Therefore, from the viewpoint of preventing false positives due to the presence of an endotoxin, the reagent for β-glucan measurement preferably does not contain a horseshoe crab hemocyte extract. The fact that the reagent for β-glucan measurement does not contain a horseshoe crab hemocyte extract can be confirmed, for example, by the fact that even if an endotoxin is allowed to act on the reagent for β-glucan measurement, a significant enhancement of the cascade reaction (an enhancement of the cascade reaction for an endotoxin-free control sample) is not observed. Alternatively, the fact that the reagent for β-glucan measurement does not contain a horseshoe crab hemocyte extract can also be confirmed, for example, by the fact that no polynucleotide derived from the genomic DNA of a horseshoe crab hemocytes exists in the reagent for β-glucan measurement. The existence of the polynucleotide derived from the genomic DNA only needs to be analyzed by a technique well known to those skilled in the art, and it may be performed, for example, by amplifying the polynucleotide contained in the reagent for β-glucan measurement by a PCR method, and subjecting the obtained amplified fragment to a sequence analysis. The recombinant production of a glucan-related factor using an insect cell, a mammalian cell, or the like as a host, or the production by a peptide synthesizer is preferred because the glucan-related factor can be prepared without using a horseshoe crab hemocyte extract. Even if a reagent for endotoxin measurement containing a factor C is allowed to coexist with a factor D, no improvement of the performance of the reagent against an endotoxin is observed.

A recombinant protein of a glucan-related factor can be obtained, for example, by transforming a host cell with a gene encoding the amino acid sequence of each glucan-related factor and expressing the glucan-related factor. The nucleotide sequence of a gene encoding a glucan-related factor may be obtained from a known database such as NCBI (www.ncbi.nlm.nih.gov). The nucleotide sequence of a gene encoding a glucan-related factor may be a nucleic acid variant in which the codon combination has been optimized for expression in the host cell.

In an embodiment, the nucleotide sequence of a gene encoding the factor D is selected from the group consisting of the nucleotide sequences of SEQ ID NOS: 26 to 31, 34, 71, and 72 in the sequence listing.

In an embodiment, the nucleotide sequence of a gene encoding the factor D is selected from the group consisting of the nucleotide sequences of SEQ ID NOS: 26 to 31, and 34 in the sequence listing.

The gene encoding the amino acid sequence of each glucan-related factor is functionally linked to a vector by a known genetic engineering technique. For example, any two are selected from the restriction enzyme sites present in the multicloning site of a vector, and the vector and the nucleic acid of the invention are subjected to limited digestion with these restriction enzymes, followed by ligation, whereby the foreign gene can be functionally linked to the vector. Here, the "functionally linked" with respect to a gene refers to a state where the gene is linked to a promoter so as to receive transcription from the promoter.

The vector can be appropriately selected according to the type of host cell into which the vector is to be introduced. The "host cell" in this description does not include a horseshoe crab cell. For example, in a case where a eukaryotic cell such as an insect cell or a mammalian cell is used as the host, as the vector, for example, a plasmid such as pIZ-V5 (manufactured by Life Technologies Corporation), pCA7 (Takeda, M., et al. (2005) J. Virol. 79, 14346-54), or pCI-neo (manufactured by Promega Corporation) is exemplified.

As the host cell, an insect cell (such as an Sf9 cell), a mammalian cell (such as an HEK 293 cell or a CHO cell), or the like can be used. Preferably, a mammalian cell is used as the host.

The transformation of the host cell with an expression plasmid is carried out according to a usual method. For example, a calcium phosphate method, a lipofection method, a DEAE dextran method, an electroporation method, and a microinjection method are exemplified. The culturing of the host cell can be carried out under conditions commonly used for culturing the cell.

Each expressed glucan-related factor can be collected by a known method for protein extraction and purification. For example, in a case where the glucan-related factor is produced in a soluble form that is secreted into a culture supernatant, the culture supernatant is collected and can be used directly as the reagent. Further, in a case where the glucan-related factor is produced in a soluble form or in an insoluble form secreted into a cytoplasm, the glucan-related factor can be extracted using, for example, homogenization, a bead mill method, a sonication method, an osmotic shock method, a freeze-thaw method, extraction with a surfactant, or a combination thereof, or the like. From the viewpoint of production efficiency, it is preferred to collect the cell culture supernatant containing each expressed glucan-related factor. The glucan-related factor can be purified by a conventionally known method such as salting out, ammonium sulfate fractionation, centrifugation, dialysis, ultrafiltration, various types of chromatography, and a combination thereof.

In the reagent for β-glucan measurement, the substrate for measurement is cleaved by the activated proclotting enzyme in the presence of a β-glucan and used for detecting the progress of the cascade reaction. The substrate for measurement is a compound including a substrate for the activated proclotting enzyme (that is, a clotting enzyme). The substrate for measurement is not particularly limited as long as it is a substrate for the proclotting enzyme. The substrate for measurement may be, for example, a protein, a peptide, or a derivative thereof. As the protein to be used as the substrate for measurement, coagulogen, which is a substrate for the clotting enzyme is exemplified. Coagulogen can be prepared, for example, by fractionation from a hemocyte extract. Further, for example, it is also possible to prepare recombinant coagulogen by referring to the method described in the literature (Miyata et al., Protein, Nucleic Acid, Enzyme, Extra Issue, No. 29; pp. 30-43; 1986). The substrate for measurement may be, for example, a chemically synthesized one (synthetic substrate). The synthetic substrate is not particularly limited as long as it is a substrate suitable for measuring the progress of the cascade reaction. The synthetic substrate is preferably a derivative of a peptide.

In an embodiment, the reagent for β-glucan measurement in which the substrate for measurement is represented by the general formula Y—X—Z is provided, provided that in the general formula, Y is a hydrogen atom or a protecting group, X is a peptide containing the sequence of the substrate for the horseshoe crab-derived proclotting enzyme, and Z is a labeling substance. Such a synthetic substrate only needs to have a property that the covalent bond between X and Z is cleaved by the activated proclotting enzyme so as to release the labeling substance Z. In the general formula Y—X—Z, Y is preferably a protecting group for an amino group at the N-terminus of the peptide. In the general formula Y—X—Z, the bond between Y and X is preferably an amide bond formed between a carboxy group of the protecting group and the N-terminal α-amino group of the peptide. Further, in the general formula Y—X—Z, the bond between X and Z is preferably an amide bond formed between a carboxy group at the C-terminus of the peptide and an amino group of the labeling substance Z.

The protecting group used as Y is not particularly limited, and a known protecting group applicable to the protection of the peptide can be used. Examples of the protecting group include a tert-butoxycarbonyl group (Boc), a benzyloxycarbonyl group (Cbz), a benzyl group (Bzl), a benzoyl group (Bz), and an acetyl group (Ac).

The peptide (X) is not particularly limited as long as it is a peptide having an amino acid sequence that serves as a substrate for the activated proclotting enzyme. The peptide is preferably a substrate suitable for measuring a serine protease, more preferably a peptide having an Arg (R) residue or a Lys (K) residue at the C-terminus, and even more preferably a peptide having an Arg (R) residue at the C-terminus. Examples of the peptide having an Arg (R) residue at the C-terminus include Leu-Gly-Arg (LGR), Glu-Gly-Arg (EGR), Ile-Glu-Ala-Arg (IEAR), and Ile-Glu-Gly-Arg (IEGR). Among these, it is more preferred to contain an amino acid sequence represented by $A_1$-Gly-Arg (wherein $A_1$ is an arbitrary amino acid residue). Examples of the peptide having a Lys (K) residue at the C-terminus include Ile-Glu-Gly-Lys (IEGK).

The labeling substance (Z) is not particularly limited, and a known labeling substance applicable to the measurement of protease activity can be used. As the labeling substance, for example, a compound (optical labeling substance) that becomes capable of optical detection (for example, detection by color development, fluorescence, luminescence, or the like) when it is released from the peptide can be used. Examples of such a labeling substance include para-nitroaniline (pNA), 7-methoxycoumarin-4-acetic acid, 2,4-dinitroaniline (DNP), 7-amino-4-methylcoumarin (AMC), 7-amino-4-trifluoromethylcoumarin, and luciferin. Further, as the labeling substance, for example, a compound that can be detected by an electrochemical measurement method (such as voltammetry or amperometry) when it is released from the peptide can also be used. Examples of such a labeling substance include p-aminophenol (pAP), p-methoxyaniline (pMA), N-methyl-p-phenylenediamine (MPDD), and N,N'-dimethyl-p-phenylenediamine (DMPD). In a preferred embodiment, the reagent for β-glucan measurement in which the labeling substance is an optical labeling substance is provided.

The β-glucan to be measured with the reagent for β-glucan measurement has a (1→3)-β-D-polyglucoside structure, and other than a linear (1→3)-β-D-glucan, it may be a branched (1→3)-β-D-glucan having an intramolecular side chain such as (1→6)-β-D- or (1→4)-β-D-.

In a preferred embodiment, the reagent for β-glucan measurement in which the detection limit for pachyman to be used as a reference standard of (1→3)-β-D-glucan is 20 pg/mL or less within a reaction time of 60 minutes is provided. The detection limit for pachyman within a reaction time of 60 minutes is more preferably 16 pg/mL or less, even more preferably 5 pg/mL or less, and particularly preferably 1 pg/mL or less. In another embodiment, the reagent for β-glucan measurement in which the detection limit for pachyman within a reaction time of 40 minutes is preferably 20 pg/mL or less, more preferably 16 pg/mL or less, even more preferably 5 pg/mL or less, and particularly preferably 1 pg/mL or less is provided. Note that the above "reaction time" is a time from when the factor G, which is located most upstream of the cascade reaction, is brought into contact with the sample until when the final measurement value is obtained. The reaction is usually carried out at 37° C. As the pachyman, for example, a commercially available reagent can be used. The pachyman is preferably a β-glucan reference standard. Examples thereof include a β-glucan reference standard (pachyman) (Associates of Cape Cod, Inc., Nissui Pharmaceutical Co., Ltd., or the like).

The reagent for β-glucan measurement can contain any additive such as a buffer in addition to the glucan-related factors and the substrate for measurement. In the reagent for β-glucan measurement, each glucan-related factor and the substrate for measurement may be stored in separate containers, or any combination thereof may be stored in the same container. The form of the reagent for β-glucan measurement is not particularly limited, and may be, for example, a solution or a freeze-dried form.

In an embodiment, a method for enhancing the activity of the reagent for β-glucan measurement, including coexisting a horseshoe crab-derived factor D with the reagent for β-glucan measurement is provided. In this method, the horseshoe crab-derived factor D may coexist with the reagent for β-glucan measurement in advance before the sample and the reagent for β-glucan measurement react with each other. Alternatively, after starting the reaction between the sample and the reagent for β-glucan measurement, the horseshoe crab-derived factor D may be added to coexist. In this method, the reagent for β-glucan measurement with which the factor D coexists may be either one that contains a horseshoe crab hemocyte extract or one that does not contain a horseshoe crab hemocyte extract. For the β-glucan measurement method and the amount of the factor D to be used, the description of the application of the reagent for β-glucan measurement below is applied.

<Method for Producing Reagent for β-Glucan Measurement>

One embodiment of the invention relates to a method for producing a reagent for β-glucan measurement, including artificially producing a horseshoe crab-derived factor D.

In an embodiment, a method for producing a reagent for β-glucan measurement including artificially producing a horseshoe crab-derived factor D, and kitting the produced horseshoe crab-derived factor D together with at least a horseshoe crab-derived factor G, a horseshoe crab-derived proclotting enzyme, and a substrate for measurement is provided. The "kit" refers to an assembly including multiple components.

A method for artificially producing the horseshoe crab-derived factor D is not particularly limited, and in addition to recombinant production as described above, production by a peptide synthesizer, a production method by isolation from a horseshoe crab hemocyte extract, and the like can be exemplified. From the viewpoint of production efficiency, in one preferred embodiment, a method for producing a reagent for β-glucan measurement in which the artificial production of the horseshoe crab-derived factor D is recombinant production using a host cell is provided.

With respect to the horseshoe crab-derived factor D, the horseshoe crab-derived factor G, the horseshoe crab-derived proclotting enzyme, and the substrate for measurement used when forming a kit, the above description for the reagent for β-glucan measurement is applied.

Since the factor G is formed from two types of subunits, α and β, when the factor G is produced by a genetic recombination technique, it is preferred to use a single host cell transformed so as to express both subunits, and use the culture supernatant as a material of the reagent for β-glucan measurement from the viewpoint of production efficiency. The present inventors found a new problem that when a mammalian cell is used as the host, even if the cell is transformed with both of respective genes encoding the α-subunit and the β-subunit of *Limulus polyphemus*-derived factor G, the β-subunit is not secreted in the culture supernatant. Then, when *Tachypleus tridentatus*-derived genes were used as the respective genes to address this problem, a surprising result that both subunits α and β are secreted in the culture supernatant was obtained. This culture supernatant can be used as a material (raw material) of the reagent for β-glucan measurement as described above. Therefore, one aspect of the invention relates to a method for efficiently producing recombinant factor G using a mammalian cell. An embodiment relates to (1) a method for producing a material of a reagent for β-glucan measurement including culturing a mammalian cell transformed with both DNAs individually encoding *Tachypleus tridentatus*-derived factor G α-subunit and β-subunit, and collecting the culture supernatant after culturing. In the production of *Tachypleus tridentatus*-derived factor G, a CHO cell, particularly a CHO DG44 cell is preferred among mammalian cells. In one embodiment, the method includes culturing a mammalian cell transformed with a vector integrated with both DNAs individually encoding *Tachypleus tridentatus*-derived factor G α-subunit and β-subunit. In a preferred embodiment, the method further includes coexisting a *Limulus polyphemus*-derived proclotting enzyme in the culture supernatant. In another embodiment, a culture supernatant of a mammalian cell transformed with both DNAs individually encoding *Tachypleus tridentatus*-derived factor G α-subunit and β-subunit, is provided. In one preferred embodiment, a material of the reagent for β-glucan measurement, containing the culture supernatant is provided. In a preferred embodiment, the material of the reagent for β-glucan measurement further contains a *Limulus polyphemus*-derived proclotting enzyme. The "culture supernatant" in these embodiments contains the factor G (both α-subunit and β-subunit).

The reagent for β-glucan measurement may be kitted together with a dissolution solution, distilled water, a β-glucan reference standard, a microplate, a package insert describing product information, or the like.

<Application of Reagent for β-Glucan Measurement>

One embodiment of the invention relates to use of a reagent for β-glucan measurement containing a horseshoe crab-derived factor D.

In an embodiment, a β-glucan assay method including measuring a β-glucan in a sample using the above-mentioned reagent for β-glucan measurement or a reagent for β-glucan measurement produced by the above-mentioned method for producing a reagent for β-glucan measurement is provided. The assay method includes quantitative or qualitative determination for the presence or absence or the amount of a β-glucan in a sample. The β-glucan assay method can be carried out based on a conventional β-glucan assay method except that the above-mentioned reagent for β-glucan measurement or a reagent for β-glucan measurement produced by the above-mentioned method for producing a reagent for β-glucan measurement is used. The assay conditions are not limited, but for example, as the pH of the reaction solution, preferably 6.5 to 8.5 can be adopted. As the reaction temperature, for example, 30° C. to 40° C., preferably 37° C. can be adopted. The reaction time is also not particularly limited, but may be, for example, 5 minutes to 2 hours, preferably 30 minutes to 60 minutes. The amount of each glucan-related factor used in the reagent for β-glucan measurement may be appropriately adjusted according to the degree of activity.

In the assay method, each glucan-related factor, the substrate for measurement, the sample, and if used, another substance (such as a buffer) can be mixed in any order. The sample is not particularly limited, and examples thereof include biological samples such as blood, a body fluid, and a tissue; consumer goods such as water for injection, a pharmaceutical, an infusion, a medical device, a quasi-drug, a cosmetic, a food, and a reagent; environmental samples such as water and soil; and compounds such as a protein and a nucleic acid. The sample is preferably a biological sample, and more preferably blood.

For example, when coagulogen is used as the substrate for measurement, a β-glucan in the sample can be measured by turbidimetry.

When a synthetic substrate having a labeling substance is used as the substrate for measurement, a β-glucan in the sample can be measured using the labeling substance released from the substrate for measurement as an index. During the measurement using a synthetic substrate, the labeling substance in an amount (in moles) corresponding to the protease activity (total activity) of the proclotting enzyme activated by the β-glucan as a trigger is released from the substrate for measurement. The labeling substance released from the substrate for measurement can be measured by, for example, an optical analyzer such as a spectrophotometer or a fluorescence photometer, an electrochemical measurement apparatus such as a voltammeter or an amperometer, or the like depending on the type of labeling substance. For example, a β-glucan in the sample can be determined by comparing the measurement value obtained by measuring the sample with a blank value (a measurement value of a β-glucan free control sample). In the assay method, the cascade reaction is preferably carried out in an aqueous solvent.

The assay method may further include another optional step. The assay method may include, for example, a step of converting the obtained measurement value to another value. As the step of converting the measurement value to another value, for example, a step of calculating the amount of the β-glucan based on the measurement value is exemplified. Such a step is specifically, for example, a step of converting a measurement value obtained when measuring a sample to the amount of the β-glucan based on a relationship (standard curve) between the measurement value obtained when the sample is replaced with a standard substance with a known concentration and measurement is performed and the concentration of the standard substance.

In an embodiment, a test method for mycosis including performing the above-mentioned β-glucan assay method using a biological sample derived from a test subject suspected of having mycosis is provided.

In an embodiment, a data acquisition method for diagnosing mycosis including acquiring data for diagnosing whether a test subject has mycosis by performing the above-mentioned β-glucan assay method using a biological sample derived from the test subject is provided.

In this description, examples of the test subject include a human and a non-human animal (for example, a dog, a cat, a rabbit, a rat, a mouse, or the like), but the test subject is preferably a human.

When the presence of a β-glucan in the sample is observed by the above-mentioned β-glucan assay method, or when the amount of a β-glucan contained in the sample exceeds a preset cutoff value, the test subject can be diagnosed with or suspected of having mycosis. When the presence of a β-glucan in the sample is not observed, or when the amount of a β-glucan contained in the sample is equal to or less than a preset cutoff value, the test subject can be diagnosed as not having mycosis or with a low suspicion for mycosis (for example, follow-up).

EXAMPLES

Hereinafter, preferred embodiments of the invention will be described in more detail using Examples, but the technical scope of the invention is not limited to the following Examples.

Test Example 1

With reference to Muta et al. (The Journal of Biological Chemistry 270 (1995) 892-897), a fraction containing factor G (G fraction, not containing factor D) was collected from a *Tachypleus tridentatus* hemocyte extract.

With reference to Kawabata et al. (FEBS Letters 398 (1996) 146-150), a fraction containing factor D (SEQ ID NO: 2) (D fraction) was prepared from a *Tachypleus tridentatus* hemocyte extract. Subsequently, the D fraction was developed by SDS-PAGE and the gel was stained with CBB. As a result, while the band of the factor D (45 kDa) was detected, it was confirmed that the bands of the α-subunit and β-subunit of the factor G are not detected. In order to make sure, the N-terminal amino acid sequence of this 45 kDa protein (factor D) was confirmed with a protein sequencer. That is, after deblocking pyroglutamic acid at the N-terminus of the 45 kDa protein by degradation with Pfu Pyroglutamate Aminopeptidase (Takara Bio Inc.), the determined amino acid sequence was subjected to a BLAST search, and as a result, it matched with the amino acid sequence of the factor D derived from *Tachypleus tridentatus* (SEQ ID NO: 1; GenBank: BAA13312.1). Further, it was also consistent with the fact that the N-terminus of the factor D from which the signal sequence was removed was glutamic acid, and the N-terminus of the 45 kDa protein was blocked. In addition, the amino acid sequence determined by degrading the internal sequence of the 45 kDa protein with a protease also matched with the reported factor D sequence.

A reagent for β-glucan measurement was prepared using each of the G fraction, the D fraction, and a mixture of the G fraction and the D fraction (G+D fraction). That is, a reagent for β-glucan measurement was prepared using each fraction together with a *Tachypleus tridentatus*-derived proclotting enzyme (a recombinant protein prepared in an insect cell in accordance with Examples in WO2012/118226) and a substrate for measurement (a synthetic substrate: Boc-LGR-pNA). This reagent was mixed with a specimen containing a β-glucan (pachyman; Associates of Cape Cod, Inc.) (the final concentration of the β-glucan: 90 pg/mL) to react therewith with reference to the method described in Examples in PATENT LITERATURE 3 (provided that the reaction was performed at 37° C. for 60 minutes), and the absorbance (405 nm) was measured.

Figure 2:
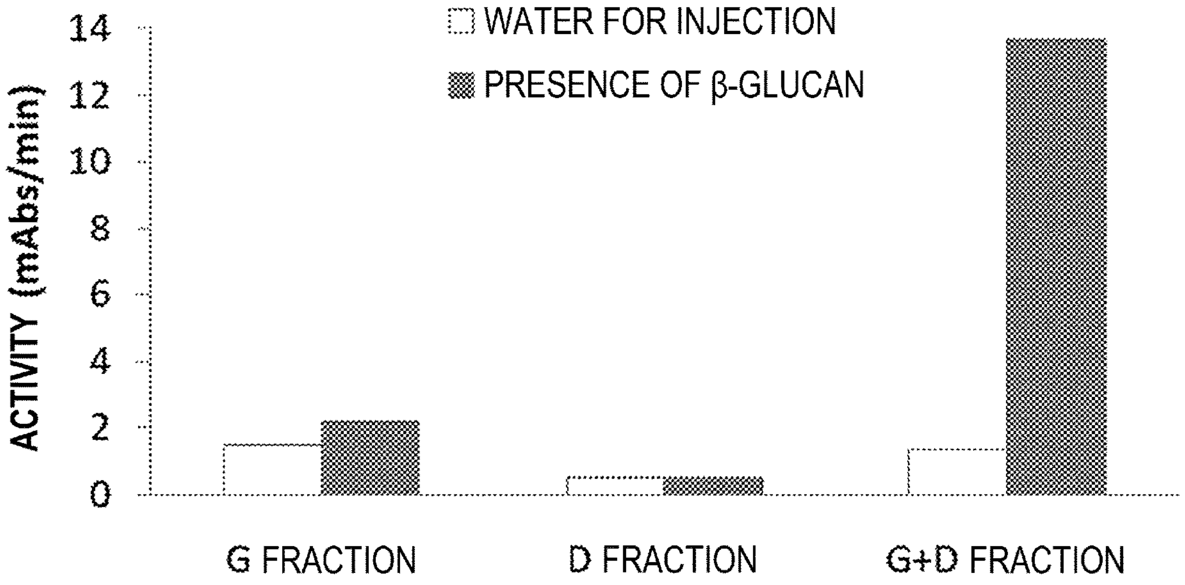
FIG. 2 shows the results of β-glucan measurement in the presence and absence of factor D.

The activity of the proclotting enzyme was calculated by dividing the measured absorbance (mAbs) by the time (minutes). The results are shown in FIG. 2. In the case of the reagent for β-glucan measurement using the G fraction, the activity of the proclotting enzyme was significantly low. Further, in the case of the reagent for β-glucan measurement using the D fraction, the progress of the cascade reaction was not observed. On the other hand, in the case of the reagent for β-glucan measurement using the G+D fraction, significant activation of the proclotting enzyme was observed.

From the above results, it was confirmed that by adding the horseshoe crab-derived factor D to the reagent for β-glucan measurement containing the horseshoe crab-derived factor G, the horseshoe crab-derived proclotting enzyme, and the substrate for measurement, the cascade reaction triggered by the β-glucan is significantly promoted.

Test Example 2

With reference to the description of Examples in WO2014/092079, an expression plasmid was constructed by integrating a gene encoding a *Limulus polyphemus*-derived proclotting enzyme (SEQ ID NO: 25) into a vector in place of the gene encoding *Tachypleus tridentatus*-derived factor C. A CHO DG44 cell transformed with this expression plasmid was cultured in the presence of methotrexate with reference to the description of Examples in WO2014/092079, and then monocloned. The obtained monoclonal cell line was cultured in a serum-free medium. This culture supernatant containing the *Limulus polyphemus*-derived proclotting enzyme recombinant protein was used as a material (raw material) for producing the below-mentioned reagent for β-glucan measurement.

With reference to the description of Examples in WO2014/092079, an expression plasmid was constructed by integrating genes encoding *Limulus polyphemus*-derived factor G α-subunit and β-subunit (SEQ ID NOS: 15 and 23) into a vector in place of the gene encoding *Tachypleus tridentatus*-derived factor C. A CHO DG44 cell was transformed with this expression plasmid. As a result of Western blotting, the β-subunit was not detected in the culture supernatant.

An expression plasmid was constructed by integrating genes encoding *Tachypleus tridentatus*-derived factor G α-subunit and β-subunit (SEQ ID NOS: 13 and 14) into a vector in place of the gene encoding *Limulus polyphemus*-derived factor G described above. A CHO DG44 cell was transformed with this expression plasmid. As a result of Western blotting, the α-subunit and β-subunit were detected in the culture supernatant. Subsequently, the transformed cell was cultured in the presence of methotrexate with reference to the description of Examples in WO2014/092079, and then monocloned. The obtained monoclonal cell line was cultured in a serum-free medium. This culture supernatant containing the *Tachypleus tridentatus*-derived factor G recombinant protein was used as a material (raw material) for producing the below-mentioned reagent for β-glucan measurement.

A reagent was prepared using the obtained proclotting enzyme recombinant protein, the factor G recombinant protein, and a substrate for measurement (a synthetic substrate: Boc-LGR-pNA). This reagent was mixed with a specimen containing a β-glucan (curdlan, manufactured by Wako Pure Chemical Industries, Ltd.) (the final concentration of the β-glucan: 200 pg/mL) to react therewith with reference to the method described in Examples in PATENT LITERATURE 3 (provided that the reaction was performed at 37° C. for 40 minutes), and the absorbance (405 nm) was measured. A similar measurement was performed using a specimen (blank) that does not contain the β-glucan.

Assuming that the proclotting enzyme activity of the blank was 1, the relative activity when the β-glucan was used as the specimen was calculated to be 1.1. That is, activation of the proclotting enzyme was almost not observed.

Test Example 3

The gene of the factor D was cloned by PCR using a *Tachypleus tridentatus* hemocyte-derived mRNA as a template. In the amino acid sequence (SEQ ID NO: 3) of the obtained factor D, one mutation (serine at position 373 in SEQ ID NO: 1 was replaced with alanine) was confirmed in the amino acid sequence of the reported amino acid sequence (SEQ ID NO: 1).

A *Tachypleus tridentatus*-derived factor D recombinant protein was prepared. Specifically, pCA7 was used as a vector, and an expression plasmid was prepared by integrating a gene (SEQ ID NO: 28) encoding the amino acid sequence of SEQ ID NO: 5 (TFD) therein. The amino acid sequence of SEQ ID NO: 5 is a sequence in which the signal sequence of the amino acid sequence of SEQ ID NO: 3 cloned above was replaced with a signal sequence derived from tyrosine phosphatase that is widely used in expression using a mammalian cell, and further a His tag was added to the C-terminus.

A *Limulus polyphemus*-derived factor D recombinant protein was prepared. Specifically, pCA7 was used as a vector, and an expression plasmid in which a gene (SEQ ID NO: 31) encoding the amino acid sequence of SEQ ID NO: 11 (LFD) was integrated therein was prepared. The LFD is an amino acid sequence in which the signal sequence of the amino acid sequence of XP_013794271.1 (SEQ ID NO: 9) registered in NCBI as *Limulus polyphemus*-derived factor D was replaced with a signal sequence derived from tyrosine phosphatase that is widely used in expression using a mammalian cell, and further a His tag was added to the C-terminus.

By using each of the expression plasmids prepared as described above, cells were cultured using Expi CHO Expression System (Thermo Fisher Scientific). The culture supernatant was collected as a sample, and by Western blotting using an anti-His tag antibody, it was confirmed that the factor D recombinant proteins (TFD and LFD) were extracellularly secreted.

Reagents for β-glucan measurement were prepared using each of the factor D recombinant proteins (TFD and LFD) collected as described above together with the factor G recombinant protein, the proclotting enzyme recombinant protein, and the substrate for measurement in the same manner as in Test Example 2. By using these reagents, an assay was performed in the same manner as in Test Example 2, and the relative activity to the blank when the β-glucan was used as the specimen was calculated in the same manner as in Test Example 2.

As a result, significant activation of the proclotting enzyme due to the presence of the β-glucan was observed in both reagents (the relative activity of the reagent for β-glucan measurement containing TFD was 21.0, and the relative activity of the reagent for β-glucan measurement containing LFD was 21.5). That is, it was possible to confirm that TFD and LFD significantly enhance the cascade reaction triggered by the β-glucan of the reagent for β-glucan measurement.

Test Example 4

A reagent for β-glucan measurement (recombinant reagent) containing LFD was prepared in the same manner as in Test Example 3, and its practicality was evaluated. At that time, the addition amount of the culture supernatant containing LFD was set to 2% (v/v) or 4% (v/v) with respect to the whole reagent. Subsequently, a calibration curve was created using a β-glucan reference standard (pachyman) attached to Glucatell (registered trademark, Associates of Cape Cod, Inc.), which is a reagent for β-glucan measurement using a horseshoe crab hemocyte extract. The reaction conditions (37° C., 40 minutes) and the volume of the reaction solution (100 μL of reagent+25 μL of specimen) followed the conditions described in the package insert of Glucatell (registered trademark).

Figure 3:
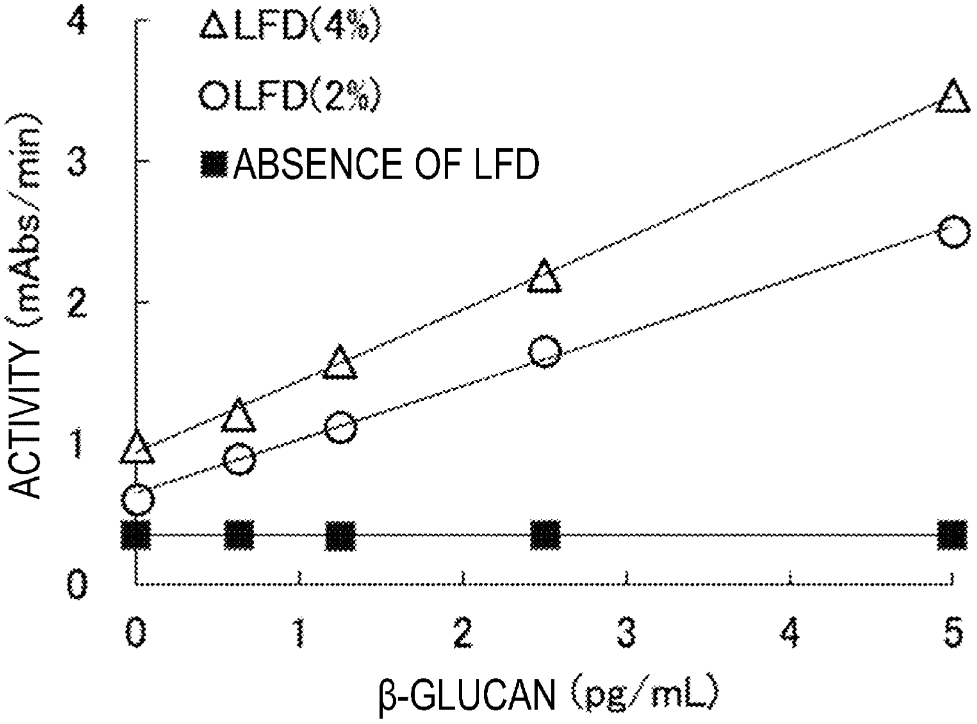
FIG. 3 shows the results of β-glucan measurement in the presence and absence of recombinant factor D.

As a result, the recombinant reagent could create a calibration curve in the range of 0.6 pg/mL to 5.0 pg/mL, and was possible to confirm to have the same sensitivity as Glucatell (registered trademark) (FIG. 3). At that time, activation of the proclotting enzyme by the β-glucan could not be observed in the case of the reagent of Test Example 2, which did not use the factor D, and the β-glucan was impossible to be quantified (FIG. 3).

Test Example 5

By using the expression plasmid for *Tachypleus tridentatus*-derived factor G prepared in Test Example 2, the factor G α-subunit and β-subunit (SEQ ID NOS: 13 and 14) were expressed using Expi CHO Expression System (Thermo Fisher Scientific). This culture supernatant containing the *Tachypleus tridentatus*-derived factor G recombinant protein was used as a material (raw material) for producing the below-mentioned reagent for β-glucan measurement.

A *Limulus polyphemus*-derived factor D recombinant protein was prepared. Specifically, pCI-neo was used as a vector, and an expression plasmid was prepared by integrating a gene (SEQ ID NO: 34) encoding the amino acid sequence of SEQ ID NO: 32 (LFD2) therein. The amino acid sequence of SEQ ID NO: 32 is a sequence in which the signal sequence of the amino acid sequence of XP_013794271.1 (SEQ ID NO: 9) registered in NCBI as *Limulus polyphemus*-derived factor D was replaced with a signal sequence derived from tyrosine phosphatase that is widely used in expression using a mammalian cell.

By using the expression plasmid prepared as described above, the factor D recombinant protein (LFD2) was expressed using Expi CHO Expression System (Thermo Fisher Scientific) The culture supernatant was collected as a sample, and by Western blotting, it was confirmed that the factor D recombinant protein (LFD2) was extracellularly secreted.

A reagent for β-glucan measurement was prepared using the factor D recombinant protein (LFD2) collected as described above together with the *Tachypleus tridentatus*-derived factor G recombinant protein, a *Tachypleus tridentatus*-derived proclotting enzyme (a recombinant protein prepared in an insect cell in accordance with Examples in WO2012/118226), and a substrate for measurement (a synthetic substrate: Boc-LGR-pNA). This reagent was mixed with a specimen containing a β-glucan (curdlan, manufactured by Wako Pure Chemical Industries, Ltd.) (the final concentration of the β-glucan: 100 pg/mL) to react therewith with reference to the method described in Examples in PATENT LITERATURE 3 (provided that the reaction was performed at 37° C. for 60 minutes), and the absorbance (405 nm) was measured. Further, a similar measurement was performed using a specimen (blank) that does not contain the β-glucan.

Assuming that the proclotting enzyme activity of the blank was 1, the relative activity when the β-glucan was used as the specimen was calculated. As a result, the relative activity of the reagent for β-glucan measurement that does not contain the factor D was 1.1. That is, activation of the proclotting enzyme was almost not observed. On the other hand, in the case of the reagent for β-glucan measurement containing LFD2, significant activation of the proclotting enzyme was observed (the relative activity was 13.0). That is, it was possible to confirm that LFD2 significantly enhances the cascade reaction triggered by the β-glucan of the reagent for β-glucan measurement.

Test Example 6

Each of a culture supernatant containing *Limulus polyphemus*-derived proclotting enzyme recombinant protein and a culture supernatant containing *Tachypleus tridentatus*-derived factor G recombinant protein was prepared in the same manner as in Test Example 2.

With reference to the description of Examples in WO2014/092079, a CHO DG44 cell transformed with the expression plasmid prepared in Test Example 5 was monocloned and cultured in a serum-free medium. The culture supernatant was collected as a sample, and by Western blotting, it was confirmed that the factor D recombinant protein (LFD2) was extracellularly secreted.

A reagent for β-glucan measurement was prepared using the factor D recombinant protein (LFD2) collected as described above together with the factor G recombinant protein, the proclotting enzyme recombinant protein, and the substrate for measurement in the same manner as in Test Example 2. Subsequently, a calibration curve was created using a β-glucan (pachyman, Associates of Cape Cod, Inc., the final concentration of the β-glucan: 0 to 20 pg/mL) in the same manner as in Test Example 4.

Figure 4:
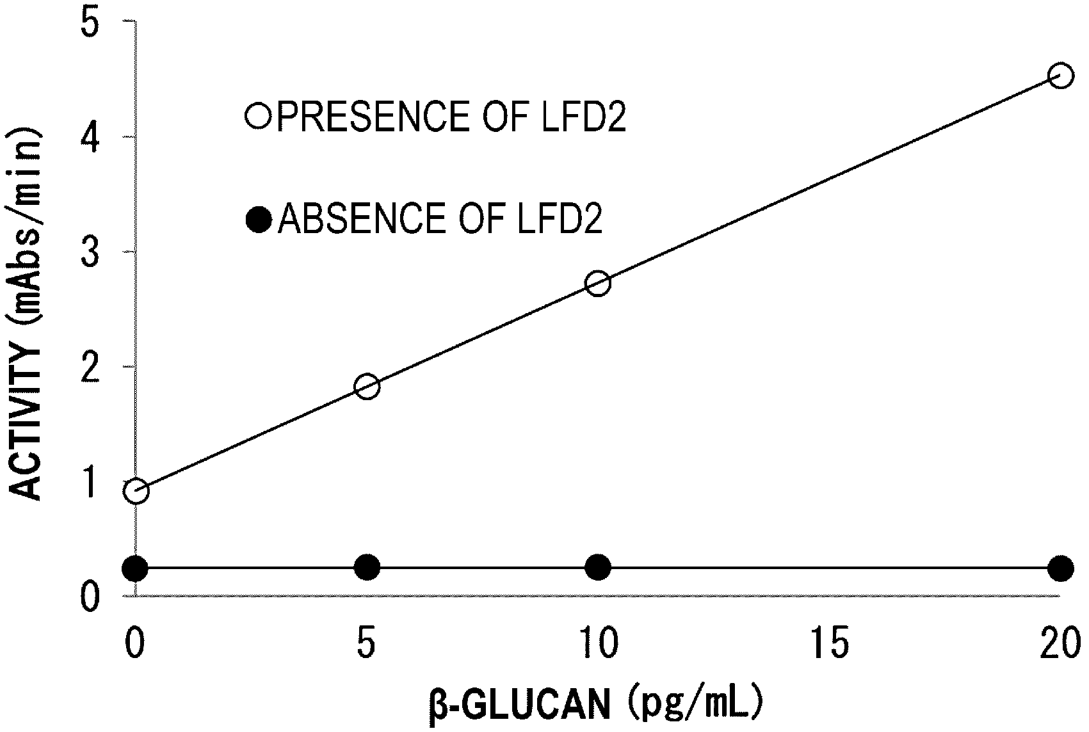
FIG. 4 shows the results of β-glucan measurement in the presence and absence of recombinant factor D.

As a result, it was possible to create a calibration curve within the concentration range of the β-glucan described above (FIG. 4). In the case of the reagent which does not use LFD2, activation of the proclotting enzyme by the β-glucan could not be observed, and the β-glucan could not be quantified (FIG. 4).

Test Example 7

A fraction containing the factor G of *Limulus polyphemus* was obtained by separating a hemocyte extract by column chromatography. It was confirmed by Western blotting that the obtained fraction does not contain the factor D or the proclotting enzyme.

A reagent for β-glucan measurement containing LFD was prepared using the fraction obtained above as the *Limulus polyphemus*-derived factor G in place of the *Tachypleus tridentatus*-derived factor G recombinant protein in Test Example 3. This reagent was mixed with a specimen containing a β-glucan (pachyman, Nissui Pharmaceutical Co., Ltd.) (the final concentration of the β-glucan: 20 pg/mL) to react therewith at 37° C. for 30 minutes, and then, the absorbance (405 nm) was measured. The activity of the proclotting enzyme was calculated by dividing the measured absorbance (mAbs) by the time (minutes). Further, a similar measurement was performed using a specimen (blank) that does not contain the β-glucan.

Assuming that the proclotting enzyme activity of the blank was 1, the relative activity when the β-glucan was used as the specimen was calculated. As a result, the relative activity of the reagent for β-glucan measurement that does not contain the factor D was 1.1. That is, activation of the proclotting enzyme was almost not observed. On the other hand, in the case of the reagent for β-glucan measurement containing LFD, significant activation of the proclotting enzyme was observed (the relative activity was 7.0). That is, it was possible to confirm that LFD significantly enhances the cascade reaction triggered by the β-glucan of the reagent for β-glucan measurement.

Test Example 8

With reference to the description of Examples (paragraphs [0113] to [0115]) in WO2014/092079, a HEK 293 GnTI$^-$ cell transformed with the expression plasmid prepared in Test Example 5 was cultured. The culture supernatant was collected as a sample, and by Western blotting, it was confirmed that the factor D recombinant protein (LFD2) was extracellularly secreted.

A reagent for β-glucan measurement was prepared using the factor D recombinant protein (LFD2) collected as described above together with the factor G recombinant protein, the proclotting enzyme recombinant protein, and the substrate for measurement in the same manner as in Test Example 2. This reagent was mixed with a specimen containing a β-glucan (pachyman, Nissui Pharmaceutical Co., Ltd.) (the final concentration of the β-glucan: 20 pg/mL) to react therewith at 37° C. for 40 minutes, and then, the absorbance (405 nm) was measured. The activity of the proclotting enzyme was calculated by dividing the measured absorbance (mAbs) by the time (minutes). Further, a similar measurement was performed using a specimen (blank) that does not contain the β-glucan.

Assuming that the proclotting enzyme activity of the blank was 1, the relative activity when the β-glucan was used as the specimen was calculated. As a result, the relative activity of the reagent for β-glucan measurement that does not contain the factor D was 1.1. That is, activation of the proclotting enzyme was almost not observed. On the other hand, in the case of the reagent for β-glucan measurement containing LFD2, significant activation of the proclotting enzyme was confirmed (the relative activity was 6.8). That is, it was possible to confirm that LFD2 significantly enhances the cascade reaction triggered by the β-glucan of the reagent for β-glucan measurement.

Test Example 9

A reagent for β-glucan measurement containing LFD was prepared in the same manner as in Test Example 3 except that the substrate for measurement was changed to Ac-IEAR-pNA (Biorbyt Ltd.). This reagent was mixed with a specimen containing a β-glucan (pachyman, Associates of Cape Cod, Inc.) (the final concentration of the β-glucan: 20 pg/mL) to react therewith at 37° C. for 40 minutes, and then, the absorbance (405 nm) was measured. The activity of the proclotting enzyme was calculated by dividing the measured absorbance (mAbs) by the time (minutes). Further, a similar measurement was performed using a specimen (blank) that does not contain the β-glucan.

Assuming that the proclotting enzyme activity of the blank was 1, the relative activity when the β-glucan was used as the specimen was calculated. As a result, the relative activity of the reagent for β-glucan measurement that does not contain the factor D was 1.1. That is, activation of the proclotting enzyme was almost not observed. On the other hand, in the case of the reagent for β-glucan measurement containing LFD, significant activation of the proclotting enzyme was confirmed (the relative activity was 5.9). That is, it was possible to confirm that LFD significantly enhances the cascade reaction triggered by the β-glucan of the reagent for β-glucan measurement.

Test Example 10

A reagent for β-glucan measurement (recombinant reagent) containing LFD was prepared in the same manner as in Test Example 3. This reagent (160 μL) was mixed with a specimen (40 μL) containing a β-glucan (lentinan, manufactured by Ajinomoto Co., Inc.) (the final concentration of the β-glucan: 0 to 5 pg/mL) to react therewith at 37° C. for 60 minutes, and then, the absorbance (405 nm) was measured. The activity of the proclotting enzyme was calculated by dividing the measured absorbance (mAbs) by the time (minutes). Further, a similar measurement was performed using a specimen (blank) that does not contain the β-glucan.

Figure 5:
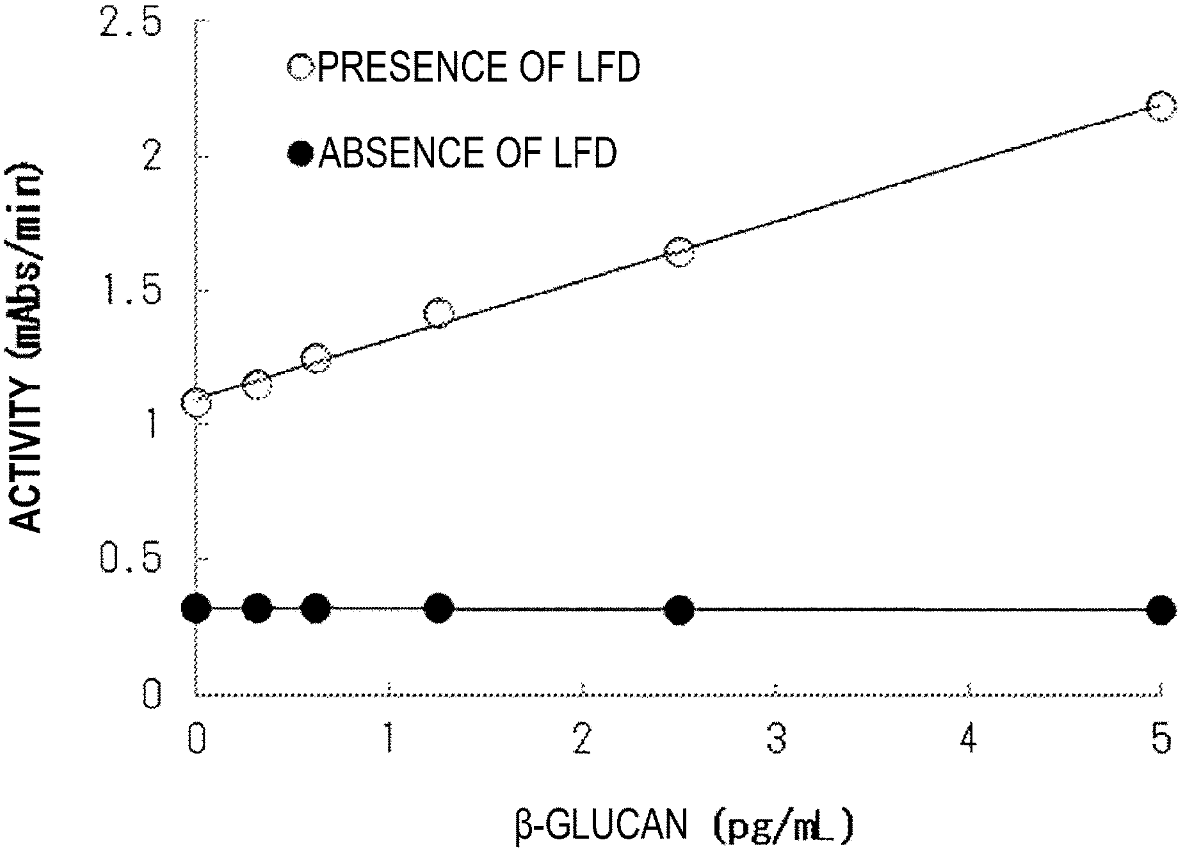
FIG. 5 shows the results of β-glucan measurement in the presence and absence of recombinant factor D.

As a result, it was possible to create a calibration curve within the concentration range of the β-glucan described above (FIG. 5). In the case of the reagent which does not use LFD, activation of the proclotting enzyme by the β-glucan could not be observed, and the β-glucan could not be quantified (FIG. 5).

Test Example 11

A total of four types of factor D recombinant proteins were produced: two types were derived from *Tachypleus tridentatus* and two types were derived from *Limulus polyphemus*. Specifically, four types of expression plasmids were prepared by integrating a gene encoding the amino acid sequence of SEQ ID NO: 1 (TFD2), a gene encoding the amino acid sequence of SEQ ID NO: 3 (TFD3), a gene encoding the amino acid sequence of SEQ ID NO: 7 (LFD3), or a gene encoding the amino acid sequence of SEQ ID NO: 9 (LFD4) into a vector (pCI-neo).

By using the expression plasmids prepared as described above, four types of factor D recombinant proteins were expressed using Expi CHO Expression System (Thermo Fisher Scientific). The culture supernatants were each collected as a sample, and by Western blotting, it was confirmed that each factor D recombinant protein was extracellularly secreted.

TFD2 is BAA13312.1 registered in NCBI as *Tachypleus tridentatus*-derived factor D. TFD3 is encoded by a cDNA (SEQ ID NO: 27) cloned from *Tachypleus tridentatus*. LFD3 is XP_013794266.1 registered in NCBI as *Limulus polyphemus*-derived factor D. LFD4 is XP_013794271.1 registered in NCBI as *Limulus polyphemus*-derived factor D.

A reagent for β-glucan measurement was prepared using each of the obtained four types of factor D recombinant proteins (TFD2, TFD3, LFD3, and LFD4) together with the proclotting enzyme recombinant protein, the factor G recombinant protein, and a substrate for measurement (a synthetic substrate: Boc-LGR-pNA) in the same manner as in Test Example 2. This reagent was mixed with a specimen containing a β-glucan (pachyman, Nissui Pharmaceutical Co., Ltd.) (the final concentration of the β-glucan: 20 pg/mL) to react therewith with reference to the method described in Examples in PATENT LITERATURE 3 (provided that the reaction was performed at 37° C. for 40 minutes), and the absorbance (405 nm) was measured. Further, a similar measurement was performed using a specimen (blank) that does not contain the β-glucan.

Assuming that the proclotting enzyme activity of the blank was 1, the relative activity when the β-glucan was used as the specimen was calculated. As a result, the relative activity of the reagent for β-glucan measurement that does not contain the factor D was 1.1. That is, activation of the proclotting enzyme was almost not observed. On the other hand, in the case of the reagent for β-glucan measurement containing the factor D recombinant protein, significant activation of the proclotting enzyme was confirmed (the relative activity was 17.5 when using TFD2, 7.2 when using TFD3, 6.4 when using LFD3, and 11.6 when using LFD4). That is, it was possible to confirm that TFD2, TFD3, LFD3, and LFD4 significantly enhance the cascade reaction triggered by the β-glucan of the reagent for β-glucan measurement.

Test Example 12

A reagent for β-glucan measurement containing LFD was prepared in the same manner as in Test Example 3 except that the substrate for measurement was changed to Ac-IEGK-pNA. This reagent was mixed with a specimen containing a β-glucan (pachyman, Associates of Cape Cod, Inc.) (the final concentration of the β-glucan: 20 pg/mL) to react therewith at 37° C. for 40 minutes, and then, the absorbance (405 nm) was measured. The activity of the proclotting enzyme was calculated by dividing the measured absorbance (mAbs) by the time (minutes). Further, a similar measurement was performed using a specimen (blank) that does not contain the β-glucan.

Assuming that the proclotting enzyme activity of the blank was 1, the relative activity when the β-glucan was used as the specimen was calculated. As a result, the relative activity of the reagent for β-glucan measurement that does not contain the factor D was 1.2. That is, activation of the proclotting enzyme was almost not observed. On the other hand, in the case of the reagent for β-glucan measurement containing LFD, significant activation of the proclotting enzyme was observed (the relative activity was 5.4). That is, it was possible to confirm that LFD significantly enhances the cascade reaction triggered by the β-glucan of the reagent for β-glucan measurement.

INDUSTRIAL APPLICABILITY

According to the invention, use of factor D as a main factor that makes up a reaction system together with other glucan-related factors in a limulus reaction triggered by a β-glucan is provided. That is, according to the invention, a high-performance recombinant reagent for β-glucan measurement can be provided. In addition, according to the invention, enhancement of the activity of the reagent for β-glucan measurement can be achieved.

The invention can be expected to be used permanently and widely as a tool for safety evaluation of water for injection, pharmaceuticals, medical devices, or the like, serodiagnosis of fungal infection or the like, or detection of microbial contamination in the field of environment and food hygiene by detection or quantification of a β-glucan, or as a reagent for research, or the like.

While the invention has been described in connection with specific Examples and various embodiments, it should be readily understood by those skilled in the art that many modifications and adaptations of the embodiments described herein are possible without departing from the spirit and scope of the invention.

This application claims priority based on Japanese Patent Application No. 2021-128613 filed in the Japan Patent Office dated Aug. 4, 2021, Japanese Patent Application No. 2021-175670 filed in the Japan Patent Office dated Oct. 27, 2021, and Japanese Patent Application No. 2022-10643 filed in the Japan Patent Office dated Jan. 27, 2022, the contents of which are incorporated herein by reference in their entirety.

<Description of Sequence Listing>

SEQ ID NO: 1: amino acid sequence 1 of *Tachypleus tridentatus*-derived factor D (TFD2)

SEQ ID NO: 2: amino acid sequence 1 of *Tachypleus tridentatus*-derived factor D (TFD2 (mature))

SEQ ID NO: 3: amino acid sequence 2 of *Tachypleus tridentatus*-derived factor D (TFD3)

SEQ ID NO: 4: amino acid sequence 2 of *Tachypleus tridentatus*-derived factor D (TFD3 (mature))

SEQ ID NO: 5: amino acid sequence 3 of *Tachypleus tridentatus*-derived factor D (TFD)

SEQ ID NO: 6: amino acid sequence 3 of *Tachypleus tridentatus*-derived factor D (TFD (mature))

SEQ ID NO: 7: amino acid sequence 1 of *Limulus polyphemus*-derived factor D (LFD3)

SEQ ID NO: 8: amino acid sequence 1 of *Limulus polyphemus*-derived factor D (LFD3 (mature))

SEQ ID NO: 9: amino acid sequence 2 of *Limulus polyphemus*-derived factor D (LFD4)

SEQ ID NO: 10: amino acid sequence 2 of *Limulus polyphemus*-derived factor D (LFD4 (mature))

SEQ ID NO: 11: amino acid sequence 3 of *Limulus polyphemus*-derived factor D (LFD)

SEQ ID NO: 12: amino acid sequence 3 of *Limulus polyphemus*-derived factor D (LFD (mature))

SEQ ID NO: 13: amino acid sequence of *Tachypleus tridentatus*-derived factor G α-subunit SEQ ID NO: 14: amino acid sequence of *Tachypleus tridentatus*-derived factor G β-subunit SEQ ID NO: 15: amino acid sequence 1 of *Limulus polyphemus*-derived factor G α-subunit SEQ ID NO: 16: amino acid sequence 2 of *Limulus polyphemus*-derived factor G α-subunit SEQ ID NO: 17: amino acid sequence 3 of *Limulus polyphemus*-derived factor G α-subunit SEQ ID NO: 18: amino acid sequence 1 of *Limulus polyphemus*-derived factor G β-subunit SEQ ID NO: 19: amino acid sequence 2 of *Limulus polyphemus*-derived factor G β-subunit SEQ ID NO: 20: amino acid sequence 3 of *Limulus polyphemus*-derived factor G β-subunit SEQ ID NO: 21: amino acid sequence 4 of *Limulus polyphemus*-derived factor G β-subunit SEQ ID NO: 22: amino acid sequence 5 of *Limulus polyphemus*-derived factor G β-subunit SEQ ID NO: 23: amino acid sequence 6 of *Limulus polyphemus*-derived factor G β-subunit SEQ ID NO: 24: amino acid sequence of *Tachypleus tridentatus*-derived proclotting enzyme SEQ ID NO: 25: amino acid sequence of *Limulus polyphemus*-derived proclotting enzyme SEQ ID NO: 26: nucleotide sequence 1 of *Tachypleus tridentatus*-derived factor D SEQ ID NO: 27: nucleotide sequence 2 of *Tachypleus tridentatus*-derived factor D SEQ ID NO: 28: nucleotide sequence 3 of *Tachypleus tridentatus*-derived factor D SEQ ID NO: 29: nucleotide sequence 1 of *Limulus polyphemus*-derived factor D SEQ ID NO: 30: nucleotide sequence 2 of *Limulus polyphemus*-derived factor D SEQ ID NO: 31: nucleotide sequence 3 of *Limulus polyphemus*-derived factor D SEQ ID NO: 32: amino acid sequence 4 of *Limulus polyphemus*-derived factor D (LFD2)

SEQ ID NO: 33: amino acid sequence 4 of *Limulus polyphemus*-derived factor D (LFD2 (mature))

SEQ ID NO: 34: nucleotide sequence 4 of *Limulus polyphemus*-derived factor D

SEQ ID NO: 35: amino acid sequence 4 of *Tachypleus tridentatus*-derived factor D SEQ ID NO: 36: amino acid sequence 5 of *Tachypleus tridentatus*-derived factor D SEQ ID NO: 37: amino acid sequence 6 of *Tachypleus tridentatus*-derived factor D SEQ ID NO: 38: amino acid sequence 7 of *Tachypleus tridentatus*-derived factor D SEQ ID NO: 39: amino acid sequence 8 of *Tachypleus tridentatus*-derived factor D SEQ ID NO: 40: amino acid sequence 9 of *Tachypleus tridentatus*-derived factor D SEQ ID NO: 41: amino acid sequence 10 of *Tachypleus tridentatus*-derived factor D SEQ ID NO: 42: amino acid sequence 11 of *Tachypleus tridentatus*-derived factor D SEQ ID NO: 43: amino acid sequence 12 of *Tachypleus tridentatus*-derived factor D SEQ ID NO: 44: amino acid sequence 13 of *Tachypleus tridentatus*-derived factor D SEQ ID NO: 45: amino acid sequence 14 of *Tachypleus tridentatus*-derived factor D SEQ ID NO: 46: amino acid sequence 15 of *Tachypleus tridentatus*-derived factor D SEQ ID NO: 47: amino acid sequence 16 of *Tachypleus tridentatus*-derived factor D SEQ ID NO: 48: amino acid sequence 17 of *Tachypleus tridentatus*-derived factor D SEQ ID NO: 49: amino acid sequence 18 of *Tachypleus tridentatus*-derived factor D SEQ ID NO: 50: amino acid sequence 19 of *Tachypleus tridentatus*-derived factor D SEQ ID NO: 51: amino acid sequence 5 of *Limulus polyphemus*-derived factor D SEQ ID NO: 52: amino acid sequence 6 of *Limulus polyphemus*-derived factor D SEQ ID NO: 53: amino acid sequence 7 of *Limulus polyphemus*-derived factor D SEQ ID NO: 54: amino acid sequence 8 of *Limulus polyphemus*-derived factor D SEQ ID NO: 55: amino acid sequence 9 of *Limulus polyphemus*-derived factor D SEQ ID NO: 56: amino acid sequence 10 of *Limulus polyphemus*-derived factor D SEQ ID NO: 57: amino acid sequence 11 of *Limulus polyphemus*-derived factor D SEQ ID NO: 58: amino acid sequence 12 of *Limulus polyphemus*-derived factor D SEQ ID NO: 59: amino acid sequence 13 of *Limulus polyphemus*-derived factor D SEQ ID NO: 60: amino acid sequence 14 of *Limulus polyphemus*-derived factor D SEQ ID NO: 61: amino acid sequence 15 of *Limulus polyphemus*-derived factor D SEQ ID NO: 62: amino acid sequence 16 of *Limulus polyphemus*-derived factor D SEQ ID NO: 63: amino acid sequence 17 of *Limulus polyphemus*-derived factor D SEQ ID NO: 64: amino acid sequence 18 of *Limulus polyphemus*-derived factor D SEQ ID NO: 65: amino acid sequence 19 of *Limulus polyphemus*-derived factor D SEQ ID NO: 66: amino acid sequence 20 of *Limulus polyphemus*-derived factor D SEQ ID NO: 67: amino acid sequence 1 of *Carcinoscorpius rotundicauda*-derived factor D SEQ ID NO: 68: amino acid sequence 1 of *Carcinoscorpius rotundicauda*-derived factor D (mature)

SEQ ID NO: 69: amino acid sequence 1 of *Tachypleus gigas*-derived factor D

SEQ ID NO: 70: amino acid sequence 1 of *Tachypleus gigas*-derived factor D (mature)

SEQ ID NO: 71: nucleotide sequence 1 of *Carcinoscorpius rotundicauda*-derived factor D SEQ ID NO: 72: nucleotide sequence 1 of *Tachypleus gigas*-derived factor D

The invention claimed is:

1. A reagent for β-glucan measurement, comprising a horseshoe crab-derived factor D, a horseshoe crab-derived factor G, a horseshoe crab-derived proclotting enzyme, and a substrate for measurement, wherein the factor D is a recombinant protein.

2. The reagent for β-glucan measurement according to claim 1, wherein the horseshoe crab-derived factor G, and the horseshoe crab-derived proclotting enzyme are recombinant proteins.

3. The reagent for β-glucan measurement according to claim 1, wherein a detection limit for pachyman is 20 pg/mL or less within a reaction time of 60 minutes.

4. The reagent for β-glucan measurement according to claim 1, wherein the horseshoe crab-derived factor D is the following protein (1) or (2):

(1) a protein that contains an amino acid sequence of any one of SEQ ID NOS: 1 to 12, 32, 33, and 67 to 70; or (2) a protein that contains an amino acid sequence having about 85% or more identity to at least one amino acid sequence of SEQ ID NOS: 1 to 12, 32, 33, and 67 to 70, and has the function of the factor D.

5. The reagent for β-glucan measurement according to claim 1, wherein the horseshoe crab-derived factor D is the following protein (1') or (2'):

(1') a protein that contains an amino acid sequence of any one of SEQ ID NOS: 2, 4, 6, 8, 10, 12, 33, 68, and 70; or (2') a protein that contains an amino acid sequence having about 85% or more identity to at least one amino acid sequence of SEQ ID NOS: 2, 4, 6, 8, 10, 12, 33, 68, and 70, and has the function of the factor D.

6. The reagent for β-glucan measurement according to claim 1, wherein the horseshoe crab-derived factor D is derived from *Tachypleus tridentatus, Limulus polyphemus, Carcinoscorpius rotundicauda*, or *Tachypleus gigas*.

7. A β-glucan assay method, comprising measuring a β-glucan in a sample using the reagent for β-glucan measurement according to claim 1.

8. A test method for mycosis, comprising:

performing the β-glucan assay method according to claim 7, wherein the sample is a biological sample derived from a test subject suspected of having mycosis.

9. A data acquisition method for diagnosing mycosis, comprising:

acquiring data for diagnosing whether a test subject has mycosis by performing the β-glucan assay method according to claim 7, wherein the sample is a biological sample derived from the test subject.

10. A method for enhancing the activity of a reagent for β-glucan measurement containing a horseshoe crab-derived factor G, a horseshoe crab-derived proclotting enzyme, and a substrate for measurement, comprising combining a horseshoe crab-derived factor D with the reagent for β-glucan measurement.

11. The reagent for β-glycan measurement according to claim 1, not comprising a horseshoe crab hemocyte extract.

* * * * *